US008791238B2

(12) United States Patent
Fiedler et al.

(10) Patent No.: US 8,791,238 B2
(45) Date of Patent: *Jul. 29, 2014

(54) ARTIFICIAL BINDING PROTEINS BASED ON UBIQUITIN

(75) Inventors: Markus Fiedler, Halle (DE); Ulrike Fiedler, Halle (DE); Rainer Rudolph, Halle (DE)

(73) Assignee: Scil Proteins GmbH, Halle-Saale (DE)

(*) Notice: Subject to any disclaimer, the term of this patent is extended or adjusted under 35 U.S.C. 154(b) by 399 days.

This patent is subject to a terminal disclaimer.

(21) Appl. No.: 12/072,959

(22) Filed: Feb. 29, 2008

(65) Prior Publication Data
US 2008/0171851 A1    Jul. 17, 2008

Related U.S. Application Data

(60) Division of application No. 11/283,332, filed on Nov. 18, 2005, which is a continuation of application No. PCT/EP2004/005730, filed on May 27, 2004.

(30) Foreign Application Priority Data

May 28, 2003  (DE) ................................ 103 24 447

(51) Int. Cl.
| A61K 38/00 | (2006.01) |
| C12N 15/10 | (2006.01) |
| C07K 14/00 | (2006.01) |
| C40B 40/02 | (2006.01) |
| G01N 33/68 | (2006.01) |

(52) U.S. Cl.
CPC ........ C12N 15/1044 (2013.01); C07K 2319/00 (2013.01); C07K 14/00 (2013.01); C40B 40/02 (2013.01); G01N 33/6872 (2013.01); C12N 15/1037 (2013.01)
USPC ......................................... 530/350; 435/69.1

(58) Field of Classification Search
None
See application file for complete search history.

(56) References Cited

U.S. PATENT DOCUMENTS

| 4,873,192 | A |  | 10/1989 | Kunkel |  |
| 5,789,166 | A |  | 8/1998 | Bauer et al. |  |
| 5,958,684 | A | * | 9/1999 | Van Leeuwen et al. | ......... 435/6 |
| 6,673,901 | B2 |  | 1/2004 | Koide |  |
| 6,799,121 | B2 | * | 9/2004 | Chu et al. | ......... 702/20 |
| 7,601,803 | B1 |  | 10/2009 | Fiedler et al. |  |
| 7,838,629 | B2 |  | 11/2010 | Fiedler et al. |  |
| 8,592,144 | B2 |  | 11/2013 | Fiedler et al. |  |
| 8,592,179 | B2 |  | 11/2013 | Schraeml et al. |  |
| 2003/0073623 | A1 |  | 4/2003 | Drmanac et al. |  |
| 2004/0043386 | A1 |  | 3/2004 | Pray et al. |  |
| 2006/0058510 | A1 |  | 3/2006 | Skerra et al. |  |
| 2006/0099686 | A1 |  | 5/2006 | Fiedler et al. |  |
| 2007/0111287 | A1 |  | 5/2007 | Fiedler et al. |  |
| 2007/0248536 | A1 | 10/2007 | Fiedler et al. |
| 2010/0130720 | A1 | 5/2010 | Schraeml et al. |
| 2012/0301393 | A1 | 11/2012 | Steuernagel et al. |
| 2013/0011334 | A1 | 1/2013 | Steuernagel et al. |
| 2013/0097737 | A1 | 4/2013 | Kovalic et al. |
| 2013/0157878 | A1 | 6/2013 | Kunert et al. |

FOREIGN PATENT DOCUMENTS

| AU | 2010332932 | 6/2011 |
| AU | 2010332938 | 6/2011 |
| CN | 1956996 | 5/2007 |
| DE | WO 99/16873 | 4/1999 |
| DE | WO 01/04144 | 1/2001 |
| FR | 2 761 688 A | 10/1998 |
| RU | 2134696 C1 | 8/1999 |
| WO | WO97/16556 | 5/1997 |
| WO | WO97/45544 | 12/1997 |
| WO | WO98/44121 | 10/1998 |
| WO | WO98/54312 | 12/1998 |
| WO | WO99/58570 | 11/1999 |
| WO | WO01/62298 | 8/2001 |
| WO | WO01/62800 | 8/2001 |
| WO | WO2004/106368 | 12/2004 |
| WO | WO 2004/106368 | 12/2004 |
| WO | WO2005/044845 | 5/2005 |
| WO | WO2005/059131 | 6/2005 |
| WO | WO2006/040129 | 4/2006 |
| WO | WO2006/119897 | 11/2006 |
| WO | WO2007/054120 | 5/2007 |
| WO | WO2007/115837 | 10/2007 |
| WO | WO2007/128563 | 11/2007 |
| WO | WO2008/022759 | 2/2008 |
| WO | WO2008/059011 | 5/2008 |
| WO | WO2008/096012 | 8/2008 |
| WO | WO2011/073208 | 6/2011 |
| WO | WO2011/073209 | 6/2011 |
| WO | WO2011/073214 | 6/2011 |

OTHER PUBLICATIONS

Seffernick et al. (J. Bacteriology, vol. 183, pp. 2405-2410, 2001).*
Wells, Biochemistry, vol. 29, pp. 8509-8517, 1990.*
International Search Report dated Oct. 5, 2004.
International Preliminary Examination Report dated May 13, 2005.
Burch et al: "Site-directed Mutagenesis of Ubiquitin. Differential Roles for Arginine in the Interaction with Ubiquitin-activating Enzyme," *Biochemistry*, vol. 33, No. 23, Jun. 14, 1994, pp. 7300-7308. (Abstract).
Ecker et al., "Gene Synthesis, Expression, Structures, and Functional Activities of Site-specific Mutants of Ubiquitin," *J. of Biological Chemistry*, vol. 262, No. 29, pp. 14213-14221.
"Fold: beta-Grasp (ubiquitin-like)," scop.mrc-lmb.cam.ac.uk/scop/data/scop.b.e.ca.html, Mar. 15, 2004. (Abstract).
Larsen et al., "The Ubiquitin Superfamily: Members, Features, and Phylogenies," *J. of Proteome Research*, vol. 1, 2002, pp. 411-419.

(Continued)

*Primary Examiner* — Hope Robinson
(74) *Attorney, Agent, or Firm* — Jenkins, Wilson, Taylor & Hunt, P.A.

(57) ABSTRACT

The invention relates to modified proteins of the superfamily of "ubiquitin-like proteins", proteins that have a ubiquitin-like fold and fragments or fusion proteins thereof. As a result of said modification, the proteins have a binding affinity with respect to a predetermined binding partner that did not exist previously. The invention also relates to a method for the production and utilization of said proteins.

22 Claims, 10 Drawing Sheets

(56) References Cited

OTHER PUBLICATIONS

Riddle et al: "Functional Rapidly Folding Proteins from Simplified Amino Acid Sequences," *Nat Struct Biology*, vol. 4, No. 10, Oct. 1997, pp. 805-809. (Abstract).

Skerra, A: "Engineered Protein Scaffolds for Molecular Recognition," *Journal of Molecular Recognition*, vol. 13, No. 4, Jul. 2000, pp. 167-187.

Yeh et al: "Ubiquitin-like Proteins: New Wines in New Bottles," *Elsevier Biomedical Press*, vol. 248, No. 1-2, May 2000, pp. 1-14.

International Preliminary Report on Patentability dated Apr. 13, 2006.

Rudinger, J., "Characteristics of the Amino Acids as Components of a Peptide Hormone Sequence," *University Park Press*, Baltimore, MD, (1976) pp. 1-7.

Bowie et al., "Deciphering the Message in Protein Sequences: Tolerance to Amino Acid Substitutions," *Science*, vol. 247 (1990), pp. 1306-1310.

U.S. Appl. No. 11/283,332 dated May 30, 2008.

Non-final Office Action from U.S. Appl. No. 11/283,332 dated Nov. 28, 2008.

Official Action corresponding to U.S. Appl. No. 11/283,332 dated Jan. 9, 2008.

Official Action corresponding to U.S. Appl. No. 11/283,332 dated Sep. 4, 2009.

Abedi et al, "Green fluorescent protein as a scaffold for intracellular presentation of peptides," Nucleic Acids Research. vol. 26, No. 2 pp. 623-630 (1998).

Advisory Action corresponding to U.S. Appl. No. 10/030,605 dated Oct. 13, 2006.

Advisory Action corresponding to U.S. Appl. No. 11/732,632 dated Jun. 30, 2010.

Baker et al., "Protein Expression Using Cotranslational Fusion and Cleavage of Ubiquitin," The Journal of Biological Chemistry. vol. 269, No. 41 pp. 25381-25386 (1994).

Blundell et al, "The molecular structure and stability of the eye lens: X-ray analysis of γ-crystallin II," Nature. vol. 289 pp. 771-777 (1981).

Brinkmann et al., "Stabilization of a Recombinant Fv Fragment by Base-Loop Interconnection and $V_H$-$V_L$ Permutation," Journal of Molecular Biology. vol. 268 pp. 107-117 (1997).

Butt et al., "Ubiquitin fusion augments the yield of cloned gene products in *Escherichia coli*," PNAS. vol. 86 pp. 2540-2544 (1989).

Campion et al., "Biochemical Properties of Site-Directed Mutants of Human Epidermal Factor: Importance of Solvent-Exposed Hydrophobic Residues of the Amino-Terminal Receptor Binding," Biochemistry. vol. 29, No. 42 pp. 9988-9993 (1990).

Chirgadze et al., "Structure fo the Bovine Eye Lens γD (γIIIb)-Crystallin at 1.95 Å," Acta Cryst. vol. D52 pp. 712-721 (1996).

Choo, Y., and Klug, A., "Designing DNA-binding proteins on the surface of filamentous phage," Current Opinion in Biotechnology. vol. 6 pp. 431-436 (1995).

Colcher et al., "Pharmacokinetics and biodistribution of genetically-engineered antibodies," Q.J. Nucl. Med. vol. 42 pp. 225-241 (1998).

Cortese et al., "Selection of biologically active peptides by phage display of random peptide libraries," Current Opinion in Biotechnology. vol. 7 pp. 616-621 (1996).

Crameri et al., "Molecular evolution of an arsenate detoxification pathway by DNA shuffling," Nature Biotechnology. vol. 5 pp. 436-438 (1997).

Cumber et al., "Comparative stabilities in vitro and in vivo of a recombinant mouse antibody FvCys fragment and a bisFvCys conjugate," Journal of Immunology. vol. 149, No. 1 pp. 120-126 (1992).

de Kruif et al., "Selection and Application of Human Single Chain Fv Antibody Fragments from a Semi-synthetic Phage Antibody Display Library with Designed CDR3 Regions," Journal of Molecular Biology. vol. 248 pp. 97-105 (1995).

den Dunnen et al., Database PIR_79, Accession No. A24060; Gene. vol. 38 pp. 197-204 (1985).

den Dunnen et al., Database PIR_79, Accession No. B24060; J. Mol. Biol. vol. 189 pp. 37-46 (1986).

Ebersbach et al., "Affilin-Novel Binding Molecules Based on Human γ-B-Crystallin, an All β-Sheet Protein," Journal of Molecular Biology. vol. 372 pp. 172-185 (2007).

European Office Action corresponding to European Patent Application No. 00 944 034.8-2401 dated Oct. 7, 2004.

European Patent Office Examination Report corresponding to Euopean Patent Application No. 06118519.5-2401 dated Apr. 2, 2007.

European Search Report corresponding to European Patent Application No. 09176574.3-2401 dated Jan. 18, 2010.

Exley, D., and Woodhams, B., "The Specificity of Antisera Raised by Oestradiol-17β-3-Hemisuccinyl-Bovine Serum Albumin," Steroids. vol. 27, No. 6 pp. 813-820 (1976).

Finucane et al., "Core-Directed Protein Design. I. An Experimental Method for Selecting Stable Proteins from Combinatorial Libraries," Biochemistry. vol. 38 pp. 11604-11612 (1999).

Genbank Accession No. M16894. Hay et al., "cDNA clones encoding bovine gamma-crystallins," Biochem. Biophys. Res. Comm. vol. 146, No. 1 pp. 332-338 (1987).

Genbank Accession No. P07316. den Dunnen et al., "Two human gamma-crystallin genes are linked and riddle with Alu-repeats," Gene. vol. 38, Nos. 1-3 pp. 197-204 (1985).

Glockshuber et al., "A Comparision of Strategies to Stabilize Immunoglobulin Fv-Fragments," Biochemistry. vol. 29 pp. 1362-1367 (1990).

Graw et al., Database UniProt, Accession No. P04344; Gene. vol. 136 pp. 145-156.

Guo et al., "Protein tolerance to random amino acid change," PNAS. vol. 101, No. 25 pp. 9205-9210 (2004).

Haaparanta, T., and Huse, W.D., "A combinatorial method for constructing libraries of long peptides displayed by filamentous phage," Mol. Diversity. vol. 1 pp. 39-52 (1995).

Habeeb, A. F. S. A. "Reaction of protein sulfhydryl groups with Ellman's reagent," In Methods Enzymology, C. H. Hirs, and S. N. Timasheff, eds., pp. 457-464 (1972).

Hazes, B., and Hol, W.G.J., "Comparision of the Hemocyanin β-Barrel with Other Greek Key β-Barrels: possible Importance of the 'β-Zipper' in Protein Structure and Folding," Proteins: Structure, Function, and Genetics. vol. 12 pp. 278-298 (1992).

Hemmingsen et al., "The tyrosine corner: A feature of most Greek key β-barrel proteins," Protein Science. vol. 3 pp. 1927-1937 (1994).

Herrmann, J.E., and Morse, S.A., "Coupling of Peroxidase to Poliovirus Antibody: Characteristics of the Conjugates and Their Use in Virus Detection," Infection and Immunity. vol. 8, No. 4 pp. 645-649 (1973).

Holliger, H., and Winter, G., "Engineering bispecific antibodies," Current Opinion in Biotechnology. vol. 4 pp. 446-449 (1993).

International Search Report corresponding to International Patent Application No. PCT/EP2000/006698 dated Feb. 2, 2001.

International Search Report corresponding to International Patent Application No. PCT/EP2005/010932 dated Apr. 11, 2006.

Interview Summary corresponding to U.S. Appl. No. 11/656,646 dated Feb. 5, 2010.

Jaenicke, "Eye-Lens Proteins: Structure, Superstructure, Stability, Genetics," Naturwissenschaften. vol. 81 pp. 423-429 (1994).

Jaenicke, "Stability and folding of domain proteins," Progression in Biophysics and Molecular Biology. vol. 71, No. 2 p. 155-241 (1999).

Jaenicke, R., and Slingsby, C., Lens Crystallins and Their Microbial Homologs: Structure, Stability, and Function. Critical Reviews in Biochemistry and Molecular Biology. vol. 36, No. 5 pp. 435-499 (2001).

Jenkins et al., "Structure and Evolution of Parallel β-Helix Proteins," Journal of Structural Biology. vol. 122 pp. 236-246 (1998).

Ku, J., and Schultz, P.G. "Alternate protein frameworks for molecular recognition," PNAS. vol. 92 pp. 6552-6556 (1995).

Kumaraswamy, et al., "An Eye Lens Protein-Water Structure: 1.2 Å Resolution Structure of γβ-Crystallin at 150K," Acta Crystallogr. D Biol. Crystallogr. vol. D52 pp. 611-622 (1996).

(56) References Cited

OTHER PUBLICATIONS

Laub et al., "Localized solution structure refinement of an F45W variant of ubiquitin using stochastic boundary molecular dynamics and NMR distance restraints," Protein Science. vol. 4 pp. 973-982 (1995).

Ling, M. M., "Large Antibody Display Libraries for Isolation of High-Affinity Antibodies," Combinatorial Chemistry & High Throughput Screening. vol. 6 pp. 421-432 (2003).

Mandel et al., "Structure and Stability of γ-Crystallins: Denaturation and Proteolysis Behaviour," The Journal of Biological Chemsitry. vol. 262, No. 17 pp. 8096-8102 (1987).

Mayr et al., "Domain Interactions and Connecting Peptides in Lens Crystallins," Journal of Molecular Biology. vol. 235 pp. 84-88 (1994).

McConnell et al., "Construction and screening of M13 phage libaries displaying long random peptides," Molecular Diversity. vol. 1 pp. 165-176 (1995).

Müller, H.N., and Skerra, A., "Grafting of a High-Affinity Zn(II)-Binding Site on the β-Barrel of Retional-Binding Protein Results in Enhanced Folding Stability and Enables Simplified Purification," Biochemistry. vol. 33, No. 47 pp. 14126-14135 (1994).

Najmudin et al., "Structure of the Bovine Eye Lens Protein γB(γII)-Crystallin at 1.47 Å," Acta Cryst. vol. D49 pp. 223-233 (1993).

Nissim et al., "Antibody fragments from a 'single pot' phage display library as immunochemical reagents," The EMBO Journal. vol. 13, No. 3 pp. 692-698 (1994).

Norledge et al., "The X-ray structures of two mutant crystallin domains shed light on the evolution of multi-domain proteins," Nature Structural Biology. vol. 3, No. 3 pp. 267-274 (1996).

Notice of Allowance corresponding to U.S. Appl. No. 10/030,605 dated Apr. 14, 2009.

Notice of Allowance corresponding to U.S. Appl. No. 11/732,632 dated Aug. 23, 2010.

Notification of Transmittal of Translation of the International Preliminary Report on Patentability (Chapter I or Chapter II of the Patent Cooperation Treaty) corresponding to International Application No. PCT/EP2005/010932 dated May 3, 2007.

Nygren, P., and Uhlen, M., "Scaffolds for engineering novel binding sites in proteins," Current Opinion in Structural Biology. vol. 7 pp. 463-469 (1997).

Official Action corresponding to U.S. Appl. No. 10/030,605 dated Sep. 21, 2004.

Official Action corresponding to U.S. Appl. No. 10/030,605 dated Feb. 15, 2005.

Official Action corresponding to U.S. Appl. No. 10/030,605 dated Aug. 10, 2005.

Official Action corresponding to U.S. Appl. No. 10/030,605 dated Apr. 12, 2006.

Official Action corresponding to U.S. Appl. No. 10/030,605 dated Feb. 28, 2007.

Official Action corresponding to U.S. Appl. No. 10/030,605 dated Nov. 16, 2007.

Official Action corresponding to U.S. Appl. No. 10/030,605 dated Jul. 1, 2008.

Official Action corresponding to U.S. Appl. No. 11/656,646 dated Sep. 1, 2009.

Official Action corresponding to U.S. Appl. No. 11/656,646 dated Nov. 13, 2009.

Official Action corresponding to U.S. Appl. No. 11/656,646 dated May 25, 2010.

Official Action corresponding to U.S. Appl. No. 11/732,632 dated Jun. 3, 2009.

Official Action corresponding to U.S. Appl. No. 11/732,632 dated Aug. 21, 2009.

Official Action corresponding to U.S. Appl. No. 11/732,632 dated Mar. 19, 2010.

Pack, P., and Pluckthun, A., "Miniantibodies: Use of Amphipathic Helices to Produce Functional, Flexibly Linked Dimeric Fv Fragments with High Avidity in *Escherichia coli*," Biochemsitry. vol. 31, No. 6 pp. 1579-1584 (1992).

Palme et al., "Mutational analysis of hydrophobic domain interactions in γβ-crystallin from bovine eye lens," Protein Science. vol. 6 pp. 1529-1536 (1997).

Pantoliano et al., "Conformational Stability, Folding, and Ligand-Binding Affinity of Single-Chain Fv Immunoglobulin Fragments Expressed in *Escherichia coli*," Biochemistry. vol. 30 pp. 10117-10125 (1991).

Pickersgill et al., "Crystal Structure of Polygalacturonase from *Erwinia caratovora* ssp. *carotovora*," The Journal of Biological Chemistry. vol. 273, No. 38 pp. 24600-24664 (1998).

Raetz, C.H.R., and Roderick, S.L., "A Left-Handed Parallel β Helix in the Structure of UDP-*N*-Acetylglucosamine Acyltransferase," Science. vol. 270, No. 5238 pp. 997-1000 (1995).

Reichlin, M., "Use of Glutaraldehyde as a Coupling Agent for Proteins and Peptides," Methods in Enzymology. vol. 70 pp. 159-165 (1980).

Richardson et al., "Looking at proteins: representations, folding, packing, and design," Biophysical Journal. vol. 63 pp. 1186-1209 (1992).

Rudolph et al., "Folding of an all-β protein: Independent domain folding in γll-crystallin from calf eye lens," PNAS. vol. 87 pp. 4625-4629 (1990).

Saviranta et al., "Engineering the steroid-specificity of an anti-17β-estradiol Fab by random mutagenesis and competitive phage panning," Protein Engineering. vol. 11, No. 2 pp. 143-152 (1998).

Sharma et al., "Limited proteolysis of γll-crystallin from calf eye lens. Physicochemical studies on the N-terminal domain and the intact two-domain protein," Eur. J. Biochem. vol. 194 pp. 603-609 (1990).

Slingsby, "Structural variation in lens crystallins," TIBS. vol. 10 pp. 281-284 (1985).

Slingsby, C., and Clout, N.J., "Structure of the Crystallins," Eye (London). vol. 13 pp. 395-402 (1999).

Smith, "Filamentous Fusion Phage: Novel Expression Ventors That Display Cloned Antigens on the Virion Surface," Science. vol. 228 pp. 1315-1317 (1985).

Smith et al., "Small Binding Proteins Selected from a Conbinatorial Repertoire of Knottins Displayed on Phage," Journal of Molecular Biology. vol. 277, No. 2 pp. 317-332 (1998).

Stahl, S., and Uhlen, M., "Bacterial surface display: trends and progress," TIBTECH. vol. 15 pp. 185-192 (1997).

Takamiya et al., "A Two-Stage Method for Cross-Linking Antibody Globulin to Ferritin by Glutaraldehyde. III. Size and Antibody Activity of the Conjugates," Journal of Immunological Methods. vol. 8, No. 4 pp. 301-306 (1975).

Ubiquitin-like Superfamily Statistics from <http://supfam.cs.bris.ac.uk/SUPERFAMILY/cgi-bin/scop.cgi?sunid=54236> obtained on Mar. 16, 2010—from Superfamily v. 1.73—HMM library and genome assignments server.

Vijay-Kumar et al., "Three-dimensional structure of ubiquitin at 2.8 Å resolution," PNAS. vol. 82 pp. 3582-3585 (1985).

Voet and Voet, Biochemistry. Chapter 7. Three-Dimensional Structures of Proteins. pp. 171 and 175 (1990).

Wistow et al., "X-ray Analysis of the Eye Lens Protein γ-II-Crystallin at 1.9 A Resolution," Journal of Molecular Biology. vol. 170 pp. 175-202 (1983).

Wistow, G.J., and Piatigorsky, J., "Lens crystallins: the evolution and expression of proteins for a highly specialized tissue," Annual Review of Biochemistry. vol. 57 pp. 479-504 (1988).

Xia et al., "Crystal structure of the receptor-binding domain of adenovirus type 5 fiber protein at 1.7 A resolution," Structure. vol. 2 pp. 1259-1270 (1994).

You, L., and Arnold, F.H., "Directed evolution of subtilisin E in *Bacillus subtilis* to enhance total activity in aqueous dimethylformamide," Protein Engineering. vol. 9, No. 1 pp. 77-83 (1994).

Young et al., "Thermal stabilization of a single-chain Fv antibody fragment by introduction of a disulphide bond," FEBS Letters. vol. 377 pp. 135-139 (1995).

Zhang et al., "Directed evolution of a fucosidase from a galactosidase by DNA shuffling and screening," PNAS. vol. 94 pp. 4504-4509 (1997).

(56) References Cited

OTHER PUBLICATIONS

Bazarsuren et al., "In vitro folding, functional characterization, and disulfide pattern of the extracellular domain of human GLP-1 receptor," Biophysical Chemistry. vol. 96 pp. 305-318 (2002).
Beal et al., "Surface hydrophobic residues of multiubiquitin chains essential for proteolytic targeting," PNAS. vol. 93 pp. 861-866 (1996).
Berman et al., "The Protein Data Bank," Nucleic Acid Res. vol. 28 pp. 235-242 (2000).
Beste, et al., "Small antibody-like proteins with prescribed ligand specificities derived from the lipocalin fold," PNAS. vol. 96 pp. 1898-1903 (1999).
Bird et al., "Single-Chain Antigen-Binding Proteins," Science. vol. 242 pp. 423-426 (1988).
Brinkmann et al., "A recombinant immunotoxin containing a disulfide-stabilized Fv-fragment," PNAS. vol. 90 pp. 7538-7542 (1993).
Buchberger et al., "National Library of Medicine," J Mol Biol. vol. 307, No. 1; pp. 17-24 (2001).
Carter et al., "High level *Escherichia coli* expression and production of a bivalent humanized antibody fragment," Nature Biotechnology. vol. 10 pp. 163-167 (1992).
Chen et al., "Direct Interaction of Hepatitis C Virus Core Protein with the Cellular Lymphotoxin-Receptor Modulates the Signal Pathway of the Lymphotoxin-Receptor," Journal of Virology. vol. 71, No. 12 pp. 9417-9426 (1997).
Connolly, "Solvent-accessible surfaces of proteins and nucleic acids." Science. vol. 221, No. 4612 pp. 709-713 (1983).
Daugherty et al., "Antibody affinity maturation using bacterial surface display," Protein Eng. vol. 11 pp. 825-832 (1998).
Filippi et al., "Linkage and sequence conservation of the X-linked genes DX253 (P3) and DXS254E (GdX) in mouse and man," Genomics. vol. 7 pp. 453-457 (1990).
Finucane et al., "Core-Directed Protein Design. II. Rescue of a Multiply Mutated and Destabilized Variant of Ubiquitin." Biochemistry. vol. 38, No. 36 pp. 11613-11623 (1999).
Folgori et al., "Vaccine-Induced T-Cell Responses Against HCV: One Step Taken, More to Follow," Gastroenterology. vol. 132, No. 4 pp. 1626-1628.
Genbank Accession No. D10934. Wang et al., "Prevalence, genotypes, and an isolate (HC-C2) of hepatitis C virus in Chinese patients with liver disease," J. Med. Virology. vol. 40, No. 3 pp. 254-260 (1993).
Genbank Accession No. 1UBQ. Schlesinger,D.H. and Goldstein,G., "Hybrid troponin reconstituted from vertebrate and arthropod subunits," Nature. vol. 255, No. 5507 pp. 423-424 (1975).
Griep et al., "Fluobodies: Green fluorescent single-chain Fv fusion proteins," J. Immunol. Methods. vol. 230 pp. 121-130 (1999).
Hanes et al., "Picomolar affinity antibodies from a fully synthetic naive library selected and evolved by ribosome display," Nature Biotechnology. vol. 18 pp. 1287-1292 (2000).
Hanes et al., "Ribosome display efficiently selects and evolves high-affinity antibodies in vitro from immune libraries," Proc. Natl. Acad. Sci. vol. 95 pp. 14130-14135 (1998).
Hanes, J., and Pluckthun, A., "In vitro selection and evolution of functional proteins by using ribosome display," PNAS. vol. 94 pp. 4937-4942 (1997).
He and Taussig, "Antibody-ribosome-mRNA(ARM) complexes as efficient selection particles for in vitro display and evolution of antibody combining sites," Nucleic Acids Res. vol. 25 pp. 5132-5134 (1997).
Hoess, "Phage display of peptides and protein domains." Curr. Opin. Struct. Biol. vol. 3 pp. 572-579 (1993).
Holliger et al., "'Diabodies': Small bivalent and bispecific antibodies," Proc. Natl. Sci. vol. 90 pp. 6444-6448 (1993).
Hoogenboom et al., "Antibody phage display technology and its applications," Immunotechnology. vol. 4 pp. 1-20 (1998).
Jentsch, S., and Pyrowolakis, G., "Ubiquitin and its kin: how close are the family ties?" Trends in Cell Biology. vol. 10 pp. 335-342 (2000).

Jones and Candido, "Novel ubiquitin-like ribosome protein fusion genes from the nematodes *Caenorhabditis elegans* and *Caenorhabditis briggsae*," J. Biol. Chem. vol. 268 pp. 19545-195451 (1993).
Kieke et al., "Isolation of anti-T cell receptor scFv mutants by yeast surface display," Protein Eng. vol. 10 pp. 1303-1310 (1997).
Knappik et al., "Fully synthetic human combinatorial antibody libraries (HuCAL) based on modular consensus frameworks and CDRs randomized with trinucleotides," J. Mol. Biol., vol. 296 pp. 57-86 (2000).
Koide et al., "The fibronectin type III domain as a scaffold for novel binding proteins," J. Mol. Biol. vol. 284 pp. 1141-1151 (1998).
Kuchner, O. and Arnold, F. H., "Directed evolution of enzyme catalysts," TIBTECH. vol. 15 pp. 523-530 (1997).
Kumar et al., "Cloning of a cDNA which encodes a novel ubiquitin-like protein," Biochem. Biophys. Res. Comniun. vol. 195 pp. 393-399 (1993).
Lazar et al., "De novo design of the hydrophobic core of ubiquitin," Protein Science. vol. 6 pp. 1167-1178 (1997).
Manns et al., "The way forward in HCV treatment—finding the right path," Nature Reviews Drug Discovery. vol. 6 pp. 991-1000 (2007).
Marx, J. "Ubiquitin lives up to its name," Science vol. 297 pp. 1792-1794 (2002).
McConnell, S. and Hoess, R.H. "Tendamistat as a Scaffold for Xonformationally Xonstrained Phage Peptide Libraries," The Journal of Molecular Biology. vol. 250 pp. 460-470 (1995).
Michiels et al., "Fau cDNA encodes a ubiquitin-like-S30 fusion protein and is expressed as an antisense sequence in the Finkel-Biskis-Reilly murine sarcoma virus," Oncogene. vol. 8 pp. 2537-2546 (1993).
Miura et al., "Characterization of the binding interface between ubiquitin and class 1 human ubiquitin-conjugating enzyme 2b by multidimensional heteronuclear NMR spectroscopy in solution," J. Mol. Biol. vol. 290 pp. 213-228 (1999).
Muller et al., "Recombinant single-chain Fv antibody fragment-alkaline phosphatase conjugate for one-step immunodetection in molecular hybridization," J. Immunol. Methods vol. 227 pp. 177-185 (1999).
Muller et al., "SUMO, ubiquitin's mysterious cousin," Nat. Rev. Mol. Cell Biol. vol. 2 pp. 202-210 (2001).
Murzin et al., "SCOP: a structural classification of proteins database for the investigation of sequences and structures," J. Mol. Biol. vol. 247 pp. 536-540 (1995).
Nord et al., "Binding proteins selected from combinatorial libraries of an beta-helical bacterial receptor domain," Nat. Biotechnol. vol. 8 pp. 772-777 (1997).
Odegrip et al., "CIS display: In vitro selection of peptides from libraries of protein-DNA complexes," PNAS vol. 101 pp. 2806-2810 (2003).
Official Action corresponding to U.S. Appl. No. 12/072,959 dated Mar. 3, 2010.
Pannekoek et al., "Functional display of human plasminogen-activator inhibitor 1 (PAI-1) on phages: novel perspectives for structure-function analysis by error-prone DNA synthesis," Gene. vol. 128 pp. 135-140 (1993).
Reiter and Pastan I. "Recombinant Fv immunotoxins and Fv fragments as novel agents for cancer therapy and diagnosis," Trends Biotechnol. vol. 16 pp. 513-520 (1998).
Schaffitzel et al., "In vitro selection and evolution of protein-ligand interactions by ribosome display," Protein-Protein Interactions, A Molecular Cloning Manual, E. Golemis, Ed. Cold Spring Harbor Laboratory Press, New York, pp. 535-567 (2001).
Shrake and Rupley, "Environment and Exposure to Solvent of Protein Atoms Lysozyme and Insuline," J. Mol. Biol. vol. 79 pp. 351-371 (1973).
Skerra and Plückthun, "Assembly of a functional immunoglobulin Fv fragment in *Escherichia coli*," Science vol. 240 pp. 1038-1041 (1988).
Stemmer, "Rapid evolution of a protein in vitro by DNA shuffling," Nature. vol. 370 pp. 389-391 (1994).
Vijay-Kumar et al., "Structure of ubiquitin refined at 1.8 A resolution," J. Mol. Biol. vol. 194 pp. 531-544 (1987).

(56) References Cited

OTHER PUBLICATIONS

Wang et al., "Prevalence, Genotypes, and an Isolate (HC-C2) of Hepatitis C Virus in Chinese Patients With Liver Disease," Journal of Medicinal Virology. vol. 40 pp. 254-260 (1993).
Wells and Lowmann, "Rapid evolution of peptide and protein binding properties in vitro," Curr. Opin. Struct. Biol. vol. 3 pp. 355-362 (1992).
Winter, "Synthetic human antibodies and a strategy for protein engineering," FEBS Lett. vol. 430 pp. 92-94 (1998).
Wintrode et al., "Thermodynamics of ubiquitin unfolding," Proteins Struct. Funct. Genet. vol. 18 pp. 246-253 (1994).
Official Action corresponding to U.S. Appl. No. 11/283,332 dated Mar. 3, 2010.
Notice of Allowance corresponding to U.S. Appl. No. 13/144,809 dated Mar. 3, 2014.
Official Action corresponding to Russian Patent Application No. 2012115491 dated Dec. 23, 2013.
Official Action corresponding to U.S. Appl. No. 13/142,195 dated Feb. 4, 2014.
Raasi Shahri et al, Binding of polyubiquitin chains to ubiquitin-associated (UBA) domains of HHR23A, J. Mol. Biol., 2004, v. 341, p. 1367-1379.
Zahnd et al., "Ribosome display: selecting and evolving proteins in vitro that specifically bind to a target," Nature Methods. vol. 4, No. 3 pp. 269-279 (2007).
Yang et al., "Relationship between folding and function in a sequence-specific miniature DNA-binding protein," Biochemistry. vol. 44, No. 20 pp. 7469-7478 (2005).
Witkowski et al., "Conversion of a beta-ketoacyl synthase to a malonyl decarboxylase by replacement of the active-site cysteine with glutamine," Biochemistry, vol. 38 pp. 11643-11650 (1999).
Search Report corresponding to Chineses Patent Application No. 201080056911.6 dated Jun. 14, 2013.
Rahighi et al., "Specific Recognition of Linear Ubiquitin Chains by NEMO is Important for NF-κB Activation," Cell. vol. 136 pp. 1098-1109 (2009).
Paschke, M., and Höhne, W., "A twin-arginine translocation (Tat)-mediated phage display system," Gene. vol. 350, No. 1 pp. 79-88 (2005).
Ohashi et al., "Efficient protein selection based on ribosome display system with purified components," Biochemical and Biophysical Research Communications. vol. 352 pp. 270-276 (2007).
Official Action corresponding to U.S. Appl. No. 13/144,809 dated Oct. 18, 2013.
Official Action corresponding to U.S. Appl. No. 13/42,195 dated May 29, 2013.
Official Action corresponding to U.S. Appl. No. 13/142,195 dated Feb. 11, 2013.
Official Action corresponding to U.S. Appl. No. 12/514,550 dated Sep. 15, 2011.
Officia Action corresponding to U.S. Appl. No. 12/514,550 dated Mar. 12, 2012.
Official Action corresponding to U.S. Appl. No. 12/514,550 dated Aug. 3, 2011.
Official Action corresponding to U.S. Appl. No. 11/283,332 dated Sep. 3, 2013.
Official Action corresponding to Korean Patent Application No. 10-2011-7018847 dated Jan. 30, 2013.
Official Action corresponding to Chinese Patent Application No. 201080056911.6 dated Jul. 31, 2013.
Notification Concerning Transmittal of International Preliminary Report on Patentability (Chapter I of the Patent Cooperation Treaty) corresponding to International Patent Application No. PCT/EP2010/069674 dated Jun. 28, 2012.
Notification Concerning Transmittal of International Preliminary Report on Patentability (Chapter I of the Patent Cooperation Treaty) corresponding to International Patent Application No. PCT/EP2010/069666 dated Jun. 28, 2012.
Notice of Allowance corresponding to U.S. Appl. No. 12/514,550 dated Sep. 10, 2013.
Notice of Allowance corresponding to U.S. Appl. No. 11/656,646 dated Aug. 27, 2013.
Loladze et al., "Both helical propensity and side-chain hydrophobicity at a partially exposed site in alpha-helix contribute to the thermodynamic stability of ubiquitin," Proteins. vol. 58, No. 1 pp. 1-6 (2005).
Lo et al., "Structure Basis for Recognition of Diubiquitins by NEMO," Molecular Cell. vol. 33 pp. 602-615 (2009).
Lipovsek, D., and Plückthun, A., "In-vitro protein evolution by ribosome display and mRNA display," Journal of Immunological Methods. vol. 290 pp. 51-67 (2004).
Krantz et al., "Discerning the Structure and Energy of Multiple Transition States in Protein Folding using Ψ-Analysis," Journal of Molecular Biology. vol. 337, No. 2 pp. 463-475 (2004).
Kiel, C., and Serrano, L., "The Ubiquitin Domain Superfold: Structure-based Sequence Alignments and Characterization of Binding Epitopes," Journal of Molecular Biology. vol. 355, No. 4 pp. 821-844 (2006).
Khorasanizadeh et al., "Folding and Stability of a tryptophan-containing mutant of ubiquitin." Biochemistry. vol. 32, No. 27 pp. 7054-7063 (1993).
Jackson, "Ubiquitin: a small protein folding paradigm." Org. Biomol. Chem. vol. 4, No. 10 pp. 1845-1853 (2006).
Interview Summary corresponding to U.S. Appl. No. 12/514,550 dated Jun. 12, 2012.
Interview Summary corresponding to U.S. Appl. No. 12/514,550 dated Dec. 13, 2011.
Interview Summary corresponding to U.S. Appl. No. 11/283,332 dated Oct. 10, 2013.
Interview Summary corresponding to U.S. Appl. No. 11/283,332 dated Dec. 13, 2013.
International Search Report corresponding to International Patent Application No. PCT/EP2010/069674 dated Jun. 17, 2011.
International Search Report corresponding to International Patent Application No. PCT/EP2010/069665 dated Apr. 13, 2011.
International Search Report corresponding to International Patent Application No. PCT/EP2007/062375 dated Apr. 25, 2008.
International Preliminary Report on Patentability (Chapter I of the Patent Cooperation Treaty) corresponding to International Patent Application No. PCT/EP2010/069665 dated Jun. 19, 2012.
International Preliminary Report on Patentability (Chapter I of the Patent Cooperation Treaty) corresponding to International Patent Application No. PCT/EP2007/062375 dated May 19, 2009.
Intent to Grant corresponding to European Patent Application No. EP 10 787 815.9-1410 dated Aug. 13, 2013.
Hey et al., "Artificial, non-antibody binding proteins for pharmaceutical and industrial applications," TRENDS in Biotechnology. vol. 23, No. 10 pp. 514-522 (2005).
Hershko, A., and Ciechanover, A., "The Ubiquitin System," Annu. Rev. Biochem. vol. 67 pp. 425-479 (1998).
Grabulovski et al., "A Novel, Non-immunogenic Fyn SH3-derived Binding Protein with Tumor Vascular Targeting Properties," The Journal of Biological Chemistry. vol. 282, No. 5 pp. 3196-3204 (2007).
Gebauer, M., and Skerra, A., "Engineered protein scaffolds as next-generation antibody therapeutics," Current Opinion in Chemical Biology. vol. 13, No. 3 pp. 245-255 (2009).
Fiedler et al., "Affilintm Molecules: Novel Ligands for Bioseparation," Food and Bioproducts Processing. vol. 84, No. C1 pp. 3-8 (2006).
European Search Report corresponding to European Patent Application No. 10 181 802.9-2401 dated Feb. 10, 2011.
Ermolenko et al., "Noncharged amino acid residues at the solvent-exposed positions in the middle and at the C terminus of the alpha-helix have the same helical propensity," Protein Science. vol. 12, No. 6 pp. 1169-1176 (2003).
Dikic et al., "Ubiquitin-binding domains—from structures to functions," Nature Reviews. vol. 10 pp. 659-671 (2009).

(56) References Cited

OTHER PUBLICATIONS

Deed of Grant corresponding to Australian Patent No. 2010332938 dated Apr. 4, 2013.
Deed of Grant corresponding to Australian Patent No. 2010332932 dated May 2, 2013.
Corrected Notice of Allowability corresponding to U.S. Appl. No. 11/656,646 dated Sep. 26, 2013.
Branden, C., and Tooze, J., "Introduction to Protein Structure," Chapter 16, Garland Publishing Inc.: New York, New York p. 247 (1991).
Borsi et al., "Selective targeted delivery of TNFα to tumor blood vessels," Blood. vol. 102, No. 13 pp. 4384-4392 (2003).
Bolton et al., "Structure and Properties of a Dimeric N-terminal Fragment of Human Ubiquitin," Journal of Molecular Biology. vol. 314, No. 4 pp. 773-787 (2001).
Bofill et al., "Engineering Stabilising beta-Sheet Interactions into a Conformationally Flexible Region of the Folding Transition State of Ubiquitin," Journal of Molecular Biology. vol. 353, No. 2 pp. 373-384 (2005).
Berlier et al., "Quantitative Compassion of Long-wavelength Alexa Fluor Dyes to Cy Dyes: Fluorescence of the Dyes and Their Bioconjugates," The Journal of Histochemistry & Cytochemistry. vol. 51, No. 12 pp. 1699-1712.

\* cited by examiner

Seq ID No.29 GTTATTACTTCGCGGGCCCAGCCGGCCATGGCCATG
                                      ====SfiI====

Seq ID No. 30 CCAGCCGGCCATGGCCATGAAGNNKATCNNKGTTNNKACCCTGACGGGAAAGACTATC

ATGAAATACCTATTGCCTACGGCGAGCCGCTGGATTGTTATTACTTCGCGGGGCCCAGCCGGCCATGGCCATGGCCAGCCGGCCATGAAGNNKATCNNKGTTNNKACCCTGACGGGAAAGACTATCACCCTGGAGGTA
---+---------+---------+---------+---------+---------+---------+---------+---------+---------+---------+---------+---------+---------+
TACTTTATGGATAACGGATGCCGTCGGCGACCTAACAATAATGAGCGCGGGCCGGTCGGCCGGTACGTTAGAAGCAATTTGGGACTGCCCTTTCTGATAGTGGGACCTCCAT

MetLysTyrLeuLeuProThrAlaAlaAlaGlyLeuLeuLeuLeuAlaAlaGlnProAlaMetAlaMetAlaMetXxxIleXxxValXxxThrLeuThrGlyLysThrIleThrLeuGluVal
PolB  →                                                                      Ubiquitin →

GAACCGTCCGACACCATCGAAAATGTCAAAGCTAAATCCAAGACTAAAGAAGAATTCCACCTGACCAGCAACGGCCTAGCTTTTCGCAGGACGACAACTAGAGGACGGGCTCACCCTG
---+---------+---------+---------+---------+---------+---------+---------+---------+---------+---------+---------+
CTTGGCAGGCTGTGGTAGGTTTCGATTTTAGTTCTTCCTTAAGGTGGACTGGTCGTTGCGGATCGAAGACGTCCTGCTGTTGATCTCCTGCCGAGTGGGAC   GGAC

GluProSerAspThrIleGluAsnValLysAlaLysIleGlnAspLysGluGlyIleProProAspGlnGlnArgLeuAlaPheAlaGlyLysGlnLeuGluAspGlyLeuThrLeu

TCTGACTACAACATCCAAAAGAATCCACCCTCCACCTGGCACTCCTCCTGGGGCCCTTGAGAGCCGAACGAAGCAAAGACTCATCTCAGAGAGAGAATCTGTATTCCAGGGCTAG Seq ID No. 32
---+---------+---------+---------+---------+---------+---------+---------+---------+---------+---------+---------+
AGACTGATGTTGTAGGTTTTGTAGGTTGTAGGTTCTTAGGTGGGAGGTGGACCTGGAGGAGGACGGGCCCGGGAGCTCGGCCTTGTTGTTTGAGATAGATCTCTCTCTTAGACATAAGGTCCCGATC

SerAspTyrAsnIleXxxXxxXxxXxxXxxXxxLeuIleSerGluGluAsnLeuTyrPheGlnGlyStp Seq ID No. 33
No. 31

AGACTGATGTTGTTAGNNNNNNNNNNNNNNNNNGAGGTGGACCGTGAGGAGGAC Seq ID No. 33

GACCTGACCCTGAGGAGGACGCCCGGGAGCTCCGGCTTGTTTTGAG Seq ID No. 34
                                   ====SfiI====

*FIGURE 4*

Binding of SPU-3-H13-O to hydrocortisone, testosterone, oestradiol and BSA (carrier protein) - detection by Ni-NTA/POD

SEQUENCE LISTING

```
<160> NUMBER OF SEQ ID NOS: 37

<210> SEQ ID NO 1
<211> LENGTH: 291
<212> TYPE: DNA
<213> ORGANISM: Artificial Sequence
<220> FEATURE:
<223> OTHER INFORMATION: DNA sequence for a modified ubiquitin protein
      scaffold

<400> SEQUENCE: 1
atgaaatacc tattgcctac ggcagccgct ggattgttat tactcgcggc ccagccggcc      60
atggccatgc aaatcttcgt taaaaccctg acgggaaaga ctatcaccct ggaggtagaa    120
ccgtccgaca ccatcgaaaa tgtcaaagct aaaatccaag acaaagaagg aattccacct    180
```

```
gaccagcaac gcctagcttt cgcaggacga caactagagg acgggctcac cctgtctgac      240
tacaacatcc aaaaagaatc caccctccac ctggcactcc tcctgcgggc c               291
```

<210> SEQ ID NO 2
<211> LENGTH: 50
<212> TYPE: DNA
<213> ORGANISM: Artificial Sequence
<220> FEATURE:
<223> OTHER INFORMATION: Artifically synthesized mutagenizing
      oligonucleotide

<400> SEQUENCE: 2

```
atgcaaatct tcgttaaaac cctgacggga aagactatca ccctggaggt                50
```

<210> SEQ ID NO 3
<211> LENGTH: 53
<212> TYPE: DNA
<213> ORGANISM: Artificial Sequence
<220> FEATURE:
<223> OTHER INFORMATION: Artifically synthesized mutagenizing
      oligonucleotide

<400> SEQUENCE: 3

```
ggattttagc tttgacattt tcgatggtgt cggacggttc tacctccagg gtg            53
```

<210> SEQ ID NO 4
<211> LENGTH: 53
<212> TYPE: DNA
<213> ORGANISM: Artificial Sequence
<220> FEATURE:
<223> OTHER INFORMATION: Artifically synthesized mutagenizing
      oligonucleotide

<400> SEQUENCE: 4

```
gtcaaagcta aaatccaaga caaagaagga attccacctg accagcaacg cct            53
```

<210> SEQ ID NO 5
<211> LENGTH: 50
<212> TYPE: DNA
<213> ORGANISM: Artificial Sequence
<220> FEATURE:
<223> OTHER INFORMATION: Artifically synthesized mutagenizing
      oligonucleotide

<400> SEQUENCE: 5

```
gggtgagccc gtcctctagt tgtcgtcctg cgaaagctag gcgttgctgg                50
```

<210> SEQ ID NO 6
<211> LENGTH: 50
<212> TYPE: DNA
<213> ORGANISM: Artificial Sequence
<220> FEATURE:
<223> OTHER INFORMATION: Artifically synthesized mutagenizing
      oligonucleotide

<400> SEQUENCE: 6

```
gacgggctca ccctgtctga ctacaacatc caaaaagaat ccaccctcca                50
```

<210> SEQ ID NO 7
<211> LENGTH: 39
<212> TYPE: DNA
<213> ORGANISM: Artificial Sequence
<220> FEATURE:
<223> OTHER INFORMATION: Artifically synthesized mutagenizing
      oligonucleotide -continued

<400> SEQUENCE: 7
gagtgctcgc agcaggagtg ccaggtggag ggtggattc         39

<210> SEQ ID NO 8
<211> LENGTH: 22
<212> TYPE: DNA
<213> ORGANISM: Artificial Sequence
<220> FEATURE:
<223> OTHER INFORMATION: Artificially synthesized flanking
      oligonucleotide

<400> SEQUENCE: 8
gatatacata tgcaaatctt cg         22

<210> SEQ ID NO 9
<211> LENGTH: 18
<212> TYPE: DNA
<213> ORGANISM: Artificial Sequence
<220> FEATURE:
<223> OTHER INFORMATION: Artificially synthesized flanking
      oligonucleotide

<400> SEQUENCE: 9
gtggtgctcg agtgctcg         18

<210> SEQ ID NO 10
<211> LENGTH: 55
<212> TYPE: DNA
<213> ORGANISM: Artificial Sequence
<220> FEATURE:
<223> OTHER INFORMATION: Artificially synthesized flanking
      oligonucleotide
<220> FEATURE:
<221> NAME/KEY: misc_feature
<222> LOCATION: (1)..(55)
<223> OTHER INFORMATION: k is g or t
<220> FEATURE:
<221> NAME/KEY: misc_feature
<222> LOCATION: (1)..(55)
<223> OTHER INFORMATION: n is a, c, g, or t

<400> SEQUENCE: 10
ccagccggcc atggccatgn nkatcnnkgt tnnkaccctg acgggaaaga ctatc         55

<210> SEQ ID NO 11
<211> LENGTH: 55
<212> TYPE: DNA
<213> ORGANISM: Artificial Sequence
<220> FEATURE:
<223> OTHER INFORMATION: Artificially synthesized flanking
      oligonucleotide
<220> FEATURE:
<221> NAME/KEY: misc_feature
<222> LOCATION: (1)..(55)
<223> OTHER INFORMATION: m is a or c
<220> FEATURE:
<221> NAME/KEY: misc_feature
<222> LOCATION: (1)..(55)
<223> OTHER INFORMATION: n is a, c, g, or t

<400> SEQUENCE: 11
caggaggagt gccaggtgga gmnnmnnmnn mnnmnngatg ttgtagtcag acagg         55

<210> SEQ ID NO 12
<211> LENGTH: 34
<212> TYPE: DNA
<213> ORGANISM: Artificial Sequence

```
<220> FEATURE:
<223> OTHER INFORMATION: Artificially synthesized flanking
      oligonucleotide

<400> SEQUENCE: 12
gttattactc gcggcccagc cggccatggc catg                                      34

<210> SEQ ID NO 13
<211> LENGTH: 48
<212> TYPE: DNA
<213> ORGANISM: Artificial Sequence
<220> FEATURE:
<223> OTHER INFORMATION: Artificially synthesized flanking
      oligonucleotide

<400> SEQUENCE: 13
gagtttttgt tcggcctcga gggcccgcag gaggagtgcc aggtggag                       48

<210> SEQ ID NO 14
<211> LENGTH: 23
<212> TYPE: DNA
<213> ORGANISM: Artificial Sequence
<220> FEATURE:
<223> OTHER INFORMATION: Artificially synthesized sequencing
      oligonucleotide

<400> SEQUENCE: 14
accactccct atcagtgata gag                                                  23

<210> SEQ ID NO 15
<211> LENGTH: 228
<212> TYPE: DNA
<213> ORGANISM: Artificial Sequence
<220> FEATURE:
<223> OTHER INFORMATION: Modified ubiquitin sequence as basis for
      library

<400> SEQUENCE: 15
atgcagatct tcgtgaagac cctgaccggc aagaccatca ctctggaggt ggagcccagt          60
gacaccatcg aaaatgtgaa ggccaagatc aagataaag aaggcattcc ccccgaccag          120
cagaggctca tctgggcagg caagcagctg gaagatggcc gcactctttc tgactacaac         180
atccagaaag agtcgaccct gcacctggtc ctccgcctga ggggcggc                      228

<210> SEQ ID NO 16
<211> LENGTH: 54
<212> TYPE: DNA
<213> ORGANISM: Artificial Sequence
<220> FEATURE:
<223> OTHER INFORMATION: Artificially synthesized flanking
      oligonucleotide
<220> FEATURE:
<221> NAME/KEY: misc_feature
<222> LOCATION: (1)..(54)
<223> OTHER INFORMATION: k is g or t
<220> FEATURE:
<221> NAME/KEY: misc_feature
<222> LOCATION: (1)..(54)
<223> OTHER INFORMATION: n is a, c, g, or t

<400> SEQUENCE: 16
gaaggagata tacatatgnn katcnnkgtt nnkaccctga cgggaaagac tatc                54

<210> SEQ ID NO 17
<211> LENGTH: 55
<212> TYPE: DNA
<213> ORGANISM: Artificial Sequence
```

```
<220> FEATURE:
<223> OTHER INFORMATION: Artificially synthesized flanking
      oligonucleotide
<220> FEATURE:
<221> NAME/KEY: misc_feature
<222> LOCATION: (1)..(55)
<223> OTHER INFORMATION: m is a or c
<220> FEATURE:
<221> NAME/KEY: misc_feature
<222> LOCATION: (1)..(55)
<223> OTHER INFORMATION: n is a, c, g, or t

<400> SEQUENCE: 17
caggaggagt gccaggtgga gmnnmnnmn mnnmnngatg ttgtagtcag acagg        55

<210> SEQ ID NO 18
<211> LENGTH: 54
<212> TYPE: DNA
<213> ORGANISM: Artificial Sequence
<220> FEATURE:
<223> OTHER INFORMATION: Artificially synthesized flanking
      oligonucleotide
<220> FEATURE:
<221> NAME/KEY: misc_feature
<222> LOCATION: (1)..(54)
<223> OTHER INFORMATION: k is g or t
<220> FEATURE:
<221> NAME/KEY: misc_feature
<222> LOCATION: (1)..(54)
<223> OTHER INFORMATION: n is a, c, g, or t

<400> SEQUENCE: 18
gaaggagata tacatatgnn katcnnkgtt nnkaccctga ccggcaagac catc         54

<210> SEQ ID NO 19
<211> LENGTH: 61
<212> TYPE: DNA
<213> ORGANISM: Artificial Sequence
<220> FEATURE:
<223> OTHER INFORMATION: Artificially synthesized flanking
      oligonucleotide
<220> FEATURE:
<221> NAME/KEY: misc_feature
<222> LOCATION: (1)..(61)
<223> OTHER INFORMATION: m is a or c
<220> FEATURE:
<221> NAME/KEY: misc_feature
<222> LOCATION: (1)..(61)
<223> OTHER INFORMATION: n is a, c, g, or t

<400> SEQUENCE: 19
caggaggagt gccaggtgga gmnnmnnmn mnnmnngatg ttgtagtcag aaagagtgcg   60
g                                                                 61

<210> SEQ ID NO 20
<211> LENGTH: 33
<212> TYPE: DNA
<213> ORGANISM: Artificial Sequence
<220> FEATURE:
<223> OTHER INFORMATION: Artificially synthesized flanking
      oligonucleotide

<400> SEQUENCE: 20
caccaccacc accaccaccc tcctgtcaat gct                              33

<210> SEQ ID NO 21
<211> LENGTH: 35
<212> TYPE: DNA
<213> ORGANISM: Artificial Sequence
```

<220> FEATURE:
<223> OTHER INFORMATION: Artificially synthesized flanking
      oligonucleotide

<400> SEQUENCE: 21
ggcccacccg tgaaggtgag cctcagtagc gacag                          35

<210> SEQ ID NO 22
<211> LENGTH: 45
<212> TYPE: DNA
<213> ORGANISM: Artificial Sequence
<220> FEATURE:
<223> OTHER INFORMATION: Artificially synthesized flanking
      oligonucleotide

<400> SEQUENCE: 22
ctggcactcc tcctgcgggc cctcgagcac caccaccacc accac              45

<210> SEQ ID NO 23
<211> LENGTH: 63
<212> TYPE: DNA
<213> ORGANISM: Artificial Sequence
<220> FEATURE:
<223> OTHER INFORMATION: Artificially synthesized flanking
      oligonucleotide

<400> SEQUENCE: 23
agaccacaac ggtttccctc tagaaataat tttgtttaac tttaagaagg agatatacat    60
atg                                                                 63

<210> SEQ ID NO 24
<211> LENGTH: 42
<212> TYPE: DNA
<213> ORGANISM: Artificial Sequence
<220> FEATURE:
<223> OTHER INFORMATION: Artificially synthesized flanking
      oligonucleotide

<400> SEQUENCE: 24
atacgaaatt aatacgactc actataggga gacccacaac gg                  42

<210> SEQ ID NO 25
<211> LENGTH: 55
<212> TYPE: DNA
<213> ORGANISM: Artificial Sequence
<220> FEATURE:
<223> OTHER INFORMATION: Artificially synthesized flanking
      oligonucleotide
<220> FEATURE:
<221> NAME/KEY: misc_feature
<222> LOCATION: (1)..(55)
<223> OTHER INFORMATION: m is a or c
<220> FEATURE:
<221> NAME/KEY: misc_feature
<222> LOCATION: (1)..(55)
<223> OTHER INFORMATION: n is a, c, g, or t

<400> SEQUENCE: 25
caggaggagt gccaggtgga gattcctacc mnnmnngatg ttgtagtcag acagg    55

<210> SEQ ID NO 26
<211> LENGTH: 55
<212> TYPE: DNA
<213> ORGANISM: Artificial Sequence
<220> FEATURE:
<223> OTHER INFORMATION: Artificially synthesized flanking
      oligonucleotide -continued

```
<220> FEATURE:
<221> NAME/KEY: misc_feature
<222> LOCATION: (1)..(55)
<223> OTHER INFORMATION: m is a or c
<220> FEATURE:
<221> NAME/KEY: misc_feature
<222> LOCATION: (1)..(55)
<223> OTHER INFORMATION: n is a, c, g, or t

<400> SEQUENCE: 26
caggaggagt gccaggtgga gattmnnmnn cggcgggatg ttgtagtcag acagg        55

<210> SEQ ID NO 27
<211> LENGTH: 55
<212> TYPE: DNA
<213> ORGANISM: Artificial Sequence
<220> FEATURE:
<223> OTHER INFORMATION: Synthesized mutagenizing oligonucleotide

<400> SEQUENCE: 27
ctcgagcacc accaccacca ccactgtccg tgagatccgg ctgctaacaa agccc         55

<210> SEQ ID NO 28
<211> LENGTH: 55
<212> TYPE: DNA
<213> ORGANISM: Artificial Sequence
<220> FEATURE:
<223> OTHER INFORMATION: Synthesized mutagenizing oligonucleotide

<400> SEQUENCE: 28
gggctttgtt agcagccgga tctcacggac agtggtggtg gtggtggtgc tcgag         55

<210> SEQ ID NO 29
<211> LENGTH: 34
<212> TYPE: DNA
<213> ORGANISM: Artificial Sequence
<220> FEATURE:
<223> OTHER INFORMATION: Construction of a library of ubiquitin
      variants

<400> SEQUENCE: 29
gttattactc gcggcccagc cggccatggc catg                                34

<210> SEQ ID NO 30
<211> LENGTH: 55
<212> TYPE: DNA
<213> ORGANISM: Artificial Sequence
<220> FEATURE:
<223> OTHER INFORMATION: Construction of a library of ubiquitin variants
<220> FEATURE:
<221> NAME/KEY: misc_feature
<222> LOCATION: (1)..(55)
<223> OTHER INFORMATION: k is g or t
<220> FEATURE:
<221> NAME/KEY: misc_feature
<222> LOCATION: (1)..(55)
<223> OTHER INFORMATION: n is a, c, g, or t

<400> SEQUENCE: 30
ccagccggcc atggccatgn nkatcnnkgt tnnkaccctg acgggaaaga ctatc         55

<210> SEQ ID NO 31
<211> LENGTH: 114
<212> TYPE: PRT
<213> ORGANISM: Artificial Sequence
<220> FEATURE:
<223> OTHER INFORMATION: Construction of a library of ubiquitin variants
```

<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (84)..(88)
<223> OTHER INFORMATION: Xaa can be any naturally occurring amino acid

<400> SEQUENCE: 31

Met Lys Tyr Leu Leu Pro Thr Ala Ala Ala Gly Leu Leu Leu Leu Ala
1               5                  10                  15

Ala Gln Pro Ala Met Ala Met Xaa Ile Xaa Val Xaa Thr Leu Thr Gly
            20                  25                  30

Lys Thr Ile Thr Leu Glu Val Glu Pro Ser Asp Thr Ile Glu Asn Val
        35                  40                  45

Lys Ala Lys Ile Gln Asp Lys Glu Gly Ile Pro Pro Asp Gln Gln Arg
    50                  55                  60

Leu Ala Phe Ala Gly Arg Gln Leu Glu Asp Gly Leu Thr Leu Ser Asp
65                  70                  75                  80

Tyr Asn Ile Xaa Xaa Xaa Xaa Xaa Leu His Leu Ala Leu Leu Leu Arg
                85                  90                  95

Ala Leu Glu Ala Glu Gln Lys Leu Ile Ser Glu Glu Asn Leu Tyr Phe
            100                 105                 110

Gln Gly

<210> SEQ ID NO 32
<211> LENGTH: 345
<212> TYPE: DNA
<213> ORGANISM: Artificial Sequence
<220> FEATURE:
<223> OTHER INFORMATION: Construction of a library of ubiquitin variants

<400> SEQUENCE: 32
atgaaatacc tattgcctac ggcagccgct ggattgttat tactcgcggc ccagccggcc      60
atggccatgc aaatcttcgt taaaaccctg acgggaaaga ctatcaccct ggaggtagaa     120
ccgtccgaca ccatcgaaaa tgtcaaagct aaaatccaag acaaagaagg aattccacct     180
gaccagcaac gcctagcttt cgcaggacga caactagagg acgggctcac cctgtctgac     240
tacaacatcc aaaagaatc caccctccac ctggcactcc tcctgcgggc cctcgaggcc     300
gaacaaaaac tcatctcaga agagaatctg tatttccagg gctag                    345

<210> SEQ ID NO 33
<211> LENGTH: 51
<212> TYPE: DNA
<213> ORGANISM: Artificial Sequence
<220> FEATURE:
<223> OTHER INFORMATION: Construction of a library of ubiquitin variants
<220> FEATURE:
<221> NAME/KEY: misc_feature
<222> LOCATION: (1)..(51)
<223> OTHER INFORMATION: m is a or c
<220> FEATURE:
<221> NAME/KEY: misc_feature
<222> LOCATION: (1)..(51)
<223> OTHER INFORMATION: n is a, c, g, or t -continued

<400> SEQUENCE: 33
agactgatgt tgtagnnmnn mnnmnnmnnm gaggtggacc gtgaggagga c        51

<210> SEQ ID NO 34
<211> LENGTH: 48
<212> TYPE: DNA
<213> ORGANISM: Artificial Sequence
<220> FEATURE:
<223> OTHER INFORMATION: Construction of a library of ubiquitin variants

<400> SEQUENCE: 34
gaggtggacc gtgaggagga cgcccgggag ctccggcttg tttttgag              48

<210> SEQ ID NO 35
<211> LENGTH: 76
<212> TYPE: PRT
<213> ORGANISM: Homo sapiens

<400> SEQUENCE: 35

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 36
<211> LENGTH: 228
<212> TYPE: DNA
<213> ORGANISM: Artificial Sequence
<220> FEATURE:
<223> OTHER INFORMATION: Synthesized mutagenesis primer
<220> FEATURE:
<221> NAME/KEY: misc_feature
<222> LOCATION: (1)..(228)
<223> OTHER INFORMATION: k is g or t
<220> FEATURE:
<221> NAME/KEY: misc_feature
<222> LOCATION: (1)..(228)
<223> OTHER INFORMATION: n is a, c, g, or t
<220> FEATURE:
<221> NAME/KEY: CDS
<222> LOCATION: (1)..(228)

<400> SEQUENCE: 36 atg nnk atc nnk gtt nnk acc ctg acg gga aag act atc acc ctg gag    48
Met Xaa Ile Xaa Val Xaa Thr Leu Thr Gly Lys Thr Ile Thr Leu Glu
1               5                   10                  15 gta gaa ccg tcc gac acc atc gaa aat gtc aaa gct aaa atc caa gac    96
Val Glu Pro Ser Asp Thr Ile Glu Asn Val Lys Ala Lys Ile Gln Asp
            20                  25                  30 aaa gaa gga att cca cct gac cag caa cgc cta gct ttc gca gga cga   144
Lys Glu Gly Ile Pro Pro Asp Gln Gln Arg Leu Ala Phe Ala Gly Arg
        35                  40                  45 caa cta gag gac ggg ctc acc ctg tct gac tac aac atc nnk nnk nnk   192
Gln Leu Glu Asp Gly Leu Thr Leu Ser Asp Tyr Asn Ile Xaa Xaa Xaa
    50                  55                  60 nnk nnk ctc cac ctg gca ctc ctc ctg cgg gcc ctc                   228
Xaa Xaa Leu His Leu Ala Leu Leu Leu Arg Ala Leu
65                  70                  75

```
<210> SEQ ID NO 37
<211> LENGTH: 76
<212> TYPE: PRT
<213> ORGANISM: Artificial Sequence
<220> FEATURE:
<221> NAME/KEY: misc_feature
<222> LOCATION: (2)..(2)
<223> OTHER INFORMATION: The 'Xaa' at location 2 stands for Lys, Asn,
      Arg, Ser, Thr, Met, Ile, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (4)..(4)
<223> OTHER INFORMATION: The 'Xaa' at location 4 stands for Lys, Asn,
      Arg, Ser, Thr, Met, Ile, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (6)..(6)
<223> OTHER INFORMATION: The 'Xaa' at location 6 stands for Lys, Asn,
      Arg, Ser, Thr, Met, Ile, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (62)..(62)
<223> OTHER INFORMATION: The 'Xaa' at location 62 stands for Lys, Asn,
      Arg, Ser, Thr, Met, Ile, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (63)..(63)
<223> OTHER INFORMATION: The 'Xaa' at location 63 stands for Lys, Asn,
      Arg, Ser, Thr, Met, Ile, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (64)..(64)
<223> OTHER INFORMATION: The 'Xaa' at location 64 stands for Lys, Asn,
      Arg, Ser, Thr, Met, Ile, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (65)..(65)
<223> OTHER INFORMATION: The 'Xaa' at location 65 stands for Lys, Asn,
      Arg, Ser, Thr, Met, Ile, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (66)..(66)
<223> OTHER INFORMATION: The 'Xaa' at location 66 stands for Lys, Asn,
      Arg, Ser, Thr, Met, Ile, Glu, Asp, Gly, Ala, Val, Gln, His, Pro,
      Leu, Tyr, Trp, Cys, or Phe.
<220> FEATURE:
<223> OTHER INFORMATION: Synthetic Construct

<400> SEQUENCE: 37

Met Xaa Ile Xaa Val Xaa Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ala Phe Ala Gly Arg
        35                  40                  45

Gln Leu Glu Asp Gly Leu Thr Leu Ser Asp Tyr Asn Ile Xaa Xaa Xaa
    50                  55                  60

Xaa Xaa Leu His Leu Ala Leu Leu Arg Ala Leu
65                  70                  75
```

ARTIFICIAL BINDING PROTEINS BASED ON UBIQUITIN

RELATED APPLICATIONS

This application is a divisional of U.S. patent application Ser. No. 11/283,332, filed Nov. 18, 2005, which itself is a continuation of PCT parent application number PCT/EP2004/005730, filed May 27, 2004, which claims priority to German patent application number 10324447.6, filed May 28, 2003, the disclosures of which are incorporated herein by reference in their entireties.

TECHNICAL FIELD

The present invention relates to modified proteins of the protein superfamily of "ubiquitin-like proteins", proteins that have a ubiquitin-like folding motif as well as fragments or fusion proteins thereof wherein as a result of this modification the protein exhibits a binding affinity with respect to a predetermined binding partner that did not exist previously, as well as to methods for the preparation of these proteins and the use thereof.

BACKGROUND ART

Ubiquitin is a small, monomeric, and cytosolic protein which is highly conserved in sequence and is present in all known eukaryotic cells from protozoans to vertebrates. In the organism, it plays a crucial role in the regulation of the controlled degradation of cellular proteins. For this purpose, the proteins destined for degradation are covalently linked to ubiquitin or polyubiquitin chains during their passage through a cascade of enzymes and are selectively degraded because of this label. According to recent results, ubiquitin or the labelling of proteins by ubiquitin, respectively, plays an important role also in other cellular processes such as the import of several proteins or the gene regulation thereof (Marx, 2002).

Besides the clarification of its physiological function, ubiquitin is a research object primarily because of its structural and proteinchemical properties. The polypeptide chain of ubiquitin consists of 76 amino acids folded in an extraordinarily compact α/β structure (Vijay-Kumar, 1987): almost 87% of the polypeptide chain are involved in the formation of the secondary structural elements by means of hydrogen bonds. As prominent secondary structures can be mentioned three and a half alpha-helical turns as well as an antiparallel β sheet consisting of four strands. The characteristic arrangement of these elements—an antiparallel beta sheet exposed to the protein surface onto the back side of which an alpha helix is packed which lies vertically on top of it—is generally considered as so-called ubiquitin-like folding motif. Therefore, ubiquitin is name-giving for the respective protein superfamily ("ubiquitin-like proteins") or the protein family ("ubiquitin-related proteins"), respectively, (Murzin et al., 1995) which comprises proteins such as for example SUMO-1 (Müller et al., 2001), FAU (Michiels et al., 1993), NEDD-8 (Kumar et al., 1993), UBL-1 (Jones and Candino, 1993), and GDX (Filippi et al., 1990) bearing this motif as well as a high degree of identity to ubiquitin in their primary sequence. Another structural feature is a marked hydrophobic region in the protein interior between the alpha helix and the beta sheet.

Because of its small size, the artificial preparation of ubiquitin can be carried out both by chemical synthesis and by means of biotechnological methods. Due to the favourable folding properties, ubiquitin can be produced by genetic engineering using microorganisms such as Escherichia coli in relatively large amounts either in the cytosol or in the periplasmic space. Because of the oxidizing conditions predominating in the periplasm the latter strategy generally is reserved for the production of secretory proteins. Due to the simple and efficient bacterial preparation ubiquitin can be used as a fusion partner for other foreign proteins to be prepared for which the production is problematic. By means of the fusion to ubiquitin an improved solubility and thereby an improved yield can be achieved. The approach practised in the present invention to provide ubiquitin as universal artificial binding protein allows for a completely novel utilization of its proteinchemical properties.

Among those proteins the natural function of which is utilized for artificial applications—for example in biotechnology, bioanalytics or medicine—antibodies (i.e. the immunoglobulins) play a predominant role. Their ability of specific, non-covalent binding to almost any possible substance makes them the most important tool for almost every bioscientific application which requires recognition, binding or separation of ligands, receptors or other target molecules. The methods developed in recent years for the functional biosynthesis of antibody fragments in E. coli have further extended the possibilities of use of immunoglobulins but have at the same time demonstrated their difficulties and limitations.

Besides $F_{ab}$- and $F_v$-fragments (Skerra and Plückthun, 1988) which principally can also be obtained by conventional proteinchemical methods different artificial constructs could be developed by means of methods of genetic engineering and due to the modular structure of immunoglobulins (reviewed in Dübel and Kontermann, 2001), notably single chain $F_v$ fragments (scFv) (Bird et al., 1988), disulfide-bridged $F_v$ fragments (dsFv) (Brinkmann et al., 1993) as well as bivalent (Carter et al., 1992) and bispecific antibody fragments (e.g. diabodies, Holliger et al., 1993). For diagnosis and the use in therapy bifunctional proteins can be obtained by genetic fusion of the recombinant Ig fragments to effector modules. Thus, fusions to alkaline phosphatase (Muller et al., 1999) and the green fluorescent protein (GFP; Griep et al., 1999) are available among others. Fusions of antibody fragments to radioisotopes or cytotoxic substances are of great potential importance for cancer treatment (immunotoxins; Reiter and Pastan, 1998). In this case, the selective binding of respective Ig fragments to specific surface proteins on tumor cells is utilized for the site-specific application of therapeutics (tumor targeting).

However, the methods for the preparation of antibody fragments in E. coli not only allow for their provision for diagnostics and therapy in sufficient quality and quantity but also for simple and quick modification of their protein- and immunochemical properties. The easy handling of a bacterial host enables a straightforward alteration of the vector-encoded genes for the foreign protein by means of standard molecular-biological methods. By means of a targeted antibody engineering (Kontermann and Dübel, 2001) antibody fragments can thus be optimised e.g. with respect to their binding affinity or their host compatibility. Also, specific antibodies or fragments thereof, respectively, can be prepared artificially, i.e. out of the immune system, which are directed against the most different target substances such as low molecular weight structures or proteins for example. By such evolutive methods synthetic libraries of antibody fragments are prepared by the introduction of random mutations which in their extent can be close to the human repertoire (Knappik et al., 2000). By means of suitable selection strategies such as phage display or ribosomal display (Winter, 1998, Hoogenboom et al., 1998;

Hanes et al., 2000) functional Ig fragments having the desired binding property are isolated in the case of success. In this manner it is also possible for example to obtain binding proteins for such antigens which during a classical immunization would provoke toxic effects or only a weak immune response.

Despite the above-mentioned achievements and possibilities provided by antibody engineering certain disadvantages can limit the practical use of antibodies. Thus, it is a problem to provide them in sufficient amounts: the production of functional antibodies is carried out in eukaryotic cell culture systems—an extraordinarily cost-intensive method. Furthermore, the low tissue penetration of the antibody molecules due to their size and their long residence time in the serum (slow blood clearance), respectively, hamper many therapeutic applications. Although smaller fragments of antibodies such as $scF_v$ or $F_{ab}$ fragments (see above) can be prepared in bacteria and thus basically at lower costs the yields of this recombinant production, however, are lower than the desired level due to their unfavourable folding properties and the required formation of several disulfide bonds. Moreover, recombinant antibody fragments often are less stable and show a lower binding activity as compared to the parental antibodies.

In order to circumvent such limitations attempts are made to impart the principle of antibody binding—namely the binding by means of a hypervariable surface-exposed region localized on a conserved protein scaffold—to other proteins (Skerra, 2000). This means that essentially variable loops are varied in order to generate an artificial binding property. For this purpose, usually natural binding proteins such as e.g. lipocalins (Beste et al., 1999) or the fibronectin type III domain (Koide et al., 1998) are used as a starting point for which binding sites are formed—in a manner analogously to antibodies—from flexible "loop" structures whose modification enables the recognition of ligands different from the natural ones.

Alternatively, according to WO 01/04144, in beta sheet structural proteins per se lacking a binding site this is artificially generated on the protein surface. By means of this de novo generated artificial binding site (see below) e.g. variations of γ-crystallin—an eye lens structural protein—can be obtained which interact with previously defined substances in quantifiable affinity and specificity. In contrast to the modification of binding sites which are already present and formed from flexible "loop" structures as exemplarily mentioned above these are generated de novo according to WO 01/04144 on the surface of beta sheets. However, WO 01/04144 only describes the alteration of relatively large proteins for the generation of novel binding properties. Due to their size the proteins according to WO01/04144 can be modified on the genetic engineering level only by methods which require some effort. Furthermore, in the proteins disclosed so far only a relatively small proportion by percentage of the total amino acids was modified in order to maintain the overall structure of the protein. Therefore, only a relatively small region of the protein surface is available which can be utilized for the generation of binding properties that did not exist previously. Moreover, on the experimental level WO 01/04144 discloses only the generation of a binding property to small, low molecular weight molecules but not to larger molecules such as e.g. proteins.

SUMMARY OF THE INVENTION

Therefore, it is an object of the present invention to provide proteins having novel binding affinities that did not exist previously to selected binding partners without showing the disadvantages described above. Another object of the present invention is to create substitutes molecules for antibodies which, however, do not show the above-mentioned disadvantages of antibodies.

According to the invention, this object is achieved by providing modified proteins according to claim 1 which are largely based on the protein structure of the starting protein, e.g. ubiquitin, and which carry an artificially generated binding site on their surface.

Particularly, according to the invention a protein is provided selected from the group consisting of proteins of the protein superfamily of "ubiquitin-like proteins", proteins having an ubiquitin-like folding motif as well as fragments or fusion proteins thereof each having the ubiquitin-like folding motif wherein due to one or more modifications of amino acids in at least one surface-exposed region of the protein including the at least one beta sheet strand of the beta sheet region and optionally non-beta sheet regions the protein shows a binding affinity with respect to a predetermined binding partner that did not exist previously while the ubiquitin-like folding motif is retained.

Thus, the invention relates to a protein modified by substitution, insertion, deletion, chemical modification or combinations thereof selected from the group consisting of proteins of the protein superfamily of "ubiquitin-like proteins", proteins having an ubiquitin-like folding motif as well as fragments or fusion proteins thereof each of which having an ubiquitin-like folding motif wherein the protein due to this modification shows a binding affinity with respect to a predetermined binding partner that did not exist previously obtainable by the following method:
 a) selecting a protein to be modified;
 b) determining a binding partner;
 c) selection of amino acids in at least one surface-exposed region of the protein including at least one beta sheet strand of the beta sheet region and optionally non-beta sheet regions;
 d) modifying the selected amino acids by substitution, insertion, deletion and/or chemical modification while the ubiquitin-like folding motif is retained;
 e) contacting the modified protein with the binding partner determined in step b);
 f) detecting those proteins having a binding affinity to the binding partner predetermined in step b).

Furthermore, it is an object of the present invention to provide respective methods for the preparation of the above-mentioned ubiquitin-based modified proteins and uses for these modified proteins.

Thus, the invention further describes a method for the preparation of a protein selected from the group consisting of proteins of the protein superfamily of "ubiquitin-like proteins", proteins having an ubiquitin-like folding motif as well as fragments or fusion proteins thereof each of which having an ubiquitin-like folding motif wherein due to one or more modifications the protein shows a binding affinity with respect to a predetermined binding partner that did not exist previously, obtainable by the following method:
 a) selecting a protein to be modified;
 b) determining a binding partner;
 c) selection of amino acids in a surface-exposed region of the proteins including at least one beta sheet strand of the beta sheet region and optionally non-beta sheet regions;
 d) modifying the selected amino acids, preferably by substitution, insertion, deletion and/or chemical modification while the ubiquitin-like folding motif is retained;

e) contacting the modified protein with the binding partner determined in step b);

f) detecting the proteins having a binding affinity with respect to the binding partner predetermined in step b).

Thus, the invention provides proteins or polypeptides, respectively, prepared by modification of proteins or polypeptides, respectively, having an ubiquitin-like folding motif as defined in the present application. These include the proteins of the protein superfamily of "ubiquitin-like-proteins", all proteins having an ubiquitin-like folding motif and fragments or fusion proteins of these proteins, with the proviso that they also have an ubiquitin-like folding motif. Starting from these proteins or polypeptides, respectively, one or more amino acids in the original protein or polypeptide, respectively, are modified. The modifications particularly comprise the substitution of amino acids, but also insertions and deletions of one or more amino acids as well as chemical modifications of amino acids. These modifications are performed in at least one surface-exposed region of the protein to be modified. The modification of at least one amino acid comprises at least one beta sheet strand of the beta sheet region wherein the beta sheet strand must be localized at the surface of the protein to be accessible for the binding partner o the ligand, respectively, able to bind to the modified protein with an affinity which can be determined. In another embodiment of the invention, in addition to the alterations in the beta sheet strand of the beta sheet region also non-beta sheet regions are modified which preferably are surface-exposed in order to affect, particularly to increase, the binding affinity with respect to the predetermined binding partner and thus to enhance the specificity.

Different techniques known per se for the modification of one or more amino acids are available to those skilled in the art. These will be described in more detail in the following. In addition, reference is made to the publications of Ausuebel et al., 1994, as well as Sambrook et al., 1989.

Modifications of amino acids of the non-surface-exposed core region of ubiquitin are already known (Finucane et al., Biochemistry, vol. 38, No. 36, 1999 or Lazar et al., Protein Science (1997), 6: 1167-1178). The alterations made therein are directed to positions not involved in binding which due to their localization within the hydrophobic core are not accessible to the solvent or to possible binding partners.

In the following, the meaning of the term "binding property that did not exist previously" and de novo generated artificial binding site, respectively, in the context of this invention shall be explained. These terms mean that the modified protein previously shows no binding property to a predetermined binding partner or to a natural binding partner of ubiquitin in the modified region. In another embodiment of the invention the proteins to be modified are selected to have no binding affinity to the predetermined binding partner. The binding partners which can also be defined as ligands have a measurable affinity to the protein modified according to the invention. As a minimal value for the presence of a quantifiable binding property, i.e. the affinity with which the partner is bound, can be considered according to the invention a dissociation constant for the complex formed of $K_D = 10^{-5}$ M or smaller. A value of $10^{-5}$ M and below can be considered as a quantifiable binding affinity. Depending on the application a value of $10^{-6}$ M to $10^{-12}$ M is preferred, further preferably $10^{-7}$ to $10^{-11}$ M for e.g. chromatographic applications or $10^{-9}$ to $10^{-12}$ M for e.g. diagnostic or therapeutic applications. Further preferred binding affinities are in the range of $10^{-7}$ to $10^{-10}$ M, preferably to $10^{-11}$ M. The methods for the determination of the binding affinities are known per se and are further described on the following pages.

Modification according to the invention is intended to mean substitutions of amino acids, insertions, deletions or chemical modifications.

As the proteins to be modified according to the invention proteins of the superfamily of "ubiquitin-like proteins" can be used. According to the invention, this superfamily comprises the subgroups listed in Murzin et al. (1995). These include for example the protein families of "ubiquitin-related proteins", "UBX domain", GABARAP-like", RAS-binding domain", etc. Preferably, proteins of the protein family of "ubiquitin-related proteins" are used. According to the invention also those proteins are comprised which have an ubiquitin-like folding motif. Examples of these are SUMO-1, FAU, NEDD-8, UBL-1, and GDX as well as Rub1, APG8, ISG15, URM1, HUB1, elongin B, PLIC2 (N-terminal domain), human parkin (N-terminal domain).

The proteins which may be used according to the invention from the superfamily of ubiquitin-like proteins have been characterized to a high extent. Only be way of example reference is made to the "Structural Classification of Proteins" database, which is available from the website of the Laboratory of Molecular Biology of the Medical Research Council (MRC-LMB; Cambrige, United Kingdom). According to this site, the family of ubiquitin-like proteins is defined as a superfamily to which the family of ubiquitin-related proteins belongs. All members of this superfamily are characterized primarily by β sheets arranged in an antiparallel manner and subdivided into α and β segments. The folding is defined as beta-Grasp and thus as ubiquitin-like. The core region is defined as follows: beta(2)-alpha-beta(2) wherein the numbers indicate the number of strands and the totality of strands forms the β sheet. The arrangement of the mixed beta sheet is 2143 meaning the position of the strands if the sheet is seen from the top from left to right (amino terminus at the bottom, carboxy terminus on top). A characteristic of the members of the ubiquitin-like proteins thus is an antiparallel β sheet exposed to one surface of the protein onto the back side of which an α helix is packed which lies perpendicularly on top of it. This ubiquitin-like folding motif is a characteristic of the proteins which can be used and modified according to the invention and clearly distinguishes the members of the family from other proteins. In view of this definition, also the ubiquitin-like N-terminal domain of PLIC-2 and the ubiquitin-like domain of parkin are comprised by the invention.

Those skilled in the art can preliminarily judge either with respect to sequence comparisons, so-called alignments, or by structural considerations whether the proteins are a member of the protein superfamily of ubiquitin-like proteins or not. Naturally, the last evidence is always provided by a structural analysis, for example a structural analysis by X-ray crystallography or multidimensional nuclear magnetic resonance spectroscopy. In recent times, also structural analysis using genetic algorithms can provide good predictions.

Further information with respect to the ubiquitin superfamily can be found for example in the publication of Larsen et al., 2002. In addition, reference is also made to the publication by Buchberger et al., 2001. Buchberger describes the typical β Grasp fold as a characteristic of ubiquitin-like proteins having a secondary structure of the organization beta-beta-alpha-beta-beta-alpha-beta, i.e. an arrangement of five beta-strands in the form of a "mixed sheet" in an arrangement of 21534. In this respect, it has to be pointed out that UBX has no significant homology in its primary sequence to e.g. ubiquitin (Buchberger et al., 2001) but in spite of this fact—due to its three-dimensional structure which is identical to that of e.g. ubiquitin—is classified as an ubiquitin-like protein. In this respect it shall be mentioned that in ubiquitin also the amino acids at positions 48 and 49 are sometimes regarded as an extra beta strand (Vijay-Kumar, 1987). This fifth strand which in the ubiquitin structure would be localized behind the helix and give an arrangement of 21534 to the "mixed sheet", however, consists of only two amino acids, and it can be really doubted whether this strand of two amino acids can be called a beta sheet strand or not. As explained above, however, according to Buchberger et al. (2001) it is possible to classify also proteins having an arrangement of 21534 without any problems into the superfamily of ubiquitin-like proteins. For the present invention the definition 2143 described in more detail above was selected for the arrangement of beta strands in ubiquitin.

The proteins of the above-mentioned family and superfamily usually are highly conserved. According to present knowledge, ubiquitin for example has an identical amino acid sequence in all mammals. Ubiquitin of yeast differs only in three amino acids from this sequence. Human ubiquitin or ubiquitin of mammals, respectively, consists of 76 amino acids and has the structure described in the beginning.

According to the invention, the modified protein should have at least 30%, preferably at least 40% or 50%, further preferably at least 60%, at least 70%, at least 80%, at least 90%, or at least 95% identity in its amino acid sequence to the starting protein which is modified, for example to human ubiquitin wherein the protein in any case has an ubiquitin-like folding motif as defined in detail above.

According to the invention, also fragments of the proteins mentioned are comprised as long as they comprise the ubiquitin-like folding motif described above, as well as fusions of the proteins mentioned to other proteins. In the case of such fragments and fusion proteins, amino acid positions mentioned in the frame of the invention shall always refer to the respective position in human ubiquitin. Examples of fusion partners are (reporter) enzymes, toxins or other binding proteins etc. Furthermore, chemical coupling for example to low molecular weight substances such as biotin, digoxigenin, fluorescent and/or luminescent substances etc. can be performed.

In the case of fusion proteins an already fused protein can be modified according to the invention. It is also comprised by the invention, however, that a segment is fused following modification or selection. In each case this can be done according to methods known to those skilled in the art.

According to the present invention, the protein selected for the preparation of the modified protein preferably is human ubiquitin or ubiquitin of another origin, for example another mammalian ubiquitin. Therefore, the invention will be described in the following using particularly human ubiquitin as an example. The modification of human ubiquitin will be described with respect to several examples to obtain a protein which also can be referred to as mutein and which shows a binding affinity with respect to a predetermined binding partner that did not exist previously. As the mammalian ubiquitins there can be particularly used ubiquitins of rodents, domestic animals and agricultural animals among the field of mammals. If the field of use of the proteins prepared according to the invention is known, i.e. if the modified protein shall be for example used as a pharmaceutical composition for the treatment of diseases in humans a human protein can be preferably used as starting protein to be modified; this applies to corresponding fields of use as well. It shall be pointed out that the explanations given below are based on human ubiquitin only by way of example. On the basis of this detailed specification and the examples mentioned it will be possible for those skilled in the art to modify further proteins having ubiquitin-specific folding motifs according to the invention. Thus, the invention is not limited to human ubiquitin or to ubiquitin in general. Indications and explanations in this respect shall be considered as exemplary embodiments of the invention which, however, are particularly preferred.

As mentioned above, human and mammalian ubiquitin, respectively, has 76 amino acids. The amino acids of the four beta strands which contribute to the formation of the antiparallel beta sheet are according to the invention and according to the structure 1UBQ in the Protein Data Bank (PDB) data base available on the World Wide Web:

First strand (aminoterminal): 2 to 7; second beta sheet strand: 12 to 16; third strand: 41 to 45; fourth strand (carboxyterminal): 66 to 71. The position of the strands if the sheet is viewed from the top (amino terminus at the bottom, carboxy terminus on top) from left to right is: 2nd, 1st, 4th, 3rd strand wherein the polypeptide chain between the 1st and 4th strand forms the alpha helix.

Selection and Modification of the Amino Acids to be Modified:

On the basis of corresponding structural data such as for example those freely available in the PROTEIN DATA BANK™ (Berman et al., 2000; see also the website of the RCSB on the World Wide Web) the positions of those amino acids in the starting protein, e.g. in the ubiquitin protein scaffold, whose side chains are surface-exposed, i.e. directed towards the solvent or a potential binding partner, can be localized by means of computerized analysis. Furthermore, those amino acids in the starting protein, e.g. in ubiquitin, whose random substitution presumably would have no or only a slightly negative effect on the stability of the protein scaffold can be identified by computerized analysis. This information can provide a first indication as to the suitability of every single amino acid as an element of a binding site and would then require further experimental verification. In a preferable embodiment of the present invention for example the amino acids at positions 2, 4, 6, 62, 63, 64, 65, and 66 in human ubiquitin were selected due to their surface-exposition and the tolerance of the overall structure to their random substitution. The positions mentioned are localized in spatial proximity to each other at the beginning of the first aminoterminal beta sheet strand (pos. 2, 4, 6) as well as in the loop (Pos. 62, 63) or at the beginning of the carboxyterminal beta sheet strand (Pos. 64, 65, 66), respectively, and form with their amino acid side chains a contiguous region on the surface of ubiquitin (FIG. 1). By means of random amino acid substitutions ("randomization") in the region analyzed there can thus be generated—in a manner analogous to the antigen binding site of antibodies—a hypervariable surface-exposed region on the otherwise intact protein structure of ubiquitin.

Using the ProSAII software ("Protein Structure Analysis"; Proceryon Biosciences, Salzburg) the protein stability could be determined for example for $10^4$ variations compared to ubiquitin (WT) and the same number of randomly taken samples of variations in which the residues of a "control epitope" (randomized positions 24, 28, 31, 32, 35, 37, 38, 39) were substituted. In this case about 19% of the variations generated in silico which were randomly substituted in the region of the binding site have a stability which is at least as high as that of ubiquitin (WT) while about 90% are more stable than those carrying the "control epitope" (FIG. 2). This computer-based result can then be used as a basis for the selection of suitable amino acids.

According to a preferred embodiment—starting from the available structural data of human ubiquitin—eight amino acid positions in the region of the binding site to be generated were selected first. By means of random alterations of the primary sequence in this region (random mutagenesis) and subsequent specific selection those variations were obtained which showed the desired binding activity with respect to a predetermined hapten or antigen or to a predetermined binding partner in general, respectively. Although a de novo binding property is conferred to the modified proteins obtained in this manner they remain to a high degree identical in structure and proteinchemical properties to the starting protein. Therefore, they provide advantages such as e.g. small size, high stability, cost-effective preparation as well as easy modification together with high affinity and specificity for a previously defined ligand. In this respect, the suitability of ubiquitin as a scaffold structure for the generation of artificial binding proteins could not be expected since 1) the tolerance of the scaffold to the extensive amino acid substitutions could not be expected because of the small size of ubiquitin and 2) the functionality of the artificial binding site involving the beta sheet which is considered as rigid and inflexible did not seem possible beforehand.

According to the invention, antigen shall refer to a substance bound by an antibody. The term antigen comprises haptens, peptides, proteins, sugars, DNA etc. From the Roche Lexikon Medizin, 4th edition; available on the World Wide Web) the following definition of antigen and hapten can be obtained which is also used for the present invention:

Antigen (AG): Designation for any substance recognized as foreign ("not self") by the immune system. Initiates in most case an immune reaction leading to immunity (="immunogen"); in the case of allergy (="allergen") and atopy ("atopigen"), respectively, this immune reaction is exaggerated. The AG induces a humoral (antigen-antibody reaction) and/or cellular defence reaction (see below immunity). If the AG is tolerated by the immune system (immune tolerance) it is also referred to as a "tolerogen". Effective as an antigen are mainly complex and higher molecular weight substances (protein bodies, polysaccharides, nucleotides and many synthetic compounds) having chemically identifiable functionalities (determinant) responsible for the immune response. Classified as 1) complete AG, mostly of higher molecular weight and able to arise an immune reaction by itself, 2) as a low molecular weight hapten (=half antigen) which acts as an immunogen only after it is coupled to a larger carrier molecule. Referred to e.g. as xeno-, allo- or isogenic, autologous AG; auto-, hetero, transplantation, anti-tumor virus AG.

Hapten: simple, low molecular weight chemical compound responsible for the specificity of an antigen (AG) or capable of specific binding of the antibody due to its structure (determinant), respectively, but unable to generate an allergy in contrast to a complete AG. Becomes a complete antigen (antigen) after binding to a protein body called carrier.

It shall be pointed out that using the present invention it is also possible to generate variations of ubiquitin which have a binding property with respect to non-immunogenic substances as binding partners, such as e.g. tumor markers.

In a preferable embodiment of the present invention a modification, preferably a substitution, is carried out at least partially at two or more amino acids directly adjacent in the primary sequence wherein the amino acids directly adjacent to each other in the tertiary structure furthermore preferably are localized at least partially in a beta sheet strand of the protein. In general, every substitution of an amino acid in a protein is accompanied by a degradation of the stability of the protein. Single substitutions can mostly be tolerated due to the influence of adjacent amino acids without extensive destabilizations. However, if a whole region, i.e. for example a structural entity consisting of several adjacent amino acids, is changed a stabilizing effect due to the directly adjacent amino acids can no longer be expected. Accordingly, up to now only amino acids of ubiquitin were modified in the prior art which were not directly adjacent to each other. It was surprising that after such wide-ranging alterations of regions of the protein by modification of directly adjacent amino acids the stability of the protein was not substantially degraded. The fact alone that two directly adjacent amino acids in ubiquitin or proteins with ubiquitin-like folding motif can be substituted without negatively affecting the stability and structure of the protein was surprising and could not be expected.

Particularly in the case of the relatively small ubiquitin the modification of directly adjacent amino acids furthermore has the advantage that it is easier to prepare a modification of this type by genetic engineering than in the case of amino acids which are not directly adjacent to each other. Thus, according to this embodiment the simplified generation of a large number of modified proteins can be provided both on the protein and on the DNA level.

Preferably, the number of substitutions of directly adjacent amino acids is 2 to 10, more preferably 2 to 8 amino acids directly adjacent to each other in the primary sequence, further preferably 3 to 7 or 4 to 6 amino acids directly adjacent to each other in the primary sequence.

If amino acids directly adjacent to each other in the primary sequence are substituted a portion of these amino acids can extend into the region of a beta sheet strand. This portion extending into the region of a beta sheet strand can have a length of two or more amino acids, preferably two or three amino acids. The region of directly adjacent amino acids thus is at the beginning or at the end of a beta sheet strand region which preferably has a length of about 2 to 3 amino acids.

In a further preferred embodiment 5 or more directly adjacent amino acids are modified, preferably substituted, wherein two or more, preferably two or three, directly adjacent amino acids form the beginning or the end of a beta sheet strand region. In this case, preferably 8, 9 or 10 amino acids, particularly preferably 8 amino acids can be regarded as an upper limit for the total number of directly adjacent modified amino acids.

In the case of the modification of directly adjacent amino acids in a beta sheet strand of ubiquitin these amino acids generally are all surface-exposed if these amino acids are at the beginning or the end of a beta sheet strand. In this case it can be assumed that all amino acids are involved in the generation of the novel binding property.

In a preferred embodiment of the present invention those amino acids are modified for the generation of a region having the novel binding properties which form a contiguous region on the surface of the protein. In this manner, a contiguous region can be generated which has a binding property that did not exist previously. "Contiguous region" according to the invention refers to the following: due to the charge, the spatial structure and the hydrophobicity/hydrophilicity of their side chains amino acids interact with their environment in the corresponding manner. The environment can be the solvent, generally water, or other molecules, e.g. spatially close amino acids. By means of the structural information about the protein as well as the respective software the surface of the proteins can be characterized. For example, the interface region between the atoms of the protein and the solvent can be visualized in this way including the information about how this interface region is structured, which surface areas are accessible to the solvent or how the charges are distributed on the surface. A contiguous region can be revealed for example by visualization of this type using a suitable software. Such methods are known to those skilled in the art. According to the invention, basically also the whole surface-exposed region can be used as the contiguous region on the surface to be modified for the generation of novel binding properties. Preferably, for this purpose a modification can also comprise the α-helical region.

The modification of amino acids in at least one surface-exposed region of the protein comprising at least one β sheet strand of the β sheet region is crucial. The beta sheet structure is defined by being essentially sheet-like and almost completely stretched. In contrast to alpha helices which are formed from a uninterrupted segment of the polypeptide chain, beta sheets can be formed by different regions of the polypeptide chain. In this way, regions spaced further apart in the primary structure can get into close proximity with each other. A beta strand typically has a length of 5-10 amino acids and has an almost completely stretched conformation. The beta strands come so close to each other that hydrogen bonds form between the C=O group of one strand and the NH group of the other strand and vice versa. Beta sheets can be formed from several strands and have a sheet-like structure wherein the position of the C alpha atoms alternates between above or below the sheet-like plane. The amino acid side chains follow this pattern and, thus, alternatively point towards the top or towards the bottom. Depending on the orientation of the beta strands the sheets are classified into parallel and antiparallel sheets. According to the invention both can be mutated and used for the preparation of the proteins claimed.

For the mutagenesis of the beta sheet structure those beta sheet regions are selected in the protein which are close to the surface. Surface-exposed amino acids can be identified with respect to the available x-ray crystallographic structure. If no crystal structure is available attempts can be made by means of computer analysis to predict surface-exposed beta sheet regions and the accessibility of individual amino acid positions with respect to the available primary structure (see e.g., the "PredictProtein" website on the World Wide Web) or to model the 3D protein structure (see e.g., the SWISS-MODEL section of the EXPASY website on the World Wide Web) and to obtain information about potential surface-exposed amino acids in this manner.

It is also possible, however, to carry out mutageneses in the beta sheet for which the time-consuming pre-selection of amino acid positions to be mutagenized can be omitted. Those DNA regions encoding the beta sheet structures are isolated from their DNA environment, subjected to random mutagenesis and are afterwards re-integrated into the DNA coding for the protein from which they were removed previously. This is followed by a selection process for mutants with the desired binding properties.

In another embodiment of the invention the beta sheet regions close to the surface are selected as already detailed above and the amino acid positions to be mutagenized within these selected regions are identified. The amino acid positions selected in this way can then be mutagenized on the DNA level either by site-directed mutagenesis, i.e. a codon coding for a specific amino acid is substituted by a codon encoding another previously selected specific amino acid, or this substitution is carried out in the context of a random mutagenesis wherein the amino acid position to be substituted is established but not the codon encoding the novel, not yet determined amino acid.

Surface-exposed amino acids are accessible to the surrounding solvent. If the accessibility of the amino acids in the protein is more than 8% compared to the accessibility of the amino acid in the model tripeptide Gly-X-Gly, the amino acids are called surface-exposed. These protein regions or individual amino acid positions, respectively, are also preferred binding sites for possible binding partners for which a selection shall be carried out according to the invention. In addition, reference is made to Connolly et al., 1983, and Shrake et al., 1973, which for complete disclosure are incorporated by reference in this application.

Variations of ubiquitin protein scaffold differing by amino acid substitutions in the region of the de novo generated artificial binding site from the parental protein and from each other can be generated by a targeted mutagenesis of the respective sequence segments. In this case, amino acids having certain properties such as polarity, charge, solubility, hydrophobicity or hydrophilicity can be replaced or substituted, respectively, by amino acids with respective other properties. Besides substitutions, the term "mutagenesis" comprises also insertions and deletions. On the protein level the modifications can also be carried out by chemical alteration of the amino acid side chains according to methods known to those skilled in the art.

As a starting point for the mutagenesis of the respective sequence segments can serve for example the cDNA of an ubiquitin-like protein which can be prepared, altered, and amplified by methods known to those skilled in the art. For site-specific alteration of ubiquitin in relatively small regions of the primary sequence (about 1-3 amino acids) commercially available reagents and methods are on hand ("Quick Change", Stratagene; "Mutagene Phagemid in vitro Mutagenesis Kit", Biorad). For the site-directed mutagenesis of larger regions specific embodiments of e.g. the polymerase chain reaction (PCR) are available to those skilled in the art. For this purpose a mixture of synthetic oligodeoxynucleotides having degenerated base pair compositions at the desired positions can be used for example for the introduction of the mutation. This can also be achieved by using base pair analogs which do not naturally occur in genomic DNA, such as e.g. inosine.

Starting point for the mutagenesis of one or more β sheet strands of the β sheet region as well as optionally the non-β sheet region can be for example the cDNA of an ubiquitin-like protein or also the genomic DNA. Furthermore, the gene coding for the protein can also be prepared synthetically.

Different methods known per se are available for mutagenesis which are methods for site-specific mutagenesis, methods for random mutagenesis, mutagenesis using PCR or comparable methods.

In a preferred embodiment of the invention the amino acid positions to be mutagenized are predetermined. The selection of amino acids to be modified is carried out either depending on the protein to be modified and/or depending on the selected binding partner. In each case, a library of different mutants is generally established which is screened using methods known per se. Naturally, a pre-selection of the amino acids to be modified can be particularly easily performed if sufficient structural information is available for the protein to be modified. However, also without such structural information using methods employing random mutagenesis and subsequent selection it is possible to change the protein having the ubiquitin-like folding motif to adopt a binding affinity to the predetermined ligand or binding partner, respectively.

Methods for the targeted mutagenesis as well as mutagenesis of longer sequence segments, for example by means of PCR, by chemical mutagenesis or using bacterial mutator strains also belong to the prior art and can be used according to the invention.

In one embodiment of the invention the mutagenesis is carried out by assembly of DNA oligonucleotides carrying the amino acid codon NNK. It should be understood, however, that also other codons (triplefts) can be used.

The mutations are performed in a way that the beta sheet structure is maintained. Generally, the mutagenesis takes place on the outside of a stable beta sheet region exposed on the surface of the protein. It comprises both site-specific and random mutagenesis. Site-specific mutageneses comprising a relatively small region in the primary structure (about 3-5 amino acids) can be generated with the commercially available kits of Stratagene (QuickChange) or Bio-Rad (Mutagene phagemid in vitro mutagenesis kit) (cf. U.S. Pat. No. 5,789,166; U.S. Pat. No. 4,873,192).

If more extended regions are subjected to site-specific mutagenesis a DNA cassette must be prepared wherein the region to be mutagenized is obtained by the assembly of oligonucleotides containing the mutated and the unchanged positions (Nord et al., 1997; McConell and Hoess, 1995). Random mutageneses can be introduced by propagation of the DNA in mutator strains or by PCR amplification (error-prone PCR) (e.g. Pannekoek et al., 1993). For this purpose, a polymerase with an increased error rate is used. To enhance the degree of the mutagenesis introduced or to combine different mutations, respectively, the mutations in the PCR fragments can be combined by means of DNA shuffling (Stemmer, 1994). A review of these mutagenesis strategies with respect to enzymes is provided in the review of Kuchner and Arnold (1997). To carry out this random mutagenesis in a selected DNA region also a DNA cassette must be constructed which is used for mutagenesis.

Random substitution of amino acids according to one example of the present invention at positions 2, 4, 6, 62, 63, 64, 65, and 66 of ubiquitin can be performed particularly easily by means of PCR since the positions mentioned are localized close to the amino or the carboxy terminus of the protein. Accordingly, the codons to be manipulated are at the 5' and 3' end of the corresponding cDNA strand. Thus, the first oligodeoxynucleotide used for a mutagenic PCR reaction—apart from the codons at positions 2, 4, and 6 to be mutated—corresponds in sequence to the coding strand for the amino terminus of ubiquitin. Accordingly, the second oligodeoxynucleotide—apart from the codons of positions 62, 63, 64, 65, and 66 to be mutated—at least partially corresponds to the non-coding strand of the polypeptide sequence of the carboxy terminus. By means of both oligodeoxynucleotides a polymerase chain reaction can be performed using the DNA sequence encoding the ubiquitin protein scaffold as a template.

Furthermore, the amplification product obtained can be added to another polymerase chain reaction using flanking oligodeoxynucleotides which introduce for example recognition sequences for restriction endonucleases. After hydrolysis with the appropriate restriction endonucleases the synthetic DNA molecules obtained can be ligated, i.e. linked, to the nucleic acid sequences of e.g. cloning or expression vectors which were prepared accordingly. Such procedures and systems are known to those skilled in the art. Those systems are e.g. commercially available from Novagen (Madison, Wis.), IBA (Göttingen) or New England Biolabs (Beverly, Mass.): It is preferred according to the invention to introduce the gene cassette obtained into a vector system suitable for use in the subsequent selection procedure for the isolation of ubiquitin variations having binding properties to a predetermined hapten or antigen.

According to a preferable embodiment of the present invention only amino acid positions are modified for the generation of a novel binding property which do not belong to regions which in unmodified ubiquitin are involved in linkages to natural binding partners of ubiquitin. This ensures that not only already present binding properties of ubiquitin are altered.

The regions for modification can be basically selected as to whether they can be accessible for a possible binding partner and whether the overall structure of the protein will presumably show tolerance to a modification.

In the protein, preferably ubiquitin from mammals, at least 15% of the amino acids present in beta strands, preferably at least 20%, further preferably at least 25%, can be modified, preferably substituted, according to the present invention to generate a binding property that did not exist previously. At a maximum preferably about 40% of the amino acids present in beta strands, further preferably at a maximum about 35% and even more preferably about 30% are modified, preferably substituted.

According to an Example of the present invention for example 6 of the 24 amino acids present in beta strands were modified to generate a binding property to a predetermined binding partner. The selection of a larger number of amino acids for modifications provides for the possibility to generate a larger library of proteins with binding affinity so that the possibility that one of these modified proteins has a quantifiable and/or high binding affinity with respect to a predetermined binding partner is increased.

Furthermore, besides a modification in beta strands also a modification in other surface-exposed regions of the protein can be carried out, preferably for example in loop regions. Besides the modified regions in the beta strands these modified regions can also be involved in the newly generated binding.

According to another preferred embodiment of the present invention at least 6, preferably at least 8, surface-exposed amino acids of an ubiquitin, preferably mammalian or human ubiquitin, can be modified wherein a substitution is preferred as the modification. These at least 6 surface-exposed modified amino acids then form the region with binding affinity to the predetermined binding partner. In this respect, it is particularly preferred that at least 4, preferably at least 6, further preferably at least 8 of the surface-exposed amino acids are in a beta sheet region, i.e. in a beta sheet strand or distributed on several beta strands. It is further preferred that at least 5 of the modified, preferably substituted, amino acids are directly adjacent to each other in the primary sequence.

In another preferred embodiment of the present invention amino acids in at least two, preferably exactly two, of the four beta strands in the protein are modified to generate a novel binding property. Also preferable is a modification in three or four of the four beta strands for the generation of a binding property that did not exist previously with respect to a selected binding partner.

It is particularly preferred that amino acids in the amino-terminal and carboxyterminal strand are modified, preferably substituted, to generate novel binding properties. In this respect, it is further preferably that amino acids in the loop adjacent to the carboxyterminal beta sheet strand are modified, preferably substituted, in addition.

Particularly preferred is a modification, preferably a substitution, at the following positions of a mammalian ubiquitin, preferably human ubiquitin: 2, 4, 6, 62, 63, 64, 65, 66. These amino acids form a contiguous surface-exposed region on the surface of ubiquitin which was found to be particularly suitable for the generation of modified proteins having a binding affinity that did not exist previously with respect to a binding partner.

The substitution of amino acids for the generation of novel binding properties can be performed according to the invention with any desired amino acid, i.e. if the modification is carried out for the generation of novel binding properties it is not necessary to take care that the amino acids have a chemical property or a side chain, respectively, which is similar to that of the amino acids substituted so that any amino acid desired can be used for this purpose.

According to this invention as the proteins which are modified for the generation of binding affinities that did not exist previously with respect to selected binding partners can show other modifications such as substitutions, insertions, deletions and/or chemical modifications to switch off or newly add biological and/or proteinchemical functions of the protein already prior to this modification. Thus, the binding properties of ubiquitin to its natural binding partners can be switched off for example.

Thus, in one embodiment of the present invention a variation of human ubiquitin was used wherein the amino acid phenylalanine at position 45 was substituted by tryptophane. In this way, a protein could be provided which due to the substitution has improved spectroscopic properties compared to ubiquitin while the structure and stability of ubiquitin were maintained.

In another embodiment of the present invention positions 44, 48, 54, 70, 72, and 75 were substituted and amino acid 76 was deleted in human ubiquitin for example. In this way, a protein could be provided which can no longer perform the natural functions of ubiquitin while the structure and stability of ubiquitin were maintained.

If an already pre-modified ubiquitin of this type is used to generate binding properties that did not exist previously, in the end a ubiquitin is preferably obtained wherein in total at least 10, preferably at least 15 amino acids of the wild-type ubiquitin or generally of a mammalian ubiquitin are substituted. According to an Example, a modified ubiquitin could be obtained in this manner having 14 substitutions and a deletion while its original structure was maintained. Based on the total number of amino acids of ubiquitin this corresponds to a percentage of about 20%. This was extraordinarily surprising and could not be expected since usually a much lower percentage is already sufficient to disturb the folding of the protein.

The step of modification of the selected amino acids is performed according to the invention preferably by mutagenesis on the genetic level by random mutagenesis, i.e. a random substitution of the selected amino acids. Preferably, the modification in step d) is carried out by means of methods of genetic engineering for the alteration of a DNA belonging to the respective protein. Preferably, the expression of the protein is then carried out in prokaryotic or eukaryotic organisms.

According to the invention, a modified protein can further preferably be prepared by chemical synthesis. In this embodiment the steps c) to d) of claim 1 are then performed in one step.

Selection and Determination, Respectively, of the Amino Acids with Binding Affinity with Respect to a Predetermined Binding Partner:

After a protein library has been established by modification of selected amino acids the modified proteins are contacted according to the invention with a predetermined binding partner to optionally enable binding of the partners to each other if a binding affinity does exist.

Contacting according to the invention is preferably performed by means of a suitable presentation and selection method such as the phage display, ribosomal display, mRNA display or cell surface display, yeast surface display or bacterial surface display methods, preferably by means of the phage display method. For complete disclosure, reference is made also to the following references: Hoess, Curr. Opin. Struct. Biol. 3 (1993), 572-579; Wells and Lowmann, Curr. Opin. Struct. Biol. 2 (1992), 597-604; Kay et al., Phage Display of Peptides and Proteins—A Laboratory Manual (1996), Academic Press. The methods mentioned above are known to those skilled in the art and can be used according to the invention including modifications thereof.

The determination whether the modified protein has a quantifiable binding affinity with respect to a predetermined binding partner can be performed according to the invention preferably by one or more of the following methods: ELISA, plasmon surface resonance spectroscopy, fluorescence spectroscopy, FACS, isothermal titration calorimetry and analytical ultracentrifugation.

A type of the phage display procedure adapted to this application is described in the following as an example for a selection procedure according to the invention with respect to variations of ubiquitin which show binding properties. In the same manner e.g. methods for the presentation on bacteria (bacterial surface display; Daugherty et al., 1998) or yeast cells (yeast surface display; Kieke et al., 1997) or cell-free selection systems such as the ribosome display (Hanes and Plückthun, 1997; He and Taussig, 1997) or the cis display (Odegrip et al., 2003) or the mRNA display can be applied. In the latter case a transient physical linkage of genotype and phenotype is achieved by coupling of the protein variation to the appropriate mRNA via the ribosome.

In the phage display procedure described herein recombinant variations of ubiquitin are presented on filamentous phage while the coding DNA of the presented variation is present at the same time packed in a single-stranded form in the phage envelope. Thus, in the frame of an affinity enrichment variations having certain properties can be selected from a library and their genetic information can be amplified by infection of suitable bacteria or added to another cycle of enrichment, respectively. Presentation of the mutated ubiquitin on the phage surface is achieved by genetic fusion to an aminoterminal signal sequence—preferably the PelB signal sequence—and a capsid or surface protein of the phage—preferred is the carboxyterminal fusion to the capsid protein pIII or a fragment thereof. Furthermore, the encoded fusion protein can contain further functional elements such as e.g. an affinity tag or an antibody epitope for detection and/or purification by affinity chromatography or a protease recognition sequence for specific cleavage of the fusion protein in the course of the affinity enrichment. Furthermore, an amber stop codon can be present for example between the gene for the ubiquitin variation and the coding region of the phage capsid protein or the fragment thereof which is not recognized during translation in a suitable suppressor strain partially due to the introduction of one amino acid.

The bacterial vector suitable for the selection procedure in the context of the isolation of ubiquitin variations with binding properties to a predetermined hapten or antigen and into which the gene cassette for the fusion protein described is inserted is referred to as phasmid. Among others, it contains the intergenic region of a filamentous phage (e.g. M13 or f1) or a portion thereof which in the case of a superinfection of the bacterial cell carrying the phagemid by means of helper phages such as e.g. M13K07 results in the packaging of a closed strand of phasmid DNA into a phage capsid. The phagemids generated in this manner are secreted by the bacterium and present the respective ubiquitin variation encoded—due to its fusion to the capsid protein pIII or the fragment thereof—on their surface. Native pIII capsid proteins are present in the phagemid so that its ability to re-infect suitable bacterial strains and therefore the possibility to amplify the corresponding DNA is retained. Thus, the physical linkage between the phenotype of the ubiquitin variation—i.e. its potential binding property—and its genotype is ensured. In the present Example, the phasmid pMUBI-1 (FIG. 3) which has been constructed for this purpose is used for the insertion of the coding sequences of ubiquitin variations and for the preparation of phagemids.

Phasmids obtained can be selected with respect to the binding of the ubiquitin variation presented thereon to predetermined haptens or antigens by means of methods known to those skilled in the art. For this purpose, the presented ubiquitin variations can be transiently immobilized to target substance bound e.g. on microtiter plates and can be specifically eluted after non-binding variations have been separated. The elution is preferably performed by basic solutions such as e.g. 100 mM triethylamine. Alternatively, the elution can be performed under acidic conditions, by proteolysis or direct addition of infected bacteria. The phagemids obtained in this manner can be re-amplified and enriched by successive cycles of selection and amplification of ubiquitin variations with binding properties to a predetermined hapten or antigen.

Further characterization of the ubiquitin variations obtained in this way can be performed in the form of the phagemid, i.e. fused to the phage, or after cloning of the corresponding gene cassette into a suitable expression vector in the form of a soluble protein. The appropriate methods are known to those skilled in the art or described in the literature. The characterization can comprise e.g. the determination of the DNA sequence and thus of the primary sequence of the variations isolated. Furthermore, the affinity and specificity of the variations isolated can be detected e.g. by means of immunological standard methods such as ELISA or plasmon surface resonance spectroscopy, fluorescence spectroscopy, FACS, isothermal titration calorimetry or analytical ultracentrifugation. In view of the stability analysis, for example spectroscopic methods in connection with chemical or physical unfolding are known to those skilled in the art.

In the also used ribosomal display procedure variations of ubiquitin are prepared by means of a cell-free transcription/translation system and presented as a complex with the corresponding mRNA as well as the ribosome. For this purpose, a DNA library as described above is used as a basis in which the genes of variations are present in form of fusions with the corresponding regulatory sequences for expression and protein biosynthesis. Due to the deletion of the stop codon at the 3' end of the gene library as well as suitable experimental conditions (low temperature, high $Mg^{2+}$ concentration) the ternary complex consisting of the nascent protein, the mRNA and the ribosome is maintained during in vitro transcription/translation.

These complexes can be selected with respect to the binding of the ubiquitin variation presented thereon to predetermined haptens or antigens by means of methods known to those skilled in the art. For this purpose, the ubiquitin variations presented on the ribosomal complexes can be transiently immobilized to target substance bound e.g. on microtiter plates or can be bound to magnetic particles after binding in solution, respectively. Following separation of non-binding variations the genetic information of variations with binding activity can be specifically eluted in the form of the mRNA by destruction of the ribosomal complex. The elution is preferably carried out with 50 mM EDTA. The mRNA obtained in this manner can be isolated and reverse transcribed into DNA using suitable methods (reverse transcriptase reaction), and the DNA obtained in this manner can be re-amplified.

By means of successive cycles of in vitro transcription/translation, selection, and amplification ubiquitin variations with binding properties for a predetermined hapten or antigen can be enriched.

The further characterization of the ubiquitin variations obtained in this manner can be performed in the form of a soluble protein as detailed above after cloning of the corresponding gene cassette into a suitable expression vector. The appropriate methods are known to those skilled in the art or described in the literature.

Preferably, step (d), i.e. the step of detection of the proteins having a binding affinity with respect to a predetermined binding partner, is followed by a step of isolation and/or enrichment of the detected protein.

Following the expression of the proteins modified according to the invention having the ubiquitin-like folding motif these can be further purified and enriched by methods known per se. The selected methods depend on several factors known per se to those skilled in the art, for example the expression vector used, the host organism, the intended field of use, the size of the protein and other factors. For simplified purification the proteins modified according to the invention can be fused to other peptide sequences having an increased affinity to separation materials. Preferably, such fusions are selected that do not have a detrimental effect on the functionality of the ubiquitin protein or can be separated after the purification due to the introduction of specific protease cleavage sites. Such methods are also known per se to those skilled in the art.

According to the invention and particularly according to the procedure described immediately above variations of ubiquitin with a binding affinity with respect to a predetermined binding partner such as e.g. a hapten or antigen can be isolated in general.

As the binding partner for the modified proteins provided according to the invention all biologically and medically active and relevant molecules can be employed. Possible binding partners will be described in the following by way of example. It should be noted, however, that a plurality of other possible ligands can be added to this list. Similar to the relationship between antibody and antigen the list of potential binding partners can be completed by further potential ligands.

Preferably, the binding partner is a biological receptor, preferably a G protein-coupled receptor (GPCR; e.g. human GLP-1 receptor, human PTH receptor), or EGF receptor, HER2, HER3, VEGF/R1-4, Ep-CAM, or a ligand or a domain thereof, a tumor marker (prostate specific membrane antigen (PSMA)), cytokines (tumor necrosis factor alpha (TNF-α), tumor necrosis factor beta (TNF-β)), interleukins (e.g. IL-2, IL-6, IL-11, IL-12), growth factors (e.g., NGF (nerve growth factor) and the pro-form thereof, ProNGF, BMPs, EGF, MIA, MIA-2, FGFs, vascular endothelial growth factor (VEGF), PDGF, PlGF, IGFs), kinases, integrins (e.g. receptor IIb/IIIa (GPIIb/IIIa)), HSA (human serum albumin), F4 fimbrin[[e]], T and B cell antigen, preferably CD4, CD11, CD14, CD16, CD20, CD22, CD25, CD34, CD47, CD56, CD83, CD154, CTLA-4, an immunoglobulin or a portion thereof, for example a whole antibody, immunoglobulin G, E, M), an Fc portion of e.g., human immunoglobulin M or a segment of an antibody in the region of the antigen binding site, or a sugar (Lewis Y, Lewis X), or a toxin, for example mycotoxin, or a hormone, for example hydrocortisone.

A particular advantage of the present invention is that the modified proteins or ubiquitins are active in intra—as well as extracellular environments, i.e. bind to their respective binding partner both on the inside and the outside of the cell.

It is of particular advantage that the modified proteins or ubiquitins of the present invention can bind both haptens, i.e. small molecules, and antigens, i.e. large molecules, such as proteins in a quantifiable manner. By means of this variability of the proteins modified according to the invention probable newly generated binding partners are thus universally provided for a broad range of binding partners.

The proteins of the present invention can furthermore be used for the detection and for quantitative determination as well as for the separation and isolation of the respective binding partner.

Another application is in the diagnosis and treatment of diseases in which the respective binding partner is involved.

As already mentioned, the present invention also relates to the targeted alteration of individual amino acid positions which are localized out of the de novo generated, artificial binding site. In this manner, e.g. positions occupied by amino acids responsible for its biological function in the natural ubiquitin can be occupied by other amino acids. In this manner an ubiquitin protein scaffold is obtained which with respect to its biological functions such as e.g. with respect to the interaction with enzymes of the ubiquitination cascade is inactive but with respect to its structure and proteinchemical properties is largely identical to the starting protein. This can be performed e.g. by determation of the expression rate in $E.$ $coli$, analysis of the stability by spectroscopic methods such as fluorescence or circular dichroism measurement in connection with chemical or physical unfolding or detection in immunological standard tests such as ELISA.

By means of the substitutions Arg54 and Arg72 in each case to Leu for example the interaction with the ubiquitin activating enzyme E1 can be blocked (Burch and Haas, 1994). Furthermore, among others the amino acids Lys48 as well as Val70 to Gly76 are involved in the interaction with the ubiquitin conjugating enzyme E2 which is abolished by appropriate substitutions (Miura et al., 1999). Furthermore, the linkage of ubiquitin to proteins destined for proteolytic degradation or the covalent and selective linkage to polyubiquitin chains, respectively, takes place via the residues Gly75 and Gly76 and can be abolished by appropriate substitutions. Finally, the substitutions Ile44Ala and Val70Ala largely abolish the contact of ubiquitin to 26S protease and thereby the degradation of ubiquitin-labeled proteins (Beal et al., 1996). Accordingly, in a preferred embodiment of the invention a modified ubiquitin protein scaffold carrying the substitutions Ile44Ala, Lys48Arg, Arg54Leu, Val70Ala, Arg72Leu, Gly75Ala as well as the deletion of Gly76 serves as a starting point for the preparation of modified ubiquitins having novel binding properties. As determined by the procedures mentioned above, this modified ubiquitin protein scaffold is largely identical to ubiquitin with respect to its structure and its proteinchemical properties, i.e. stability, folding, production in $E.\ coli$, interaction with ubiquitin antisera etc.

It was surprising that the modifications separately mentioned in the different literature documents could be summarized in one ubiquitin without essentially altering the structure or stability thereof.

Surprisingly, by the described approach underlying the present invention it is possible to obtain modified proteins on the basis of proteins having a ubiquitin-liken folding motif which on the one hand show newly generated binding properties and on the other hand have the proteinchemical properties of ubiquitin to a large extent. In this respect, the ubiquitin-based modified proteins have dissociation constants of preferably $10^{-6}$ M or below, for example $10^{-6}$-$10^{-12}$ M, which are comparable to those of antibodies or fragments thereof, respectively. Furthermore, it is surprisingly possible to generate modified proteins with specific binding properties optionally directed against large molecules such as proteins or also against small molecules such as haptens or hormones. The target substances or target substance classes defined previously can be bound with high selectivity. The functionality observed of the de novo generated, artificial binding site with respect to affinity and specificity could not be expected beforehand since broad regions of the binding site are localized in the beta sheet which is generally considered as rigid and inflexible. Natural universal binding sites—such as e.g. those of antibodies—on the other hand are formed from flexible "loop" structures.

It is furthermore surprising that the ubiquitin protein scaffold used in the present case obviously tolerates the extensive alterations performed in primary sequence without any negative effect on the folding of the polypeptide chain. This is not only unexpected with respect to the number of amino acid substitutions—about 20% of the sequence of wild-type ubiquitin could be altered—but also due to the position of the changed positions in the protein scaffold. Thus, e.g. a tolerance to substitutions within the beta sheet usually considered as rigid and inflexible and particularly of directly adjacent amino acids could not be a prior expected.

Starting from the mutated DNA sequences of the ubiquitin-based modified proteins obtained the latter can be prepared by means of known methods of genetic engineering. In this respect, it is preferred to performed the production in a prokaryotic host—because of the low costs and the high yield—not excluding, however, the use of eukaryotic or cell-free systems. Generally, after insertion of the DNA sequence into a suitable expression vector and transformation, transfection or infection of appropriate organisms the foreign modified protein is synthesized by the bacterial transcription/translation system. For this purpose, the method of preparation can be adapted to individual modified proteins having the novel binding properties. Thus, if e.g. $E.\ coli$ is used as the host the ubiquitin-based modified protein can be secreted into the periplasmic space by means of a suitable signal sequence or can be prepared in the cytosol. If the modified protein of this invention is not folded within the cell and aggregates, functional refolding from such inclusion bodies is also possible. Cell-free systems can be advantageous e.g. in the case of variations with a low expression rate or a toxic effect on the host organism. Suitable methods of genetic engineering for the preparation and purification, respectively, of recombinant proteins are known to those skilled in the art and are described in the literature (e.g. Sambrook et al., 2001).

Accordingly, it is possible to provide ubiquitin-based modified proteins with novel binding affinity by the generation of an artificial binding site the highly variable surface of which enables molecular recognition of predetermined ligands such as e.g. haptens, peptides, proteins and other macromolecules or smaller molecules such as for example hormones.

Moreover, due to the variable surface properties of the randomized region also ubiquitin-based modified proteins having properties different from binding properties can be obtained by means of suitable selection methods. These can include for example a novel catalytic activity that did not exist previously for a predefined chemical reaction. This property is for example obtained if the binding partner is a molecule or a transition state bound by the modified protein in a such manner that the respective reaction is catalysed.

Thus, the present invention comprises the provision of molecules such as ubiquitin as a scaffold molecule for the introduction of novel binding properties that did not exist previously.

Furthermore, according to this invention a genetic library can be established in step d) of the method, e.g. by means of random mutagenesis. According to one of its embodiments the present invention also comprises genetic libraries prepared in this way. Particularly comprised are those genetic libraries established from human ubiquitin substituted in amino acid positions 2, 4, 6, 62, 63, 64, 65, and 66.

Furthermore, the protein scaffold can be modified in a targeted manner outside of the artificial binding site in order to confer additional functions to the modified protein. This can include e.g. the introduction of additional amino acids or the substitution of individual amino acids or peptides—preferably at the amino and carboxy termini—in order to obtain protein conjugates by chemical coupling with suitable reagents. Such fusions can also be prepared directly by means of linking the gene of the modified protein to that of the fusion partner by methods of genetic engineering. In contrast to antibodies this is simplified by the fact that only one foreign gene and therefore only one polypeptide chain is expressed or has to be functionally folded, respectively, by the bacterial host. Such fusion partners can be enzymes, cytotoxins, binding and multimerization domains but also modified proteins having the same or a different binding specificity, respectively.

The modified protein provided according to the invention with the folding motif typical for ubiquitin can be linked to a protein of the same or a different specificity in a site-specific and covalent manner to obtain in this way bivalent or bispecific binding properties, respectively, with respect to one or more binding partners.

Thus, for example two identical variations of ubiquitin obtained by the procedure described above and which bind to the same antigen can be covalently linked to each other in a site-specific manner via a single additionally introduced cysteine residue by means of methods known to those skilled in the art. Such bivalent binding proteins are characterized according to experience by a stronger apparent binding as compared to monovalent ones (avidity effect).

In the same manner, two variations of ubiquitin which bind to different antigens can be linked to each other by appropriate methods so that exclusively bispecific binding molecules are obtained. For the selective formation of such heterodimers polypeptides can be used which consist of either positively or negatively charged amino acids and each of which is fused to the carboxyterminal ends of the fusion partners. If oppositely charged amino acids are used these so-called polyionic tags will selectively undergo an electrostatic interaction with each other and link the binding proteins of different specificity to each other in the desired ratio of 1:1. In cancer therapy such bispecific agents can be contacted with effector cells of the immune system by addressing appropriate surface structures for example tumor cells to destroy the latter in a targeted manner.

Furthermore, ubiquitin variations isolated by one of the selection methods described above which therefore already show binding properties to a specific antigen can be modified to further enhance their affinity and/or specificity. For this purpose, new targeted and/or random substitutions of amino acids can be generated within and/or outside of the binding site. Appropriate methods for such maturation procedures are known to those skilled in the art. Maturation of already obtained ubiquitin variations can comprise affinity and specificity but is not limited thereto. Other protein properties which can be improved are for example stability, solubility and production level in prokaryotes. In the context of the present invention for example the affinity of a ubiquitin variation binding to the $F_c$ portion of immunoglobulin M was increased in this manner by a factor of 10 by the targeted substitution of two amino acids within the binding site.

The ubiquitin-based modified proteins provided by the present invention—in a manner analogous to antibodies and fragments thereof—find use in a broad spectrum of applications. This comprises diagnostic and therapeutic applications as well as chromatographic methods. Thus, target substances can be detected directly in any of the bioanalytical tests such as ELISA, Western blot, and others. Furthermore, the proteins modified according to the invention which bind e.g. to immunoglobulins and are conjugated to an enzyme or fluorophore are suitable as universal secondary reporter molecules in appropriate test systems. Due to their advantageous properties the ubiquitin-based modified proteins find a preferred application in therapeutic use such as e.g. in the treatment of tumor or infectious diseases. In this way effects can be utilized which are based on the receptor or ligand blockage by specific binding of the modified protein. Similarly, modified proteins having the novel binding properties which bind to surface proteins on tumor cells due to a conjugation with suitable effectors can destroy such cells in a targeted manner or activate appropriate pre-toxins selectively in the tumor tissue, respectively.

For the proteins modified and selected according to the invention, thus, a broad spectrum of possible applications is available. They can be used not only in the medical-pharmaceutical field but also in the field of analytics, of the nutrient and food stuff industry, of nutrient supplements, of cosmetics, of medical and non-medical diagnostics and analysis etc. Naturally, the field of use depends on the type of binding partner selected.

In the field of human and veterinary medical therapy and prophylaxis pharmaceutically effective medicaments can be prepared by methods known per se. Depending on the galenic preparation these compositions can be administered intravenously, intraperitoneally, intramuscularly, subcutaneously, transdermally or by other methods of application. The type of pharmaceutical preparation depends on the type of disease to be treated, the severity of the disease, the patient to be treated and other factors known to those skilled in the art of medicine. The administration can either be parentally by injection or infusion, systemically, rectally of by other methods conventionally employed.

The compositions are adapted to contain a therapeutically effective dose. The quantity of the dose to be administered depends on the organism to be treated, the type of disease, the age and weight of the patient and further factors known per se.

The compositions can contain auxiliary agents known per se. These include for example stabilizing agents, surface-active agents, salts, buffers, coloring agents etc.

The pharmaceutical composition can be in the form of a liquid preparation, a cream, a lotion for topical application, an aerosol, in the form of powders, granules, tablets, suppositories, or capsules, in the form of an emulsion or a liposomal preparation. The compositions are preferably sterile, non-pyrogenic and isotonic and contain the pharmaceutically conventional and acceptable additives known per se. Additionally, reference is made to the regulations of the U.S. pharmacopoeia.

The following Examples are provided for further illustration of the invention. Die invention is particularly demonstrated with respect to the modification of ubiquitin as an example. Die invention, however, is not limited thereto, and the following Examples merely show the practicability of the invention on the basis of the above description. For a complete disclosure of the invention reference is made also to the literature cited in the application and in the annex which are incorporated in their entirety into the application by reference.

In the following, the present invention will be described in more detail with respect to Examples and the accompanying Figures wherein

BRIEF DESCRIPTION OF THE DRAWINGS

FIG. 4 illustrates the procedure for the construction of a library of ubiquitin variations;

DETAILED DESCRIPTION

Figure 1:
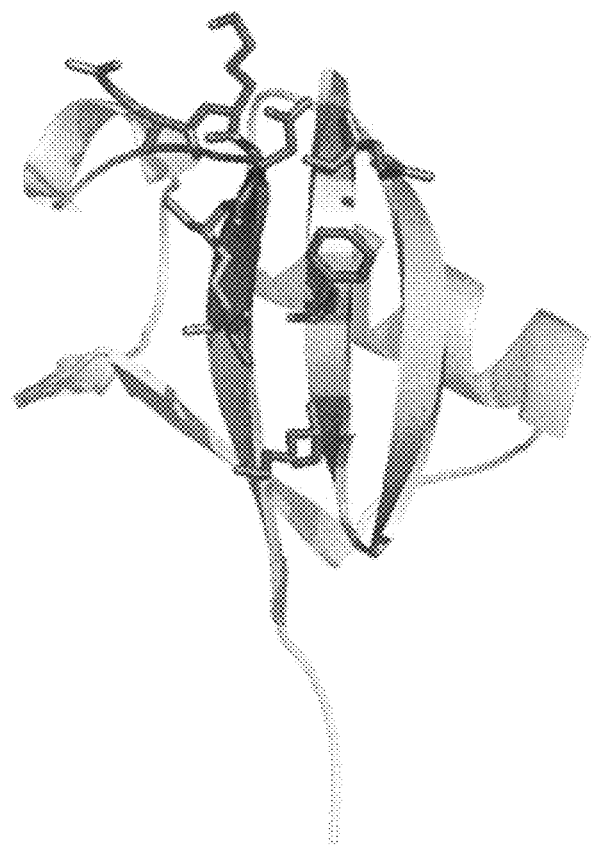
FIG. 1 shows a region of the de novo generated, artificial binding site on the surface of wild-type ubiquitin (PDB code: 1ubi)

FIG. 1: The crystallographic structure of the wild-type ubiquitin (PDB code: 1ubi; Vijay-Kumar et al., 1987) with the artificially generated binding site on the surface. The three-dimensional representation of the secondary structural elements was performed using the PyMOL program (DeLano Scientific, San Francisco). The residues to be randomly substituted in the library prepared as an example comprise positions 2, 4, 6, 62, 63, 64, 65, 66, and are shown with their side chains.

Figure 2:
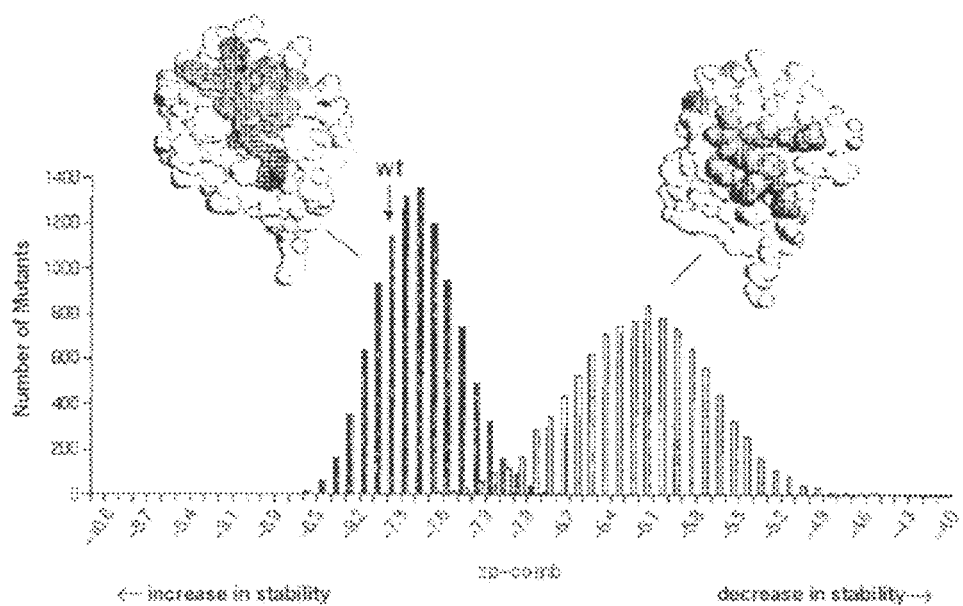
FIG. 2 shows the results of the computerized analysis of the protein stability of each of $10^4$ variations randomly substituted at positions 2, 4, 6, 62, 63, 64, 65, 66 compared to ubiquitin (WT) and a control epitope.

FIG. 2: Generation of a binding site on the surface of wild-type ubiquitin (PDB-Code: 1ubi). The residues to be randomly substituted in the library to be prepared (positions 2, 4, 6, 62, 63, 64, 65, 66 represented in light grey) were selected by computerized analysis with respect to their exposition to the solvent and the stabilizing or destabilizing effect, respectively, which an amino acid substitution could have at the respective positions. Using the ProSAII software the protein stability of each of 104 variations was then determined in comparison to ubiquitin (WT) and the same number of randomly taken samples of variations in which the residues of a "control epitope" (positions 24, 28, 31, 32, 35, 37, 38, 39 represented in dark grey) were substituted. As a measure for stability the value of the combined $C^\alpha/C^\beta$ potentials ("zp-comb") is noted. Approximately 19% of the variations generated in silico which had been randomly substituted in the region of the binding site had a stability which was at least as high as that of ubiquitin (WT) while about 90% were more stable than those bearing the "control epitope". The generation of a binding site by random amino acid substitutions in the region analyzed should therefore be tolerated by the protein structure of ubiquitin without drastically affecting the stability thereof. This computerized method assists in the selection of suitable surface-exposed amino acids.

Figure 3:
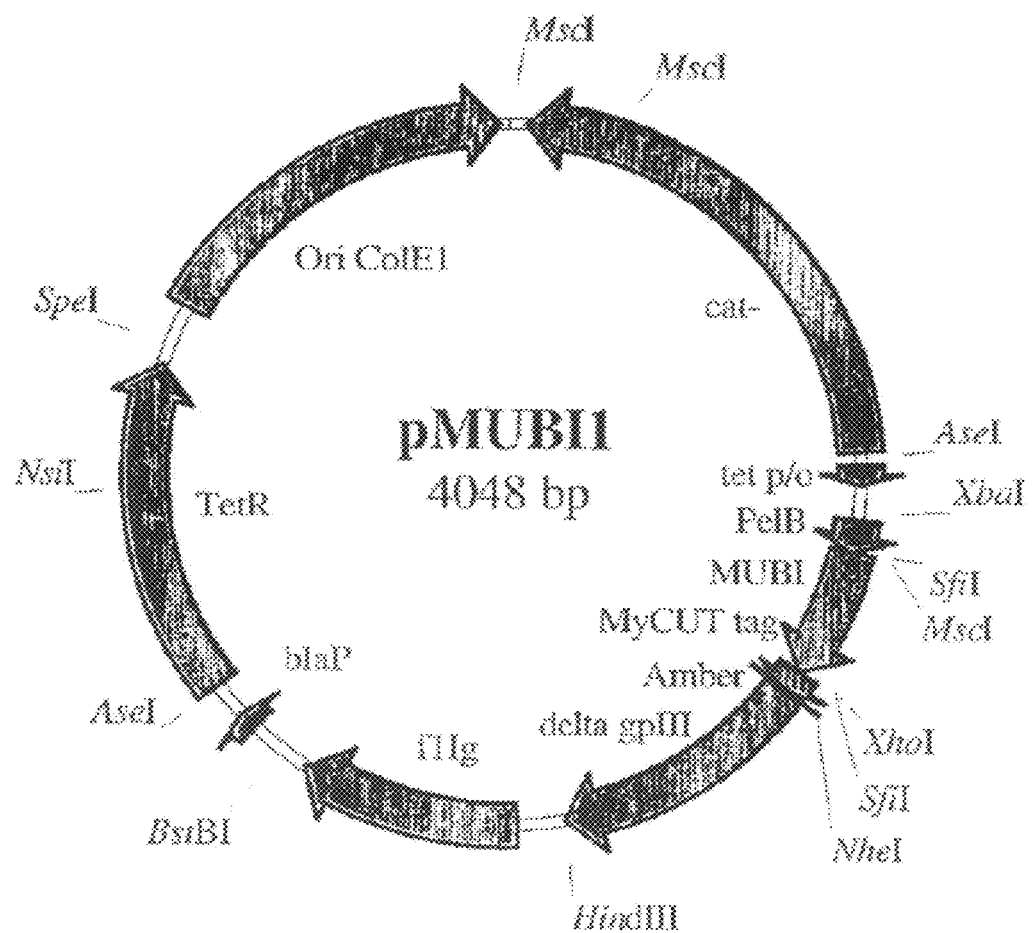
FIG. 3 illustrates the phasmid vector pMUBI-1 for use in the selection of ubiquitin-based modified proteins having novel binding properties.

FIG. 3: The phasmid vector pMUBI-1 for use in the selection of MUBI variations by phage display. pMUBI-1 is used for the preparation of phage libraries and codes for a fusion protein of the PelB signal sequence, the gene for the ubiquitin variation, a MyCUT tag and a C-terminal fragment of the phage capsid protein (aa 253406, delta gpIII) under the transcriptional control of the tetracyclin promoter/operator ($tet^{p/o}$). Amber refers to the position of the amber stop codon in the fusion gene. The insertion of the mutated gene cassette of MUBI is carried out via the two SfiI restriction sites. f1Ig, $bla^P$, tetR, Ori, ColE1 and Cat refer to the intergenic region of phage f1, the tetracyclin repressor gene under the control of the β-lactamase promoter, the origin of replication and the chloramphenicol acetyltransferase gene.

FIG. 4: Procedure for the construction of a phage display library of ubiquitin variations.

Figure 5:
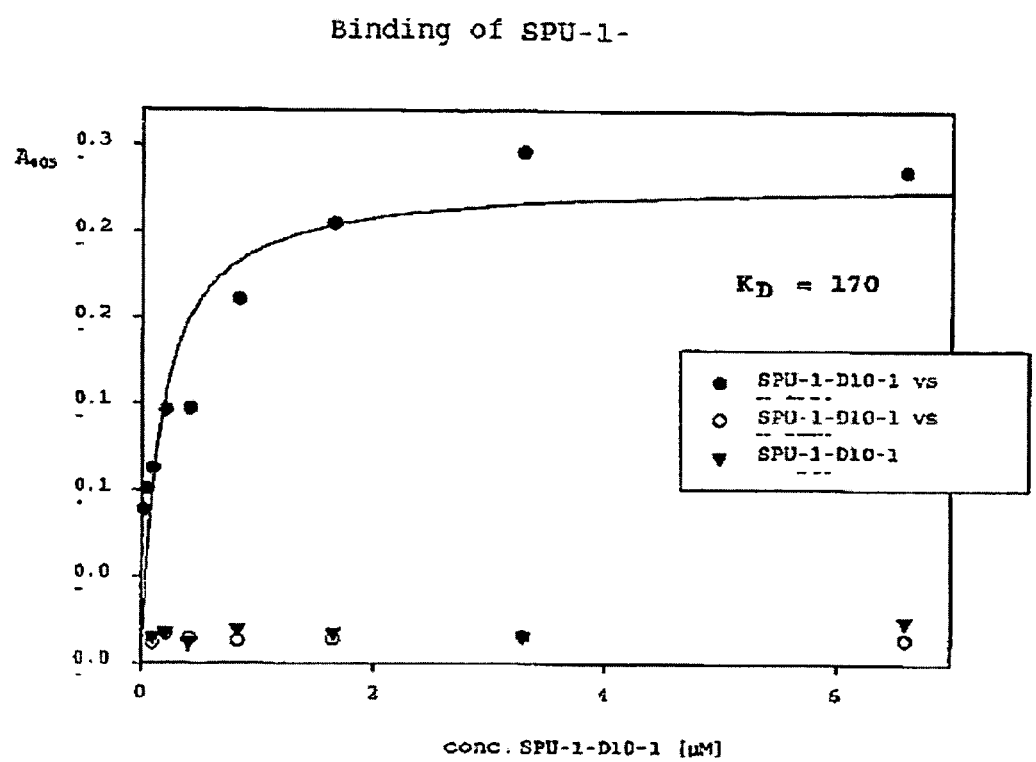
FIG. 5 shows the result of an ELISA experiment to detect the binding of a ubiquitin-based modified protein selected by means of phage display to the corresponding protein.

FIG. 5: Binding of the ubiquitin variation SPU-1-D10 obtained from the selection by means of phage display against recGLP1-R to the aminoterminal domain of the human GLP-1 receptor prepared by recombination in the ELISA. An appropriate number of wells of a microtiter plate was filled over night at 4° C. with recGLP1-R and with BSA, respectively, or the aminoterminal domain of the human PTH receptor (recPTH-R) prepared by recombination. Remaining binding sites were saturated by incubation with 3% BSA in PBS containing 0.5% TWEEN® 20 non-ionic detergent (2 hrs., room temperature (RT)). SPU-1-D10 was applied in serial dilutions in PBST 0.1 for 90 min at 30° C. Bound modified protein was detected with ubiquitin antiserum (1:10 in PBST 0.1, 60 min at 30° C.) and rabbit antibodies (1:2000 in PBST 0.1, 60 min at 30° C.) conjugated to peroxidase. The detection was carried out using the IMMUNOPURE® kit of Pierce. Between the steps washing was carried out was three times with PBST 0.1—an additional 3× with PBS prior to chromogenic detection. The signal intensity was detected at 405 nm after stopping the color reaction with $H_2SO_4$ and plotted against the corresponding concentration of the modified protein. Determination of the $K_D$ value under equilibrium conditions was carried out by non-linear regression.

Figure 6:
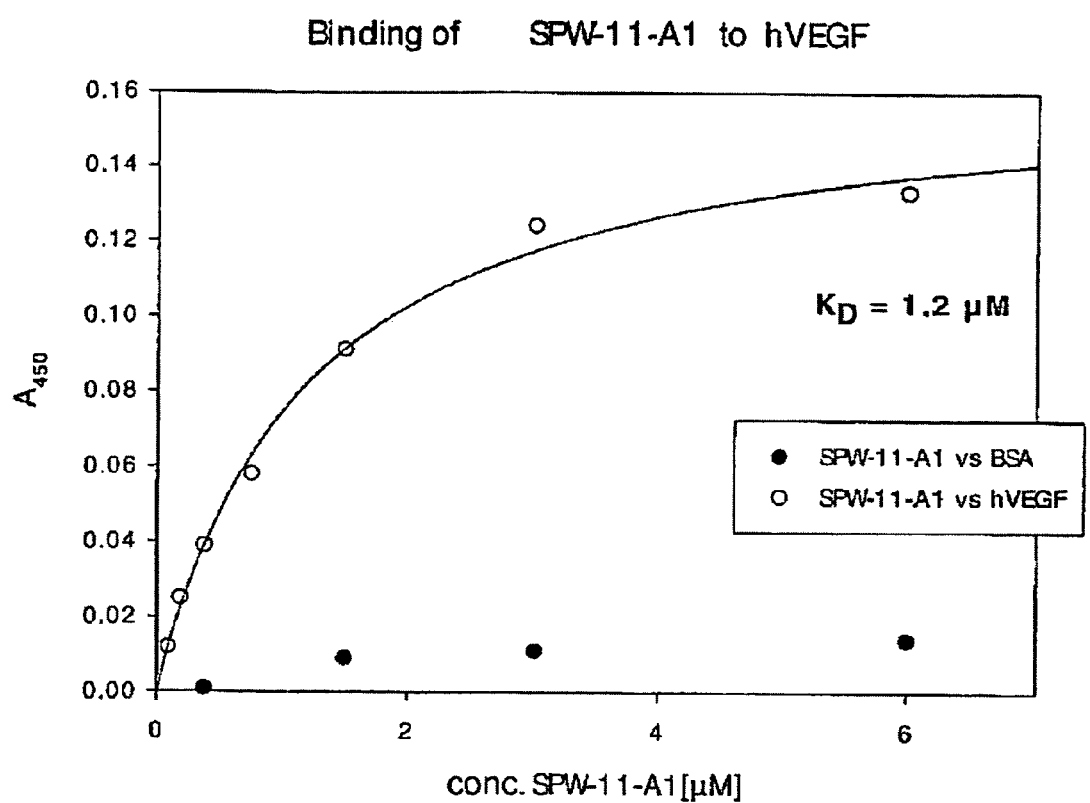
FIG. 6 shows the result of an ELISA experiment to detect the binding of a ubiquitin-based modified protein selected by means of ribosomal display to the corresponding protein.

FIG. 6: binding of the ubiquitin variation SPW-11-A1 obtained from the selection by means of ribosomal display on VEGF in the ELISA. The same procedure as described in FIG. 5 was followed in this experiment. Determination of the $K_D$ value under equilibrium conditions was carried out by non-linear regression.

Figure 7:
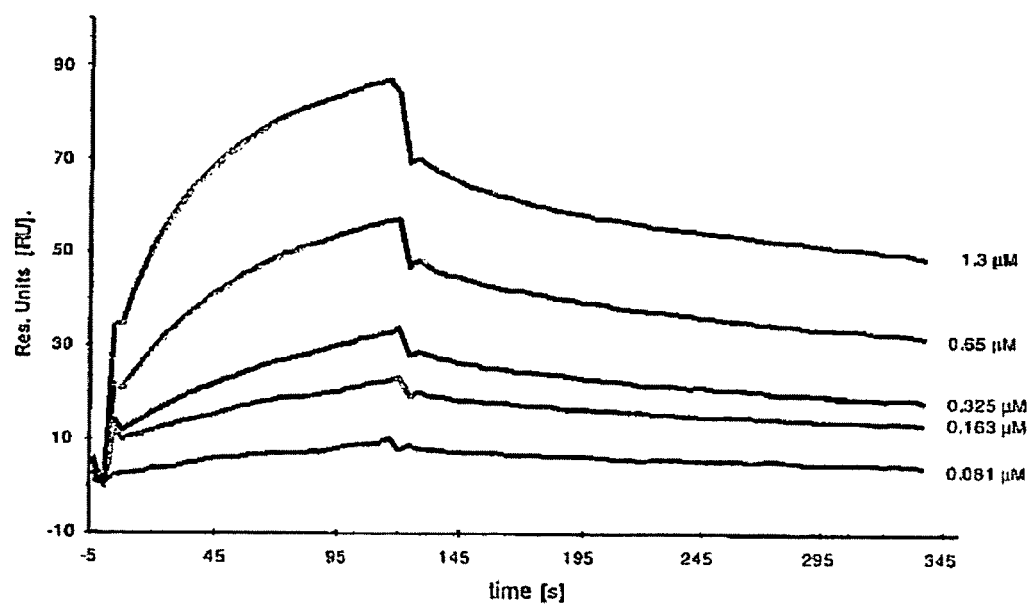
FIG. 7 shows the result of a BIACORE experiment to detect the binding of a ubiquitin-based modified protein selected by means of ribosomal display to the corresponding protein.

FIG. 7: Binding of the ubiquitin variation SPU-11-58 obtained from the selection by means of ribosomal display on VEGF in the BIACORE. On the surface of the channel of a CM5 chip first VEGF was immobilized while a reference channel remained uncharged. For the application of different concentrations of SPU-11-58 the net signal of the binding event was obtained in each case. The injection period for all solutions was 2 min at a flow rate of 35 μl/min. The binding signals of different concentrations of SPU-11-58 (1.3 μM, 0.65 µM, 0.325 µM, 0.163 µM, 0.081 µM) are shown superimposed in relation to the start of injection. After every measurement the surface was regenerated at a pulse of 15 s with 10 mM HCl. Determination of the $K_D$ value under equilibrium conditions was carried out using the BIAevaluation software 3.1 (Biacore).

Figure 8:
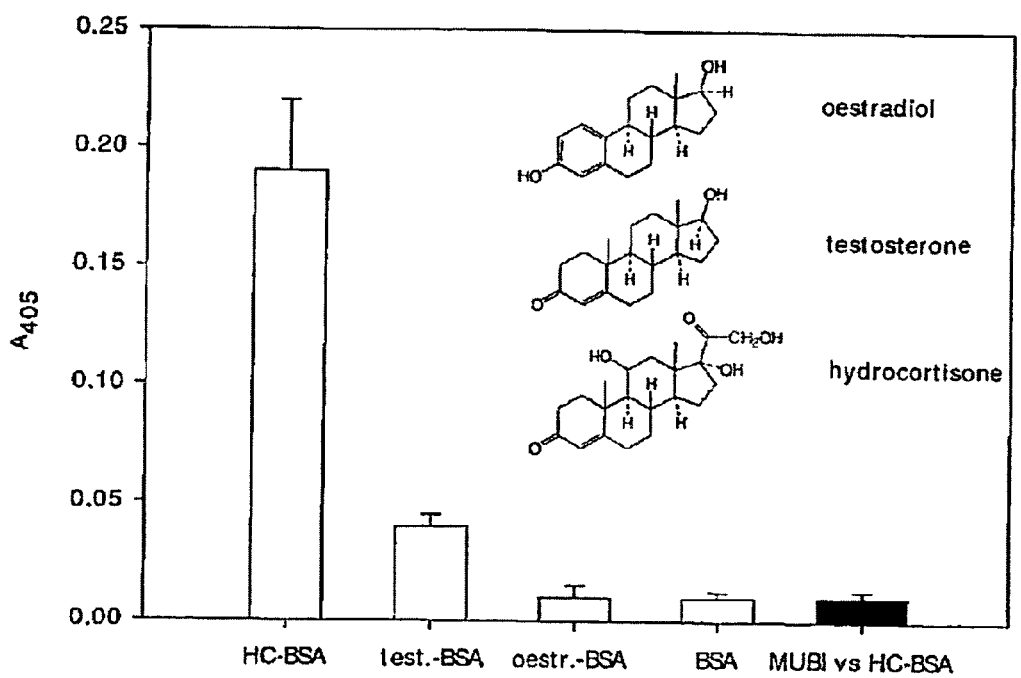
FIG. 8 shows the result of an ELISA experiment to detect the binding specificity of a ubiquitin-based modified protein selected by means of phage display to the corresponding hapten.

FIG. 8: Binding of the ubiquitin variation SPU-3-H13 obtained from the selection against hydrocortisone to steroids in the ELISA. Three wells each of a microtiter plate were filled with a BSA conjugate of hydrocortisone, testosterone and oestradiol or with BSA, respectively, and incubated with SPU-3-H13 (4 µM) or with the ubiquitin protein scaffold which was unchanged in the region of the binding site (50 µM), respectively, each in PBST 0.1 (90 min at 30° C.). The detection of binding is carried out with Ni-NTA/peroxidase conjugate (1:500 in PBST 0.1, 60 min at 30° C.) and using the ImmunoPure kit of Pierce. Blocking and Washing: see FIG. 5. The signal intensity was detected at 405 nm after stopping the color reaction with $H_2SO_4$ and the mean values of three measurements were plotted.

Figure 9:
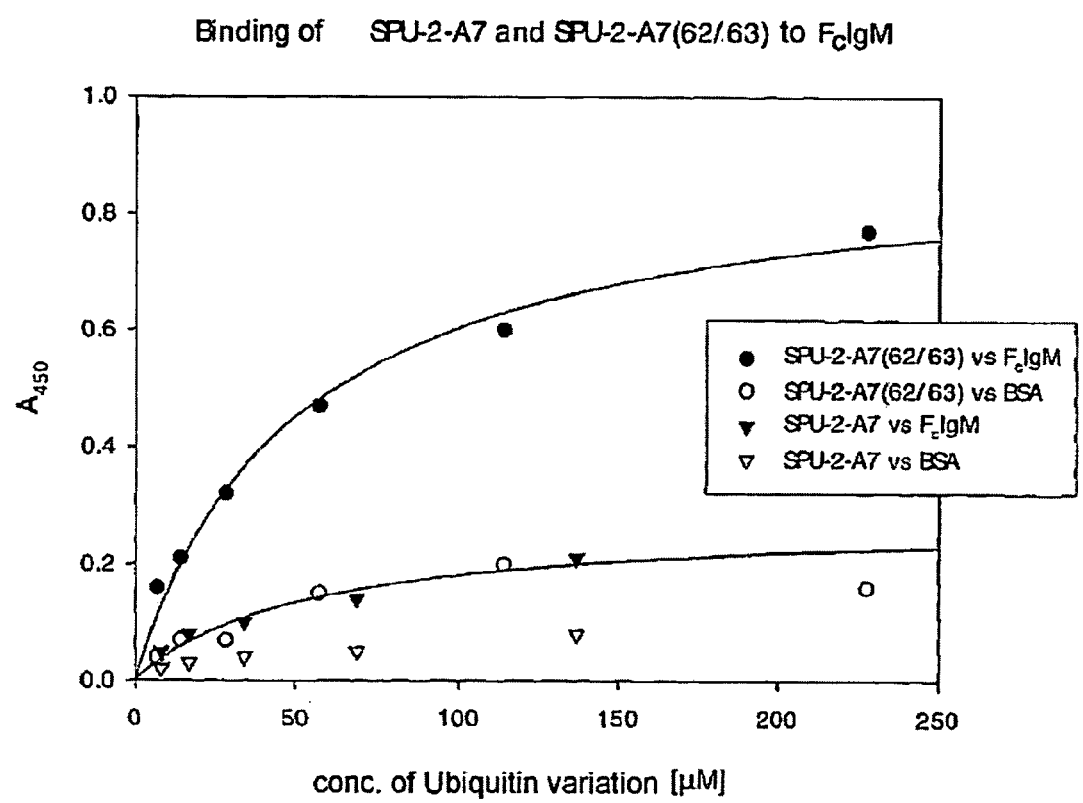
FIG. 9 shows the result of an ELISA experiment to detect the improved binding of a variation of SPU-3-A7, an ubiquitin-based binding protein to IgM $F_c$ selected by phage display, obtained by means of secondary mutagenesis to its antigen.

FIG. 9: Comparison of the binding of the ubiquitin variations SPU-2-A7 and SPU-2A7 (62/63) to $F_c$ IgM following affinity maturation by means of site-directed random mutagenesis in the ELISA. The same experimental procedure as in FIG. 5 was followed. Determination of the $K_D$ value under equilibrium conditions was carried out by non-linear regression.

Figure 10:
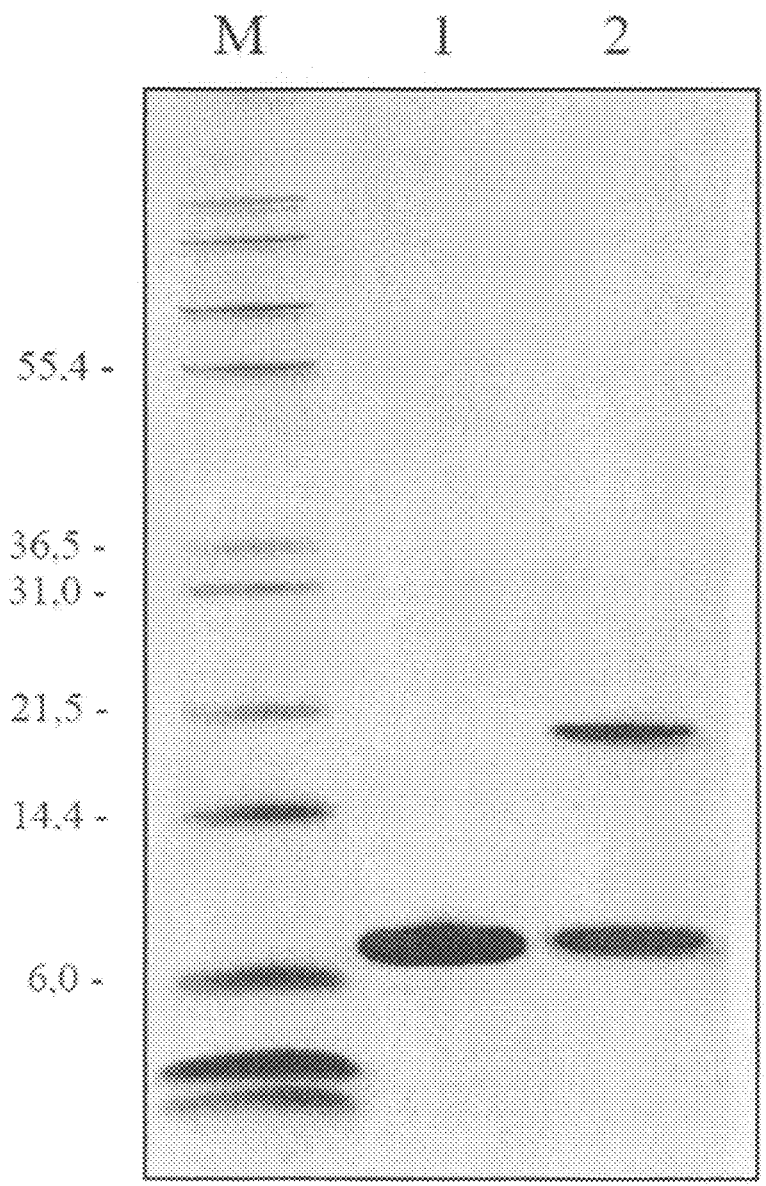
FIG. 10 shows the result of an experiment for the site-specific, covalent coupling of two ubiquitin-based proteins via single, carboxyterminal cysteine residues by means of bis-maleimido hexane.

FIG. 10: Analysis of the site-directed, covalent coupling of two ubiquitin-based proteins via single, carboxyterminal cysteine residues by SDS-PAGE. 20 µl each of the uncoupled protein (lane 1) as well as the sample after the coupling reaction (lane 2) were applied. Following electrophoresis the gel was stained with coomassie. The molecular weights of the size standard (lane M) are given in kDa.

Example 1

Provision of a Synthetic Ubiquitin Gene for the Selection of Modified Proteins having a Newly Generated Binding Affinity Genetic engineering work was performed by standard protocols known to those skilled in the art such as e.g. those of Sambrook et al. (2001).

For the preparation of the DNA sequence (SEQ ID NO. 1) for a modified ubiquitin protein scaffold having the substitutions Ile44Ala, Lys48Arg, Arg54Leu, Val70Ala, Arg72Leu, Gly75Ala as well as the deletion of Gly76 as a starting point for the preparation of artificial binding proteins the procedure was as follows: for gene synthesis a PCR reaction was performed in a volume of 50 µl in which 2.5 µl each of the six oligodeoxynucleotides (SEQ ID NO. 2, SEQ ID NO. 3, SEQ ID NO. 4, SEQ ID NO. 5, SEQ ID NO. 6, SEQ ID NO. 7; 0.1 µM each) representing together in their base pair sequence the gene to be synthesized were present as templates. The sequences of the oligodeoxynucleotides employed each corresponded to segments of the coding and the non-coding DNA strand, respectively, of the artificial gene with a length of 40 to 50 base pairs alternatingly overlapping at their 3' and 5' ends by approx. 15 bases. In addition, the sample contained 2.5 µl each of flanking primers (SEQ ID NO. 8, SEQ ID NO. 9; 10 µM) as well as 5 µl of 10×Taq buffer (100 mM Tris/HCl pH 9.0, 500 mM KCl, 1% (v/v) Triton X-100), 3 µl 25 mM $MgCl_2$, and 4 µl dNTP mix (2.5 mM each of dATP, dCTP, dGTP, dTTP). After filling up with $H_2O$ the reaction sample was heated in the thermocycler for denaturation for 2 min to 94° C. Then, 2.5 U Taq polymerase (Promega) were added during heating (hot start) and the PCR program was started. Incubation was performed for 25 cycles of each 1 min at 94° C., 1 min at 55° C., and for 1.5 min at 72° C. A final incubation was carried out for 5 min at 72° C.

The desired PCR product was identified by means of analytical agarose gel electrophoresis and purified from the sample using the MinElute Reaction Cleanup kit (Qiagen). 1.0 ng of the isolated DNA were used as a template for a second amplification, this time using Pfu polymerase (Promega) also in a volume of 50 µl. For this purpose, 5 µl of the supplied 10×Pfu buffer (200 mM Tris/HCl, pH 8.8, 20 mM $MgCl_2$, 100 mM KCl, 100 mM $(NH_4)_2SO_4$, 1% (v/v) Triton X-100, 1 mg/ml BSA) as well as 4 µl dNTP mix were used and filled up with $H_2O$. In addition, the sample contained flanking primers (SEQ ID NO. 8, SEQ ID NO. 9; 10 µM) for the introduction of suitable restriction sites. The desired PCR product was isolated by means of preparative agarose gel electrophoresis and was inserted into the cloning vector pCR®4Blunt-TOPO® using the Zero Blunt® TOPO® PCR Cloning kit (Invitrogen) according to the manufacturer's instructions. The chemically competent cells supplied were transformed with the corresponding ligation reaction sample and spread on an agar plate in LB/amp/kan medium. The plate was incubated for 16 hrs. at 37° C., and the colonies grown were analysed for the desired ligation product. For this purpose, plasmid DNA was prepared in the mini scale using the plasmid isolation kit of Quiagen company according to the manufacturer's instructions, and was subjected to a restriction digest with the DNA endonucleases NdeI and XhoI (New England Biolabs) for which the recognition sequences had been introduced into the PCR product by the flanking primers. A sequence analysis was performed on plasmids having the expected cleavage pattern in the region of the gene cassette inserted using Taq DNA polymerase. For this purpose, the CycleReader™ AutoDNA Sequencing kit (Fermentas) was used according to the manufacturer's instructions as well as 0.5 µg of plasmide DNA and 1.0 pmoles of the respective fluorescence-labeled primer. The newly synthesized DNA strand was labeled during the polymerase reaction and terminated statistically, but in a base-specific manner by the incorporation of dideoxynucleotides. The fluorescent DNA fragments obtained were then separated in a liquor sequencing apparatus by polyacrylamide-urea gel electrophoresis and visualized as a band pattern for A, C, G, T in adjacent lanes.

Gene cassettes having the correct DNA sequence were cut from the cloning vector pCR®4Blunt-TOP® by preparative NdeI/XhoI restriction digest and isolated by preparative agarose gel electrophoresis. The insertion of the gene for the modified ubiquitin protein scaffold is carried out into the expression vector pET20B(−) (Novagen) for the production of the corresponding protein or into the phasmid vector pMUBI-1 for the construction of a library of ubiquitin-variations, respectively.

Example 2

Preparation of a Library of Ubiquitin Variations

For random site-specific mutagenesis of 8 codons at the amino and carboxy terminus, respectively, of the synthetic ubiquitin gene two successive PCR reactions were performed. The first amplification step was performed using Pfu polymerase (Promega) in a volume of 10×50 µl. For this purpose, 5 µl of the supplied 10×Pfu buffer as well as 4 µl dNTP mix were used per each sample and filled up with $H_2O$. Furthermore, each sample contained 2.5 µl of flanking primers (SEQ ID NO. 10, SEQ ID NO. 11; 10 µM) for the introduction of the desired base pair substitutions. As a template, 1.0 ng pMUBI-1 were used carrying the non-mutated synthetic ubiquitin gene. Following the addition of 2.5 U of Pfu polymerase (see above) an incubation was performed for 25 cycles of each 1 min at 94° C., 1 min at 60° C. and for 1.5 min at 72° C. A final incubation was carried out for 5 min at 72° C. For the selective degradation of the template DNA employed 10 U DpnI were added per reaction sample and incubated for 1 hour at 37° C. The desired PCR product was isolated by means of preparative agarose gel electrophoresis and the QIAquick gel extraction kit (Qiagen).

The second amplification step was performed in a sample volume of 1,000 µl wherein approx. 1.0 ng of the product obtained in the first PCR reaction were used and Taq polymerase was employed. The reaction sample was pipetted—adapted to 20 times the volume—as detailed above consisting of 10×Taq buffer, 25 mM $MgCl_2$, dNTP mix as well as the flanking primers (SEQ ID NO. 12, SEQ ID NO. 13; 10 µM) which were biotinylated at their 5' ends and each carrying recognition sequences for SfiI endonuclease which were not compatible with each other. After filling up with $H_2O$, 2.5 U of Taq polymerase were added in the heat (see above) and the PCR program was started. An incubation was performed for 25 cycles of each 1 min at 94° C., 1 min at 60° C. and for 1.5 min at 72° C. A final incubation was carried out for 5 min at 72° C.

The subsequent cleavage of the amplification product obtained is carried out directly in the PCR reaction sample. For this purpose, in total volume of 4,000 µl the complete PCR reaction solution was mixed with the corresponding volume of the supplied 10× buffer II (100 mM Tris/HCl, pH 7.9, 100 $MgCl_2$, 500 mM NaCl, 10 mM dithiothreitol), 10×BSA solution and $H_2O$. Furthermore, 4,000 U of the restriction enzyme SfiI (New England Biolabs) were added and incubated for 16 hrs. at 50° C. The DNA was isolated from the sample using the MinElute Reaction Cleanup kit (Qiagen) and resuspended in 400 µl of sterile $H_2O$. For the separation of the PCR product which was not cleaved by SfiI the isolated DNA was mixed with the same volume of "Binding Solution" (Dynal) containing 1.0 mg/ml magnetic beads having streptavidine coupled to their surface ("Dynabeads Kilobase Binder") and incubated for 4.5 hrs. on a roller mixer at room temperature (RT). The beads with the optionally still present biotinylated DNA were precipitated while DNA completely cleaved by SfiI which should no longer have biotinylated ends remained in the supernatant and was precipitated over night. The ubiquitin gene mutagenized at the desired positions and cleaved by SfiI obtained in this manner was dissolved in sterile $H_2O$, again desalted using the QIAquick PCR Purification Kit (Qiagen) and finally had a concentration of 200 fmol/µl in $H_2O$.

For the preparation of the recipient vector the phasmid pMUBI-1 was cut with SfiI according to the manufacturer's instructions and the larger (vector-) fragment was isolated by means of preparative agarose gel electrophoresis and the QIAquick Gel Extraction Kit (Qiagen). To avoid intramolecular ligation the 5' ends thereof were dephosphorylated. For this purpose, 0.5 U of alkaline phosphatase from shrimp (*Pandalus borealis*) as well as the buffer supplied were used in a total volume of 200 µl. The mixture was incubated for 90 min at 37° C., the DNA isolated from the sample using the QIAquick PCR Purification Kit (Qiagen) and again desalted (QIAquick PCR Purification Kit). The DNA of the vector fragment finally had a concentration of 50 fmol/µl in $H_2O$. For ligation 1.6 pmol of the PCR fragment and 8.0 pmol of the vector fragment of pMUBI-1 were incubated in the presence of 2 U T4 DNA ligase (GibcoBRL) in a total volume of 1,600 µl (50 mM Tris/HCl, pH 7.6, 10 mM $MgCl_2$, 1 mM ATP, 1 mM DTT, 5% (w/v) PEG-8,000) for three days at 16° C. After heating the sample to 65° C. for 15 min the DNA was precipitated. For this purpose, 100 µl of each of the reaction solutions were mixed with 100 µl ethanol as well as 10 µl 5 M NaAc, pH 3.0 and kept for 16 hrs. at −20° C. Subsequently, a centrifugation was carried out (60 min, 12,500 g), the sample was washed with ethanol (70% v/v, −20° C.), recentrifugated, and the precipitated DNA was finally dissolved in 60 µl of sterile $H_2O$.

For electroporation the Gene Pulser® II system (Biorad) as well as cuvettes having an electrode spacing of 1.0 mm (Biozym) were used at 4° C. in the cold room. Using 3.5 µl of each of the solutions obtained above electrocompetent *E. coli* XL1Blue (Stratagene) were transformed according to the manufacturer's instructions. The cell suspension obtained was plated onto five agar plates (20×20 cm) with LB/chloramphenicol medium. The plates were incubated for 16 hrs. at 37° C. and the colonies grown were counted. The library constructed was found to include $2.8 \times 10^7$ independent clones each of which should be present 10,000 times in the library. Then, the colonies were floated off in a total of 100 ml SOC medium containing 10% (v/v) glycerol and stored in aliquots of 1.0 ml at −80° C. The phasmid vector was isolated from 12 clones which were randomly selected among those obtained using the DNA Miniprep Kit of Qiagen company and the DNA sequence was analysed in the region of the mutagenized ubiquitin gene. All of these clones had functional sequences—i.e. no reading frame shifts by insertions or deletions—as well as qualitatively completely different substitutions at the mutagenized positions. Random substitutions outside of the mutagenized regions were not present.

Example 3

Preparation of Ubiquitin Variations on the Phage Surface and Selection of Ubiquitin Variations Against Proteins and Haptens For the production of phagemids variations of the mutated ubiquitin presented on the surface, 100 ml of 2×YT/chloramphenicol medium were inoculated with 1.0 ml of the glycerol culture obtained in Example 2 and incubated for 16 hours at 37° C. and 220 ppm. With 10 ml of this stationary culture 1 liter of 2×YT/chloramphenicol medium was inoculated and agitated at 37° C. and 220 rpm up to a cell density of $OD_{600}$=0.4. The infection was carried out with $10^{13}$ cfu of M13KO7 helper phages and an incubation at 37° C. without shaking for 30 min. After addition of 50 mg/l kanamycine the sample was agitated for 30 min at 37° C. and 220 rpm, and then the gene expression on pMUBI-1 was induced by adjusting the culture to 0.2 mg/l anhydrotetracycline (stock solution: 2.0 mg/ml in DMF). The incubator temperature was then decreased to 26° C., and the culture was agitated for 16 hours at 220 rpm. Finally, the cells were sedimented by centrifugation (30 min, 12,000 g, 4° C.) and discarded while the supernatant was filtered (0.45 µm). The phagemids contained were precipitated by addition of ¼ volume of 20% (w/v) PEG 6,000, 2.5 M NaCl and incubation for 1 hour on ice and sedimented by centrifugation (30 min, 12,000 g, 4° C.). Then, the phagemids were dissolved in 4 ml of ice-cold PBS (137 mM NaCl, 2.7 mM KCl, 8 mM $Na_2HPO_4$, 2 mM $KH_2PO_4$), stored for 30 min on ice and centrifuged (30 min, 12,000 g, 4° C.). The supernatant was added with ¼ volume of 20% (w/v) PEG 6,000, 2.5 M NaCl, the phagemids were again precipitated by incubation for 1 hour on ice and precipitated by centrifugation (30 min, 12,000 g, 4° C.). Then, the phagemides were again solved in 4 ml ice-cold PBS, stored for 30 min on ice and centrifuged (30 min, 12000 g, 4° C.). The supernatant was mixed 1:1 with 4% (w/v) bovine serum albumin (BSA) in PBS, incubated for 30 min on a roller mixer at RT and then directly used in the affinity enrichment.

As an affinity matrix for the isolation of phagemids with surface-presented ubiquitin variations which should bind to previously defined target substances, 24 wells each of a microtiter plate were coated with the respective substance. As the target substances served the recombinantly prepared aminoterminal domain of the human GLP-1 receptor (recGLP1-R; Bazarsuren et al., 2002), the $F_c$ portion of human immunoglobulin M ($F_c$ IgM) as well as hydrocortisone (HC) coupled to BSA which were immobilized over night at 4° C. on the microtiter plate.

Unoccupied binding sites on the surface of the microtiter plate were blocked by incubation of each of the wells with 400 μl of 4% BSA in PBS for 90 min at RT. Then, 100 μl of the phagemid solution prepared were pipetted into each well and incubated at RT (room temperature) for 90 min. Unbound phagemids were then removed by washing twice with PBS containing 0.05% (v/v) TWEEN® 20 non-ionic detergent (PBST 0.05), incubating twice with 400 μl of 4% BSA in PBS for 5 min and washing twice with PBS as well as vigorous tapping. Phagemids bound to the affinity matrix were finally eluted by means of 100 μl of 100 mM triethylamine per well and incubation for 10 min at RT. The solutions containing the eluted phagemids were combined—each separately depending on the respective target substances—and immediately neutralized by addition of ½ volume of 1 M Tris/HCl, pH 7.4. The solution obtained in each case was transferred to 20 ml of a culture having a cell density of $OD_{600}$=0.4 for the infection of *E. coli* XL1 Blue and agitated for 30 min at 37° C. and 220 rpm. The wells of the microtiter plate were again washed (5×PBST, 0.05, 1X PBS) and added with 100 μl each of a culture of *E. coli* XL1 Blue having a cell density of $OD_{600}$=0.4. After an incubation at 37° C. for 30 min these cells were combined with those infected previously. The respective cell suspensions were plated on an agar plate (20× 20 cm) with LB/chloramphenicol medium and generally contained between $10^5$ and $10^7$ colony forming clones. The plates were incubated for 16 hours at 37° C., the colonies grown were floated off with 10 ml of SOC medium containing 10% (v/v) glycerol and stored in aliquots of 1.0 ml each at −80° C.

For repeated phage production and new cycles of affinity enrichment the method described was repeated selecting ten times lower culture volumes for the culture of the bacterial cells and more stringent washing conditions (2nd round: 3× washing with PBST, three times of incubation with 4% BSA in PBS for 5 min and 3× washing with PBS; 3rd round: 6× washing with PBST 0.1, three times incubation with 4% of BSA for 5 min and 3× washing with PBS).

Example 4

Isolation and Characterization of Monoclonal Phagemids with Specific Binding to the Target Substrates (Single Phage ELISA)

From each of the clones obtained after the 3rd round of the affinity enrichment on recGLP1-R, $F_c$ IgM as well as HC, 96 were selected randomly and analyzed in a single phase ELISA with respect to their binding to the respective antigen or hapten, respectively. For this purpose, 300 μl each of 2×YT/chloramphenicol medium were inoculated with a single colony and agitated for 18 hours at 37° C. and 220 rpm. With 80 μl each of this stationary culture 4 ml 2×XT/chloramphenicol medium were inoculated and agitated for 4 hours at 37° C. and 180 rpm. To enable a parallel operation 4 "Deep Well" plates (Qiagen, each having 24 wells) were used for this purpose. After infection of the XL1 Blue cells with each $10^{11}$ cfu M13KO7 helper phages an incubation was carried out for 30 min at 37° C. After additional 30 min at 37° C. and 180 rpm the addition of 50 mg/l kanamycin was performed. Then, agitation was continued for 30 min at 37° C. and 220 rpm and the gene expression on pMUBI-1 was induced by adjusting the culture to 0.2 mg/l anhydro-tetracycline (stock solution: 1.0 mg/ml in DMF). The incubator temperature was then decreased to 22° C., and the culture was agitated for 16 hours at 180 rpm. The cells were finally sedimented by centrifugation (30 min, 5,000 g, 4° C.), and the supernatants were transferred into fresh "Deep Well" plates. The phagemids contained were precipitated by addition of 1 volume of 20% (w/v) PEG 6,000, 2.5 M NaCl and incubation for 1 hour on ice and sedimented by centrifugation (30 min, 5,000 g, 4° C.). The phagemids were then dissolved in 1.0 ml of sterile ice-cold PBS and mixed 1:1 with 6% PBST and incubated for 1 hour at RT.

For carrying out the ELISA one well of a microtiter plate per each monoclonal phagemid to be analyzed was filled with antigen at 4° C.—and one was filled with BSA solution. For the saturation of the remaining binding sites on the plastic surface each of the wells was blocked by 3% BSA (w/v) PBST 0.5. Afterwards, the wells were rinsed three times with PBST 0.1 and tapped out. Then, 100 μl each of the phagemid solutions prepared above were pipetted into the respective wells of the plate. After an incubation period of 2 hours washing was carried out three times with PBST 0.1. For the detection of bound phagemids an M13 antibody peroxidase conjugate (Amersham Pharmacia Biotech) was diluted in a ratio of 1:5,000 in PBST 0.1, and 100 μl were added to each of the wells. After 1 hour of incubation at RT the wells were rinsed three times with PBST 0.1, then three times with PBS. Finally, 100 μl each of the ImmunoPure kit (Pierce) were pipetted into the wells, and the color reaction was then stopped after 15 min by addition of 100 μl of 2 M $H_2SO_4$. The extinction was measured by means of a Sunrise Remote Reader (Tecan) at 450 nm.

The DNA of ubiquitin variations from phagemids which in the ELISA showed a relatively strong binding signal to the respective antigen—but not to BSA—(approximately 20) was sequenced by means of primer SEQ ID NO. 14 and the method described above. A portion of the DNA sequences analyzed exhibited shifts of the reading frame or amber stop codons and were thus not further used. Amino acid substitutions of ubiquitin variations which were obtained in this manner and further analyzed are exemplarily listed in Table 1.

TABLE 1

Amino Acid Substitutions in the Region of the Binding Site Generated de novo of Ubiquitin-based Modified Proteins After Selection Against Different Target Substances by Means of Phage Display

|  | Selection | Pos. 2: | Pos. 4: | Pos. 6: | Pos. 62: | Pos. 63: | Pos. 64: | Pos. 65: | Pos. 66: |
|---|---|---|---|---|---|---|---|---|---|
| SPU[1] | — |  | Gln | Phe | Lys | Gln | Lys | Glu | Ser | Thr |
| SPU-1-D10 | RecGLP1-R | Ser | Phe | Pro | Tyr | Ser | Lys | Pro | Ser |
| SPU-2-A7 | $F_c$ IgM | Ser | Leu | Pro | Pro | Pro | Gly | Arg | Asn |
| SPU-3-H13 | HG | Gly | Gly | Lys | Phe | Phe | Val | Thr | Asn |

TABLE 1-continued

Amino Acid Substitutions in the Region of the Binding Site Generated de novo of Ubiquitin-based Modified Proteins After Selection Against Different Target Substances by Means of Phage Display

| | Selection | Pos. 2: | Pos. 4: | Pos. 6: | Pos. 62: | Pos. 63: | Pos. 64: | Pos. 65: | Pos. 66: |
|---|---|---|---|---|---|---|---|---|---|
| SPU-15-G7 | TNFα | Tyr | Cys | Asn | Asn | Leu | Ser | Trp | Gln |
| SPU-15-E1 | TNFα | Gln | Ala | Ile | Met | Phe | Gln | Thr | Ser |

[1]SPU: Ubiquitin protein backbone without substitutions in the binding pocket

Example 5

Preparation of Ubiquitin Variations in an In Vitro Transcription/Translation System and Selection of Ubiquitin Variations Against Proteins by Means of Ribosomal Display The provision of an expression construct for the in vitro transcription/translation as well as the selection of binding proteins by means of ribosomal display was done according to Schaffitzel et al. (2001). However, in contrast to this no library of antibody fragments was used in the present case but libraries of ubiquitin variations analogous to those described in example 2. One of these libraries was prepared on the basis of the DNA sequence (SEQ ID NO. 1) for a modified ubiquitin protein backbone having the substitutions Ile44Ala, Lys48Arg, Arg54Leu, Val70Ala, Arg72Leu, Gly75Ala, as well as the deletion of Gly76. A second library was prepared on the basis of the DNA sequence (SEQ ID NO. 15) for a modified ubiquitin protein backbone carrying the substitution Phe45Trp.

In a first step, the synthetic genes for the ubiquitin variations representing the library which were mutagenized at 8 codons according to example 2 were prepared on the basis of SEQ ID NO. 1 or SEQ ID NO. 15, respectively, by means of PCR. This was performed in a volume of 50 µl using Pfu polymerase (Promega). For this purpose, 5 µl of the provided 10×Pfu buffer as well as 4 µl dNTP mix were used and filled up with H$_2$O. Furthermore, the sample contained 2.5 µl of each of the flanking primers (SEQ ID NO. 16 and SEQ ID NO. 17 for the library on the basis of SEQ ID NO. 1 as well as SEQ ID NO. 18 and SEQ ID NO. 19 for the library of SEQ ID NO. 15; 10 µM) for the introduction of the desired base pair substitutions. As a template. 1.0 ng of each of the plasmid DNAs was used which carried the non-mutated synthetic ubiquitin gene SEQ ID NO. 1 or SEQ ID NO. 15. After addition of 2.5 U of Pfu polymerase an incubation was carried out in 25 cycles for 1 min each at 94° C., 1 min at 65° C. and for 1.5 min at 72° C. A final incubation was performed for 5 min at 72° C. The desired PCR product was isolated by means of preparative agarose gel electrophoresis and the QIAquick Gel Extraction kit (Qiagen).

The spacer which comprises a portion of the envelope protein III of bacteriophage M13 and which in the course of the in vitro translation pushes the nascent protein out of the ribosomal channel to thus enable an optimal presentation of the ubiquitin variation was synthesized in two successive PCR reactions. This was first done in a total volume of 50 µl using 5 µl of the provided 10×Pfu buffer, 4 µl dNTP mix and an appropriate amount of H$_2$O. Furthermore, the sample contained 2.5 ml each of the flanking primers (SEQ ID NO. 20 and Seq ID 21; 10 µM) as well as 1.0 ng DNA of the bacteriophage M13. After addition of 2.5 U of Pfu polymerase the incubation was performed in 25 cycles each of 1 min at 94° C., 1 min at 65° C. and for 1.5 min at 72° C. A final incubation was done for 5 min at 72° C. The desired PCR product was isolated by means of preparative agarose gel electrophoresis, the QIAquick Gel Extraction kit (Qiagen) and served as a template for the second PCR reaction. This was performed using Pfu polymerase (Promega) in a volume of 50 µl. For this purpose 5 µl of the supplied 10×Pfu buffer as well as 4 µl dNTP mix were used and filled up with H$_2$O. Furthermore, the sample contained 2.5 µl of each of the flanking primers (SEQ ID NO. 22 and SEQ ID NO. 21; 10 µM). As a template, 1.0 ng each of the DNA from the previous PCR reaction was used. After addition of 2.5 U of Pfu polymerase the incubation was carried out in 25 cycles each for 1 min at 94° C., 1 min at 55° C. and for 1.5 min at 72° C. A final incubation was done for 5 min at 72° C. The desired PCR product was isolated by means of preparative agarose gel electrophoresis and the QIAquick Gel Extraction kit (Qiagen).

In the following step the synthetic genes for the ubiquitin variations representing the library which had been mutagenized at 8 codons were fused to the spacer DNA prepared by means of a linking PCR reaction. This was performed by means of Pfu polymers (Promega) in a volume of 50 µl. For this purpose, 5 µl of the supplied 10×Pfu buffer as well as 4 µl dNTP mix were used and filled up with H$_2$O. Furthermore, the sample contained 2.5 µl of each of the flanking primers (SEQ ID NO. 23 and SEQ ID NO. 21; 10 µM). As a template, 500 ng each of the library DNA and 500 ng spacer DNA from the previous PCR reaction were used. After the addition of 2.5 U of Pfu polymerase the incubation was carried out in 25 cycles each for 1 min at 94° C., 1 min at 55° C. and for 1.5 min at 72° C. A final incubation was done for 5 min at 72° C. The desired PCR product was isolated by means of preparative agarose gel electrophoresis and the QIAquick Gel Extraction kit (Qiagen).

In the final step appropriate regulative sequences (T7 promoter, ribosomal binding site) were introduced for the in vitro transcription/translation reaction by means of a further PCR reaction and the linear expression construct was completed. The reaction was carried out in a sample volume of 500 µl wherein approx. 500 ng of the product obtained in the previous PCR reaction was employed and Taq polymerase was used. The reaction sample—adapted to the tenfold volume—was pipetted as carried out in Example 2 from 10×Taq buffer, 25 mM MgCl$_2$, dNTP mix as well as the flanking primers (SEQ ID NO. 24, SEQ ID NO. 21; 10 µM). After filling up with H$_2$O 2.5 U of Taq polymerase were added and the PCR program was started. In 25 cycles the incubation was carried out for each 1 min at 94° C., 1 min at 65° C. and for 1.5 min at 72° C. A final incubation was carried out for 5 min at 72° C. The desired PCR product was isolated by means of preparative agarose gel electrophoresis, the QIAquick Gel Extraction kit (Qiagen) and could be used directly for the in vitro transcription/translation reaction.

For the in vitro transcription/translation reaction the RTS100 E. coli kit (Roche Cat. No. 3186 148) was used according to the manufacturer's instructions. For this purpose, 24.0 µl of E. coli lysate, 20.0 µl of the reaction mix, 24.0 µl of amino acid mix (without Met), 2.0 µl methionine, 10.0 µl reaction buffer (10×), 2.0 µl MgAc (500 mM), 2.0 ml Anti_ssrA DNA (200 µM) as well as 20.0 µl of the respective DNA library (0.5-1.0 µg) were cautiously mixed by means of the pipette and incubated for 60 min at 30° C. or 37° C. The following steps were carried out in the cool room or on ice, respectively. The sample was cooled for 5 min on ice and the reaction was stopped by the addition of 400 µl WBT (50 mM Tris/Hcl (pH 7.5), 150 mM NaCl, 50 mM MgAc, 0.1% TWEEN® 20 non-ionic detergent) containing 3% BSA. This buffer may optionally contain 2.5 mg/ml heparin (Sigma). The insoluble portions of the sample were sedimented for 5 min at 13,000 rpm and 4° C. wherein the ternary complexes consisting of the ubiquitin variation, the corresponding mRNA and the ribosome remained in the supernatant.

As an affinity matrix for the isolation of ternary ribosomal complexes with ubiquitin variations presented on the surface which should bind to previously defined target substances 2 wells of a microtiter plate were coated with the corresponding substance. As the target substances served recombinantly prepared growth factor VEGF which was immobilized over night at 4° C. on the microtiter plate. Unoccupied binding sites on the surface of the microtiter plate were blocked by incubation of the wells each with 400 µl 3% BSA in WBT for 90 min at RT. After removal of the blocking solution 250 µl of the solution containing the ternary ribosomal complexes from the in vitro transcription/translation reaction were added per well and incubated for 60 min at 4° C. and 50 rpm. Unbound complexes were then removed by washing five times with e.g. WBT (300 µl per well, 3 min, 4° C., 50 rpm) and vigorous tapping. Complexes bound to the affinity matrix were finally split by means of 100 ml EB (50 mM Tris/HCl (pH 7.5), 1.5 M NaCl, 20 mM EDTA)—this buffer may optionally contain 50 µg/ml RNA from yeast (Sigma)—per well and incubation for 5 min at 4° C. and 50 rpm into mRNA, protein and the ribosomal subunits.

The isolation of RNA from the suspension obtained was carried out as rapid as possible at room temperature and by using the RNAeasy kit of Qiagen (Cat. Nr. 74104) according to the manufacturer's instructions. In this case, the elution of the RNA was carried out in the final step with 30 µl RNase-free $H_2O$. For the degradation of DNA of linear expression constructs which might have possibly been carried over the RNA solution thus obtained was treated with DNase I (Invitrogen). For this purpose, an addition of 3 µl of DNAse buffer (10×) and 3 µl DNase I (1 U/µl) and an incubation for 15 min at room temperature were carried out. The DNase was then inactivated by the addition of 3 µl of 25 mM EDTA and incubation for 10 min at 65° C. The RNA thus obtained was thereafter complemented by means of the reverse transcriptase reaction. For this purpose, first 8.5 µl of the RNA were mixed with 0.5 µl of the oligodeoxynucleotide T7te (SEQ ID NO. 21; 100 µM) and 4.0 µl dNTP (2.5 mM each), incubated for 5 min at 65° C. and then placed on ice for 1 min. Then 4.0 µl RT buffer (5×), 1.0 µl DTT (0.1 M), 1.0 µl RNAsin (Promega) and 1.0 µl SS reverse transcriptase III (200 u/µl; Invitrogen) were added as further components and incubated for 60 min at 55° C.

The reaction sample from the reverse transcriptase reaction was used directly in a PCR for the new re-amplification of the genetic information of enriched ubiquitin variations as well as for the reintroduction of the regulative sequences for a new selection cycle. For this purpose, two successive PCR reactions were carried out using the Expand High Fidelity PCR system (Roche) in a total volume of 50 µl. For this purpose, 5 µl of the supplied 10× buffer (including 15 mM $MgCl_2$) as well as 4 µl dNTP mix were used and filled up with $H_2O$. Furthermore, the sample contained 2.5 µl each of flanking primers (SEQ ID NO. 23 and SEQ ID NO. 21; 10 µM) as well as 2.5 µl of dimethylsulfoxide (DMSO). As the template either 2.5 or 5.0 µl of the previous RT reaction was used. After the addition of 0.75 µl polymerase mix (3.5 u/µl) an incubation was carried out in 25 cycles each for 15 sec at 94° C., 30 sec at 50° C. and for 1.0 min at 72° C. A final incubation was done for 7 min at 72° C. The desired PCR product was isolated by means of a preparative agarose gel electrophoresis as well as the QIAquick Gel Extraction kit (Qiagen) and could directly be employed for the second PCR reaction. Therefore, 5 µl of the supplied 10× buffer (including 15 mM $MgCl_2$) as well as 4 µl dNTP mix were used and filled up with $H_2O$. Furthermore, the batch contained 2.5 µl each of flanking primers (SEQ ID NO. 24 and SEQ ID NO. 21; 10 µM). As the template the total DNA from the previous PCR reaction was used. After addition of 0.75 µl polymerase mix (3.5 u/µl) an incubation was carried out in 25 cycles each for 15 sec at 94° C., 30 sec at 50° C. and for 1.0 min at 72° C. A final incubation was done for 7 min at 72° C. A final incubation was done for 7 min at 72° C. The desired PCR product was isolated by means of a preparative agarose gel electrophoresis as well as the QIAquick Gel Extraction kit (Qiagen) and could directly be employed for the in vitro transcription/translation of a new selection cycle.

Alternatively, the cloning of the respective gene into expression vector pET20B(-) (see above) was carried out. This enables the analysis of ubiquitin variations obtained with respect to their DNA sequence, the recombinant preparation thereof in E. coli as well as the one-step purification thereof by means of immobilized metal chelate affinity chromatography (IMAC) using a carboxyterminally fused hexa-histidine peptide (see below). Amino acid substitutions of ubiquitin variations which were obtained in this manner and further analyzed are exemplarily listed in table 2.

TABLE 2

Amino Acid Substitutions in the Region of the Binding Site Generated de novo of Ubiquitin-based Modified Proteins After Selection Against Different Target Substances by Means of Ribosomal Sisplay

|  | Selection | Pos. 2: | Pos. 4: | Pos. 6: | Pos. 62: | Pos. 63: | Pos. 64: | Pos. 65: | Pos. 66: |
|---|---|---|---|---|---|---|---|---|---|
| SPU[1] | — | Gln | Phe | Lys | Gln | Lys | Glu | Ser | Thr |
| SPU-11-RD3/1 | VEGF | Arg | Arg | Ala | Arg | His | Gly | Thr | Ser |
| SPU-11-A8 | VEGF | Leu | Leu | Trp | Ser | Leu | Ser | Gly | Ile |
| SPU-11-58 | VEGF | Leu | Leu | Trp | Arg | Ser | Asp | Leu | Asn |
| SPW-11-A1 | VEGF | Phe | Trp | Val | Gly | His | Gln | Arg | Gly |

[1] SPU: Ubiquitin protein backbone without substitutions in the binding pocket

Example 6

Preparation and Purification of the Ubiquitin-Based Modified Proteins

The characterization of the proteinchemical properties of selected ubiquitin variations from phagemids giving a relatively strong binding signal in the ELISA and with functional DNA sequence was carried out after cloning of the respective gene into expression vector pET20B(–) (see above). This enabled the recombinant preparation of the respective variation by means of *E. coli* BL 21/pUBS as well as the one-step purification thereof by means of immobilized metal chelate affinity chromatography (IMAC) using a carboxyterminal hexa-histidine peptide.

For the recombinant preparation of the ubiquitin-based modified proteins having novel binding characteristics 50 ml of 2×YT/amp/kan medium were inoculated with a respective single colony and agitated for 16 hours at 37° C. and 220 rpm. With this pre-culture 1.5 liters of 2×YT/amp/kan medium was inoculated in a ratio of 1:50 and incubated at 37° C. and 220 rpm until a cell density of $OD_{600}=0.5$ was reached. After induction of the expression of the foreign gene by addition of 1 mM/l α-D-isopropyl thiogalactoside (IPTG) agitation was continued for further 3 hours at 37° C. and 220 rpm. The cells were then sedimented by centrifugation (30 min, 5,000 g, 4° C.) and resuspended in 40 ml NPI-20 (50 mM $NaH_2PO_4$, pH 8.0, 300 mM NaCl, 20 mM imidazole). The cell disruption was done by incubation for half an hour with 200 μg/ml lysozyme and 500 U of benzonase at RT as well as a five times of ultrasonic pulsing each for 15 sec. The cell debris was sedimented by centrifugation (30 min, 15,000 g, 4° C.) and the supernatant containing the total soluble cell protein could directly be employed in the subsequent IMAC.

The chromatography was performed on an ÄKTA™ Explorer FPLC unit (Amersham Pharmacia Biotech) using a 5 ml HiTrap Chelating HP column (Amersham Pharmacia Biotech) at RT and a flow rate of 5 ml/min. First, the column was equilibrated with 5 column volumes of NPI-20 whereupon the total cell protein was passed over the column. Unbound protein was washed off by rinsing with 30 column volumes of NPI-20. The elution was done with a linear gradient of 20 nM to 250 mM of imidazole in a total of 20 column volumes while the eluate was collected in fractions of 2.5 ml each. The fractions containing the purified ubiquitin variation were analyzed by means of SDS polyacrylamide gel electrophoresis and combined. The yields of the recombinant ubiquitin variations achieved were between 10 and 30 mg/l of culture volume.

Example 7

Characterization of the Binding Characteristics of Ubiquitin-Based Modified Proteins having Novel Binding Characteristics The binding of the ubiquitin variations selected in each case and which were purified as described in example 6 on recGLP1-R, $F_c$ IgM, and HC was detected in the ELISA with either an Ni/NTA peroxidase conjugate (Qiagen) or with an ubiquitin antiserum (Sigma) from rabbit. For this purpose, the wells of microtiter plates were filled over night at 4° C. with the respective antigen and e.g. BSA for the detection of unspecific binding and blocked for 2 hours with 3% BSA (w/v) PBST 0.5 for the saturation of the remaining binding sites. The plates were then rinsed three times with PBST 0.1 and tapped out. Thereafter, 100 μl of each of the solutions of the respective modified purified protein in PBST 0.1 in serial concentrations (ranging from undiluted up to a dilution of 1:16) were pipetted into the wells of the plate. The incubation period of 2 hours was followed by rinsing three times with PBST 0.1. For the detection of the bound modified protein the Ni/NTA peroxidase conjugate was diluted in a ratio of 1:500, or the ubiquitin antiserum was diluted in a ratio of 1:10 in PBST 0.1, respectively, and 100 μl each were added to each of the wells. The incubation for one hour at RT was either directly followed by the detection of the Ni/NTA peroxidase conjugate (see below) or by the incubation with an rabbit antibody peroxidase conjugate (1:2,500 in PBST 0.1), respectively, for one hour at RT. For detection the wells were rinsed three times with PBST 0.1, then three times with PBS. Finally, 100 μl each of the ImmunoPure kit were pipetted thereto and the color reaction was then stopped after 15 min by addition of 100 ml of 2 M $H_2SO_4$. The extinction measurement the was done by means of a Sunrise Remote Reader (Tecan) at 450 nm. The values of the absorption intensity obtained were evaluated by means of the "Sigma Plot" computer program. For this purpose, the extinction measured in each case was plotted against the corresponding protein concentration employed, and the curve obtained was fitted by means of non-linear regression using formula (1).

$$y = \frac{a * x}{(b + x)} \tag{1}$$

Assuming an association/dissociation equilibrium between the immobilized antigen and the modified protein thus is:

x=concentration of the modified protein employed
y=concentration of the complex of antigen/modified protein (here measured indirectly via the enzymatic activity of the reporter enzyme)
a=total concentration of immobilized antigen
b=dissociation constant ($K_D$)

The binding curves obtained from an ELISA experiment of this type for the ubiquitin variation SPU-1-D10 which had been obtained from the affinity enrichment on recGLP1-R by means of phage display according to examples 3 and 4 are exemplarily illustrated in FIG. 5. Furthermore, in FIG. 6 is illustrated the binding curves of the ubiquitin variation SPW-11-A1 which resulted from the affinity enrichment to VEGF by means of ribosomal display according to Example 5. The binding data obtained for the individually selected ubiquitin-based modified proteins having novel binding properties are summarized in Table 3.

For a quantitative analysis of the binding of variations of ubiquitin to a previously defined antigen a BIACORE 3000 system (Biacore) was also used. For such surface plasmon resonance (SPR) measurements a carrier (sensor chip) capable of immobilizing the analyte was positioned within the device and coupled to the microflow system (Integrated μ Fluidic Cartridge, IFC) integrated therein. This enabled a continuous fluid flow from the buffer reservoir across the chip surface and a quasi in solution detection of the binding to the analyte carrier.

First, for a measurement the target molecule, e.g. VEGF, was coupled by means of NHS/EDC coupling via primary amine groups to the carboxymethyl dextrane surface of the sensor chip CM5 (Biacore) according to the manufacturer's instructions. The measurements were carried out in a continuous buffer flow of 35 μl/min at 25° C. As a running buffer and a solvent for the proteins used PBS (filter sterilized and degassed) supplemented with 0.005% P-20 detergent (Biacore) was used. The interaction with the immobilized VEGF of different concentrations of the ubiquitin variations which were injected via the sample loop could be detected due to the generated SPR signal. The signal was quantified as so-called resonance units (RU) depending on the time and corresponding binding curves were generated. The binding curves obtained were evaluated using the BIAevaluation software (Version 3.1; Biacore), and the value of the dissociation constant ($K_D$) was determined. The binding curves of the ubiquitin variation SPU-11-58 which resulted from the affinity enrichment to VEGF by means of ribosomal display according to Example 5 obtained from such a BIACORE experiment are exemplarily illustrated in FIG. 7. The binding data obtained for the individual selected ubiquitin-based modified proteins having novel binding properties are summarized in Table 3.

TABLE 3

Dissociation Constants of Complexes of Selected Ubiquitin-based Modified Proteins and Different Target Substances

| modified protein | target substance | apparent $K_D$ value |
|---|---|---|
| SPU-1-D10[1] | recGLP1-R | 166 ± 0.06 nM |
| SPU-2-A7[1] | $F_c$ IgM | 9.4 ± 0.9 μM |
| SPU-3-H13[1] | HC | 10.7 ± 1.0 nM |
| SPU-11-RD3/1[2] | VEGF | 25 μM |
| SPU-11-A8[2] | VEGF | 70 nM |
| SPU-11-58[2] | VEGF | 50 nM |
| SPW-11-A1[1] | VEGF | 1.2 ± 0.1 μM |
| SPU-15-G7[1] | TNFα | <1.0 μM |
| SPU-15-E1[1] | TNFα | <1.0 μM |

[1]analysis by means of ELISA;
[2]analysis by means of BIACORE

Furthermore, individual modified proteins were evaluated with respect to the specificity of their binding. For this purpose, ELISA experiments were carried out as described above using a single appropriate concentration of the modified proteins. For this purpose, respective wells of the microtiter plate were filled with the target substrate as well as structurally similar substances. The binding curves of ubiquitin variation SPU-3-H13 which resulted from the affinity enrichment to HC according to Examples 3 and 4 obtained in such an ELISA experiment are exemplarily illustrated in FIG. 8.

Example 8

Improvement of the Binding Characteristics of Ubiquitin-Based Binding Proteins by Site-Directed Secondary Mutagenesis Based on the ubiquitin variation SPU-2-A7 which shows a de novo binding property against $F_c$ IgM a generally applicable strategy for the affinity maturation was established. This comprised first a new random substitution of selected positions in the binding site generated de novo on the DNA level as well as the subsequent parallel expression, purification and binding analysis of 96 of the respective variations. By the use of this "96 format" it is possible to transfer the strategy to laboratory roboters and thus to carry out the analysis of variations with high throughput.

For this purpose, the codons of each of two positions (62 and 63 as well as 64 and 65) were randomly mutated by means of PCR in two parallel samples. The corresponding reactions were carried out each in 50 μl wherein approximately 1.0 ng of the gene for SPU-2-A7 inserted into pET20B(-) were used and Taq polymerase was employed. The reaction sample was pipetted as described in Example 2 from 10× Taq buffer, 25 mM MgCl$_2$, dNTP mix as well as the flanking primers (SEQ ID NO. 12, SEQ ID NO. 25 for the mutation of positions 62 and 63 or SEQ ID NO. 12, SEQ ID NO. 26, respectively, for the mutation of positions 64 and 65; 10 μM). After filling up with H$_2$O 2.5 U of Taq polymerase were added and the PCR program was started. In 25 cycles the incubation was carried out each for 1 min at 94° C., 1 min at 55° C. and for 1.5 min at 72° C. A final incubation was carried out for 5 min at 72° C. The desired PCR products were isolated by means of preparative agarose gel electrophoresis and the QIAquick Gel Extraction kit (Qiagen). The DNA-fragments obtained each representing the libraries of SPU-2-A7 mutagenized at positions 62/63 or 64/65, respectively, were cut by means of preparative NdeI/XhoI restriction cleavage and isolated again by means of preparative agarose gel electrophoresis. The insertion of the genetic libraries for the modified SPU-2-A7 was carried out into expression vector pET20B(-) (Novagen, c.f. Example 1) for the production of the corresponding protein.

Following the transformation of electrocompetent E. coli, e.g. Nova-Blue or BL-21 cells, single colonies were obtained which contained the genetic information of one clone each of the library obtained in the form of the expression plasmid. Using 96 of these single colonies 300 μl 2×YT/amp/kan each were inoculated and agitated over night at 37° C. and 220 rpm. With 100 μl of each of said cultures 96×4 ml of 2×YT/amp/kan were inoculated and incubated at 37° C. and 220 rpm until a cell density of OD$_{600}$=0.5 was reached. For this purpose, four 24-well culture plates (Qiagen) were used in each case. After induction of the expression of the foreign gene by addition of 1 mM/L α-D-isopropyl thiogalactoside (IPTG) agitation was continued for additional 3 hours at 37° C. and 180 rpm or over night at 30° C. and 180 rpm. The cells were then sedimented by centrifugation (30 min, 4,000 g, 4° C.) and the supernatant was removed. The cell disruption was carried out by physical (shock freezing and thawing) or chemical lysis (detergents) as well as by addition of lysozyme (200 μg/ml) and benzonase (10 u/ml in the final volume). The purification of the variations of SPU-2-A7 from the total cell protein obtained was carried out by means of the BioRobot 9600 kit from Qiagen and a manually operated vacuum station (QIAvac 96, Qiagen). The protein solutions obtained were analyzed with respect to their binding to $F_c$ IgM in a qualitative manner in an ELISA experiment corresponding in its experimental set-up to that of Example 7.

For the verification of the functionality of their gene or the analysis of the substitutions obtained, respectively, variations of SPU-2-A7 showing a relatively strong binding signal in the ELISA were subjected to DNA sequencing. Promising candidates were prepared on an 1.5 L scale in a recombinant manner and purified by means of immobilized metal chelate affinity chromatography (IMAC) using the hexa-histidine peptide fused to the carboxyterminus. For the quantification of the affinity a concentration-independent ELISA as described in Example 7 was carried out in comparison to SPU-2-A7—the ubiquitin variation on the basis of which the maturation had been performed. The binding curves of the ubiquitin variation SPU-2-A7 as well as of SPU-2-A7(62/63) which were obtained from such an ELISA experiment are exemplarily illustrated in FIG. 9. With a $K_D$=1.0 μM this affinity-maturated variation exhibits a binding strength improved by a factor 10 in comparison to SP-2-A7.

Example 9

Site-Directed Coupling of Two Identical Ubiquitin-Based Proteins via Single Carboxy-Terminal Cysteine Residues by Means of Bis-Maleimide Reagents The linkage of two identical ubiquitin variations was carried out via cysteine residues which were specifically introduced for this purpose by means of bis-maleimido hexane (BMH, Pierce). First, an appropriate codon for cysteine followed by a proline was introduced for this purpose at the 3' end of the reading frame—i.e. at the protein carboxyterminus after the hexa-histidine peptide. In this way, the last proline residue should protect the resulting protein from proteolytic degradation during production and purification. The insertion into pET20B(-) of the corresponding base pairs was carried out by means of the Quick Change™ Site-directed Mutagenesis kit (Stratagene) according to the manufacturer's instructions and by using the oligodeoxynucleotides SEQ ID NO. 27 and SEQ ID NO. 28 as well as the gene of an ubiquitin variation (SEQ ID NO. 15) as a template. The resulting clones were analyzed by means of DNA sequencing and colonies having the expression plasmid carrying the desired insertion were used for recombinant production and purification according to Example 6.

The purified protein was dialyzed against PBS containing 1 mM EDTA and 5 mM β-mercaptoethanol and employed in a concentration of approx. 1 mg/ml for the following coupling reaction in which PBS, 1 mM EDTA served as the reaction buffer. For this purpose, the free cysteine residue was first reduced by adjusting the protein solution to 100 mM dithiothreitol (DTT) and incubation for 1 hour at room temperature. Thereafter, the reducing reagents were separated from the protein by means of a PD10 Sephadex G-25 M column (Amersham Biosciences), this was added with a twofold molar excess of coupling reagent (stock solution: 100 mM BMH in DMSO) and incubated for one hour at room temperature. Excess BMH was separated again using a PD10 column. To separate only singly reacted coupling reagent which might possibly be present an equimolar amount of freshly reduced protein was again added to the coupling sample thus obtained. This second coupling step was carried out for 2 hours at room temperature.

The coupling sample obtained by this procedure was analyzed by means of SDS-PAGE (FIG. 10) and the degree of coupling was estimated. For the procedure as described above, this was about 40%.

REFERENCES

Ausuebel, F. M., Brent, R., Kinston, R. E., Moore, D. D., Seidmann, J. G., Smith, J. A., and Struhl, K. (1994): Current protocols in molecular biology. John Wiley & Sons, Inc.

Bazarsuren, A., Grauschopf, U., Wozny, M., Reusch, D., Hoffmann, E., Schaefer, W., Panzner, S., and Rudolph, R. (2002) In vitro folding, functional characterization, and disulfide pattern of the extracellular domain of human GLP-1 receptor. Biophys. Chem. 96, 305-318.

Beal, R., Deveraux, Q., Xia, G., Rechsteiner, M., and Pickart, C. (1996) Surface hydrophobic residues of multiubiquitin chains essential for proteolytic targeting. Proc. Natl. Acad. Sci. USA 93, 861-866.

Berman, H. M., Westbrook, J., Feng, Z., Gilliland, G., Bhat, T. N., Weissig, H., Shindyalov, I. N., and Bourne, P. E. (2000) The Protein Data Bank. Nucleic Acid Res., 28, 235-242.

Beste, G., Schmidt, F. S., Stibora, T., and Skerra, A. (1999) Small antibody-like proteins with predescribed Ligand specificities derived from the lipocalin fold. Proc. Natl. Acad. Sci. USA 96, 1898-1903.

Bird, R. E., Hardman, K. D., Jacobson, J. W., Johnson, S., Kaufman, R., Lee, S. M., Pope, H. S., Riordan, G. S., and Whitlow, M. (1988) Single-chain antigen-binding proteins. Science 242, 423-426.

Burch, T. J. and Haas, A. L. (1994) Site-directed mutagenesis of Ubiquitin. Differential roles for Arginine in the interaction with Ubiquitin-activating enzyme. Biochemistry 33, 7300-7308.

Brinkmann, U., Reiter, Y., Jung, S. H., Lee, B., and Pastan, I. (1993) A recombinant immunotoxin containing a disulfide-stabilized Fv-fragment. Proc. Natl. Acad. Sci. USA 90, 7538-7542.

Buchberger A, Howard M J, Proctor M, Bycroft M, National Library of Medicine, J Mol. Biol. 2001 Mr 16; 307(1); 17-24.

Calter, P., Kelley, R. F., Rodrigues, M. L., Snedecor, B., Covarrubias, M., Velligan, M. D., Wong, W. L. T., Rowland, Kotts, C. E., Carver, M. E., Yang, M., Bourell, J. H., Shepard, H., Connolly, M. L. (1983) "Solvent-Accessible Surfaces of Proteins and Nucleic Acids" Science, 221, 709-713.

M. and Henner, D. (1992) High level *Escherichia coli* expression and production of a bivalent humanized antibody fragment. Biotechnology 10, 163-167.

Daugherty, P. S., Chen, G., Olsen, M. J., Iverson, B. L., and Georgiou, G. (1998) Antibody affinity maturation using bacterial surface display. Protein Eng. 11, 825-832.

Dübel, S, and Kontermann, R. E. (2001) Recombinant Antibodies. In: Kontermann, R. and Dübel, S. (Hrsg.) "Antibody Engineering." Springer Verlag, Heidelberg.

Filippi, M., Tribioli, C., and Toniolo, D. (1990) Linkage and sequence conservation of the X-linked genes DX253 (P3) and DXS254E (GdX) in mouse and man. Genomics 7, 453-457.

Griep, R. A., van Twisk, C., van der Wolf, J. M., and Schots, A. (1999) Fluobodies: green fluorescent single-chain Fv fusion proteins. J. Immunol. Methods 230, 121-130.

Hanes, J., Jermutus, L., Weber-Bornhauser, S., Bosshard, H. R., and Plückthun, A. (1998) Ribosome display efficiently selects and evolves high-affinity antibodies in vitro from immune libraries. Proc. Natl. Acad. Sci. USA 95, 14130-14135.

Hanes, J., Schaffitzel, C., Knappik, A., and Plückthun, A. (2000) Picomolar affinity antibodies from a fully synthetic naive library selected and evolved by ribosome display. Nature Biotechnology 18, 1287-1292.

He, M. and Taussig, M. J. (1997) Antibody-ribosome-mRNA (ARM) complexes as efficient selection particles for in vitro display and evolution of antibody combining sites. Nucleic Acids Res. 25, 5132-5134.

Holliger, P., Prospero, T., and Winter, G. (1993) "Diabodies": small bivalent and bispecific antibodies. Proc. Natl. Sci. USA 90, 6444-6448.

Hoogenboom, H. R., de Bruine, A. P., Hufton, S. E., Hoet, R. M., Arends, J. W., and Roovers, R. C. (1998) Antibody phage display technology and its applications. Immunotechnology 4, 1-20.

Jones, D. and Candido, E. P. (1993) Novel ubiquitin-like ribosome protein fusion genes from the nematodes *Caenorhabditis elegans* and *Caenorhabditis briggsae*. J. Biol. Chem. 268, 19545-195451.

Kieke, M. C., Cho, B. K., Boder, E. T., Kranz, D. M., and Wittrup, K. D. (1997) Isolation of anti-T cell receptor scFv mutants by yeast surface display. Protein Eng. 10, 1303-1310.

Knappik, A., Ge, S., Honegger, A., Pack, P., Fischer, M., Wellnhofer, G., Hoess, A., Wölle, J., Plückthun, A., and Virnekäs, B. (2000) Fully synthetic human combinatorial antibody libraries (HuCAL) based on modular consensus frameworks and CDRs randomized with trinucleotides. J. Mol. Biol., 296, 57-86.

Koide, A., Bailey, C. W., Huang, X., and Koide, S. (1998) The fibronectin type III domain as a scaffold for novel binding proteins. J. Mol. Biol. 284, 1141-1151.

Kuchner, O. and Arnold, F. H. (1997): Directed evolution of enzyme catalysts. TIBTECH 15, 523-530.

Kumar, S., Yoshida, Y., and Noda, M. (1993) Cloning of a cDNA which encodes a novel ubiquitin-like protein. Biochem. Biophys. Res. Commun. 195, 393-399.

Larsen C N, Wang H., National Library of Medicine; J Proteome Res. 2002 September-October; 1(5): 411-9.

Marx, J. (2002) Ubiquitin lives up to its name. Science 297, 1792-1794.

McConell S, and Hoess R. H. (1995): Tendamistat as a scaffold for conformationally constrained phage peptide libraries. J. Mol. Biol. 250, 460-470.

Michiels, L., Van der Rauwelaert, E., Van Hasselt, F., Kas, K., and Merregaert, J. (1993) Fau cDNA encodes a ubiquitin-like-S30 fusion protein and is expressed as an antisense sequence in the Finkel-Biskis-Reilly murine sarcoma virus. Oncogene 8, 2537-2546.

Miura, T., Klaus, W., Gsell, B., Miyamoto, C., and Senn, H. (1999) Characterization of the binding interface between ubiquitin and class 1 human ubiquitin-conjugating enzyme 2b by multidimensional heteronuclear NMR spectroscopy in solution. J. Mol. Biol. 290, 213-228.

Muller, B. H., Chevrier, D., Boulain, J.-C., and Guesdon, J.-L. (1999) Recombinant single-chain Fv antibody fragment-alkaline phosphatase conjugate for one-step immunodetection in molecular hybridization. J. Immunol. Methods 227, 177-185.

Muller, S., Hoege, C., Pyrowolakis, G., and Jentsch, S. (2001) SUMO, ubiquitin's mysterious cousin. Nat. Rev. Mol. Cell. Biol. 2, 202-210.

Murzin A. G., Brenner S. E., Hubbard T., and Chothia C. (1995). SCOP: a structural classification of proteins database for the investigation of sequences and structures. J. Mol. Biol. 247, 536-540.

Nord, K., Gunneriusson, E., Ringdahl, J., Stahl, S., Uhlen, M., and Nygren, P. A. (1997); Binding proteins selected from combinatorial libraries of an beta-helical bacterial receptor domain. Nat. Biotechnol. 8, 772-777.

Odegrip, R., Coomber, D., Eldridge, B., Herderer, R., Kuhlman, P. A., Ullman, C., FitzGerald, K., and McGregor, D. (2003) CIS display: In vitro selection of peptides from libraries of protein-DNA complexes. PNAS 101, 2806-2810.

Pannekoek, H., van Meijer, M., Schleef, R. R., Loskutoff, d. J., and Barbas, C. F. (1993): Functional display of human plasminogen-activator inhibitor 1 (PAI-1) on phages: Novel perspectives for structure-function analysis by error-prone DNA synthesis. Gene 128, 135-140.

Reiter, Y. and Pastan, I. (1998) Recombinant Fv immunotoxins and Fv fragments as novel agents for cancer therapy and diagnosis. Trends Biotechnol. 16, 513-520.

Sambrook, J., Maniatis, T., and Fritsch, E. F. (1989): Molecular Cloning: A laboratory manual. Cold Spring Harbor. Cold Spring Harbor Laboratory Press, New York.

Sambrook, J., Fritsch, E. F., and Maniatis, T. (2001) "Molecular Cloning: A Laboratory Manual" 3rd ed. Cold Spring Harbor Laboratory Press, Cold Spring Harbor, N.Y.

Shrake, A. and Rupley, J. A. (1973) Environment and Exposure to Solvent of Protein Atoms. Lysozyme and Insuline. J. Mol. Biol. 79, 351-371.

Skena, A. and Plückthun, A. (1988) Assembly of a functional immunoglobulin Fv fragment in *Escherichia coli*. Science 240, 1038-1041.

Schaffitzel, C., Zahnd, C., Amstutz, P., Luginbühl, B., and Plückthun, A. (2001) In vitro selection and evolution of protein-ligand interactions by ribosome display. In: Protein-Protein Interactions, A Molecular Cloning Manual, E. Golemis, Ed. (Cold Spring Harbor Laboratory Press, New York, 2001, pp. 535-567.)

Skerra, A. (2000) Engineered protein scaffolds for molecular recognition. J. Mol. Recognit. 13, 167-187.

Stemmer, W. P. C. (1994): Rapid evolution of a protein in vitro by DNA shuffling. Nature 370, 389-391.

Vijay-Kumar, S., Bugg, C. E., and Cook, W. J. (1987) Structure of ubiquitin refined at 1.8 A resolution. J. Mol. Biol. 194, 531-544.

Winter, G. (1998) Synthetic human antibodies and a strategy for protein engineering. FEBS Lett. 430, 92-94.

Wintrode, P. L., Makhatadze, G. I., and Privalov, P. L. (1994) Thermodynamics of ubiquitin unfolding. Proteins Struct. Funct. Genet. 18, 246-253.

What is claimed is:

1. A modified ubiquitin protein comprising a ubiquitin-like folding motif, wherein:
the modified ubiquitin protein comprises substitutions of four to eight amino acids at positions Gln2, Phe4, Lys6, Gln62, Lys63, Glu64, Ser65 and Thr66 of a ubiquitin protein having the amino acid sequence of SEQ ID NO: 35 or the amino acid sequence that is encoded by SEQ ID NO: 15,
wherein
the modified ubiquitin protein binds to a predetermined binding partner, wherein the predetermined binding partner exhibits a binding affinity with respect to the modified ubiquitin that did not exist previously with respect to a ubiquitin polypeptide of SEQ ID NO: 35, and wherein the modified ubiquitin protein has a dissociation constant ($K_D$) of from $10^{-5}$ M to $10^{-12}$ M with respect to the binding partner.

2. The modified ubiquitin protein of claim 1, wherein Gln62, Lys63, Glu64, Ser65 and Thr66 in the protein having the amino acid sequence of SEQ ID NO: 35 or the amino acid sequence that is encoded by SEQ ID NO: 15 are modified.

3. The modified ubiquitin protein of claim 1, wherein the four to eight amino acids at positions Gln2, Phe4, Lys6, Gln62, Lys63, Glu64, Ser65 and Thr66 that are modified include Gln62, Lys63 or both Gln62 and Lys63.

4. The modified ubiquitin protein of claim 1, wherein the protein having the amino acid sequence of SEQ ID NO: 35 or the amino acid sequence that is encoded by SEQ ID NO: 15 is human ubiquitin or another mammalian ubiquitin, and further wherein four to eight amino acids at positions Gln2, Phe4, Lys6, Gln62, Lys63, Glu64, Ser65 and Thr66 are modified so that these modified amino acids comprise the region with binding affinity to the binding partner.

5. The modified ubiquitin protein of claim 4, wherein Gln2, Phe4, Lys6, Glu64, Ser65 and Thr66 are modified.

6. The modified ubiquitin protein of claim 4, wherein Gln62, Lys63, Glu64, Ser65 and Thr66 are modified.

7. The modified ubiquitin protein of claim 4, wherein the four to eight amino acids at positions Gln2, Phe4, Lys6, Gln62, Lys63, Glu64, Ser65 and Thr66 that are modified include Gln62, Lys63 or both Gln62 and Lys63.

8. The modified ubiquitin protein of claim 1, wherein the amino acids are modified by random mutagenesis.

9. The modified ubiquitin protein of claim 1, wherein the binding partner of interest is an antigen or a hapten.

10. The modified ubiquitin protein of claim 1, wherein the binding affinity, expressed in $K_D$, to the binding partner of interest is $10^{-6}$ M to $10^{-12}$ M, $10^{-8}$ to $10^{-12}$ M, or $10^{-9}$ to $10^{-12}$ M.

11. The modified ubiquitin protein of claim 1, wherein the modified ubiquitin protein is produced by a method comprising:
(a) selecting a protein to be modified having the amino acid sequence of SEQ ID NO: 35 or the amino acid sequence that is encoded by SEQ ID NO: 15;
(b) providing a binding partner of interest, wherein the binding partner of interest exhibits a binding affinity with respect to the modified ubitquitin that did not exist previously with respect to the protein having the amino acid sequence of SEQ ID NO: 35 or the amino acid sequence that is encoded by SEQ ID NO: 15;
(c) selecting four to eight amino acids at positions Gln2, Phe4, Lys6, Gln62, Lys63, Glu64, Ser65 and Thr66 of the protein to be modified having the amino acid sequence comprising SEQ ID NO: 35 or the amino acid sequence that is encoded by SEQ ID NO: 15;
(d) modifying four to eight amino acids at positions Gln2, Phe4, Lys6, Gln62, Lys63, Glu64, Ser65 and Thr66 by substitution, and further wherein the ubiquitin-like folding motif present in the protein to be modified having the amino acid sequence of SEQ ID NO: 35 or the amino acid sequence that is encoded by SEQ ID NO: 15 is maintained in the modified ubiquitin protein;
(e) contacting the modified protein with the binding partner of interest provided in step (b); and
(f) detecting a modified protein having a binding affinity with the binding partner predetermined in step (b).

12. The modified ubiquitin protein of claim 11, wherein the method of producing the modified protein further comprises producing a complex comprising bivalent or bispecific binding properties, respectively, by linking the modified ubiquitin protein in a site-specific and covalent manner to a second protein of the same or a different specificity.

13. The modified ubiquitin protein of claim 1, wherein the amino acid substitutions comprise four or more of Gln2Phe, Phe4Trp, Lys6Val, Gln62Gly, Lys63His, Glu64Gln, Ser65Arg, and Thr66Gly.

14. The modified ubiquitin protein of claim 1, further comprising an additional substitution or deletion at Gly75 or Gly76 of the protein having the amino acid sequence of SEQ ID NO: 35 or the amino acid sequence that is encoded by SEQ ID NO: 15.

15. The modified ubiquitin protein of claim 1, wherein the protein of SEQ ID NO: 35 or that is encoded by SEQ ID NO: 15 is a mammalian ubiquitin and the amino acids that are modified amino are acids Gln62, Lys63, Glu64 and Ser65 of the mammalian ubiquitin of SEQ ID NO: 35 or that is encoded by SEQ ID NO: 15.

16. The modified ubiquitin protein of claim 1, wherein at least two amino acids selected from Gln2, Phe4, Lys6, Gln62, Lys63, Glu64, Ser65 or Thr66 that are adjacent to each other in the structure are modified.

17. The modified ubiquitin protein of claim 1, wherein at least two amino acids selected from Gln2, Phe4, Lys6, Gln62, Lys63, Glu64, Ser65 or Thr66 not adjacent to each other in the structure are modified.

18. The modified ubiquitin protein of claim 1, wherein three amino acids selected from Gln2, Phe4, Lys6, Gln62, Lys63, Glu64, Ser65 or Thr66 that are directly adjacent to each other in the sequence are modified.

19. The modified ubiquitin protein of claim 1, wherein four amino acids selected from Gln2, Phe4, Lys6, Gln62, Lys63, Glu64, Ser65 or Thr66 that are directly adjacent to each other in the sequence are modified.

20. The modified ubiquitin protein of claim 1, wherein the modified protein is present in a library.

21. The modified ubiquitin protein of claim 20, wherein the library is an expression library.

22. The modified ubiquitin protein of claim 20, wherein each of the plurality of modified proteins comprises substitutions in at least four (4) of amino acids 2, 4, 6, and 62-66 of SEQ ID NO: 35.

* * * * *